(12) United States Patent
Suzuki et al.

(10) Patent No.: US 9,243,042 B2
(45) Date of Patent: Jan. 26, 2016

(54) PROTEIN FOR CONSTRUCTING PROTEIN COMPLEX FROM CLOSTRIDIUM THERMOCELLUM, AND USE THEREOF

(75) Inventors: Hiroaki Suzuki, Nagoya (JP); Takao Imaeda, Nisshin (JP); Katsunori Kohda, Nisshin (JP)

(73) Assignee: KABUSHIKI KAISHA TOYOTA CHUO KENKYUSHO, Nagakute-cho (JP)

( * ) Notice: Subject to any disclaimer, the term of this patent is extended or adjusted under 35 U.S.C. 154(b) by 675 days.

(21) Appl. No.: 13/072,143

(22) Filed: Mar. 25, 2011

(65) Prior Publication Data

US 2011/0250668 A1 Oct. 13, 2011

(30) Foreign Application Priority Data

Apr. 7, 2010 (JP) ................. 2010-088952

(51) Int. Cl.
   C07K 14/33 (2006.01)
   C12P 7/10 (2006.01)
   C12N 9/24 (2006.01)
   C12N 9/42 (2006.01)

(52) U.S. Cl.
   CPC .............. *C07K 14/33* (2013.01); *C12N 9/2437* (2013.01); *C12N 9/2482* (2013.01); *C12P 7/10* (2013.01); *C12Y 302/01008* (2013.01); *C12P 2203/00* (2013.01); *Y02E 50/16* (2013.01)

(58) Field of Classification Search
   None
   See application file for complete search history.

(56) References Cited

U.S. PATENT DOCUMENTS

| | | | | |
|---|---|---|---|---|
| 5,032,676 | A * | 7/1991 | Deeley et al. | 530/351 |
| 5,073,627 | A * | 12/1991 | Curtis et al. | 530/351 |
| 5,128,450 | A * | 7/1992 | Urdal et al. | 424/85.2 |
| 7,691,972 | B2 * | 4/2010 | Thorsted et al. | 530/350 |
| 2003/0027298 | A1 * | 2/2003 | Bott et al. | 435/183 |
| 2009/0155238 | A1 * | 6/2009 | Weiner et al. | 424/94.61 |
| 2009/0220480 | A1 * | 9/2009 | Gray et al. | 424/94.61 |

(Continued)

FOREIGN PATENT DOCUMENTS

| JP | A-2000-157282 | 6/2000 |
|---|---|---|
| JP | A-2004-236504 | 8/2004 |

(Continued)

OTHER PUBLICATIONS

Grepinet, O., et al., 1988, "Nucleotide sequence and deletion analysis of the xylanase gene (xynZ) of Clostridium thermocellum", Journal of Bacteriology, vol. 170, pp. 4582-4588.*

(Continued)

*Primary Examiner* — Manjunath Rao
*Assistant Examiner* — William W Moore
(74) *Attorney, Agent, or Firm* — Oliff PLC

(57) ABSTRACT

It is an object to provide a protein having a dockerin, which is suited to production in yeasts and other eukaryotic microorganism in which sugar chain modification is predicted, and which provides excellent cohesin-dockerin binding ability, along with a use thereof. The present invention uses, as a protein for constructing a protein complex using a scaffolding protein having a type I cohesin from *Clostridium thermocellum*, a protein having a dockerin having at least one dockerin-specific sequence which is a dockerin-specific sequence associated with cohesin binding in type I dockerins from *C. thermocellum*, and which either has no intrinsic predicted N-type sugar chain modification site or has aspartic acid substituted for the asparagine of an intrinsic predicted N-type sugar chain modification site.

7 Claims, 13 Drawing Sheets

Xyn10C Dockerin

Replace N to A or D

EPPVQVIPGD VNGDGRVNSS DLTLMKRYLL
KSISDFPTPE GKIAADLNED GKVNSTDLLA
LKKLVLREL

(56) References Cited

U.S. PATENT DOCUMENTS

| | | | |
|---|---|---|---|
| 2010/0081786 A1* | 4/2010 | Danishefsky | C07K 9/00 530/322 |
| 2010/0135994 A1* | 6/2010 | Banchereau | A61K 39/21 424/133.1 |
| 2010/0204445 A1 | 8/2010 | Ishikawa et al. | |
| 2011/0129876 A1* | 6/2011 | Fierobe et al. | 435/69.52 |
| 2011/0151538 A1* | 6/2011 | Bayer et al. | 435/188 |
| 2012/0301930 A1* | 11/2012 | Bayer et al. | 435/99 |

FOREIGN PATENT DOCUMENTS

| | | |
|---|---|---|
| WO | WO 2009/028531 A1 | 3/2009 |
| WO | WO 2010/016067 A2 | 2/2010 |

OTHER PUBLICATIONS

Schimming, S., et al., 1992, "Structure of the Clostridium thermocellum gene licB and the encoded beta-1,3-1,4-glucanase. A catalytic region homologous to Bacillus lichenases joined to the reiterated domain of clostridial cellulases", European Journal of Biochemistry, vol. 204, pp. 13-19.*

Ding, S.-Y., et al., 2003, "The bacterial scaffoldin: Structure, function and potential applictions in the nanosciences", Genetic Engineering, vol. 25, pp. 209-225.*

Adams, J. J., et al., 2005, "Structural Characterization of Type II Dockerin Module from the Cellulosome of Clostridium thermocellum: Calcium-Induced Effects on Conformation and Target Recognition",Biochemistry, vol. 44, pp. 2173-2182.*

Fierobe, H.-P., et al., 2005, "Action of Designer Cellulosomes on Homogeneous Versus Complex Substrates: Controlled Incorporation of Three Distinct Enzymes Into a Defined Trifunctional Scaffoldin", The Journal of Biological Chemistry, vol. 280, No. 16, pp. 16325-16334.*

Haimovitz, R., et al., 2008, "Cohesin-dockerin microarray: Diverse specificities between two complementary families of interacting protein modules", Proteomics, vol. 8, pp. 968-979.K.*

Kamezaki, Y., et al., 2010, "The Dock tag, an affinity tool for the purification of recombinant proteins, based on the interaction between dockerin and cohesin domains from Clostridium josui cellulosome", Protein Expression and Purification, vol. 70, pp. 23-31.*

Sakka, K., et al., 2011, "Analysis of cohesin-dockerin interactions using mutant dockerin proteins", FEMS Microbiology Letters, vol. 314, pp. 75-80.*

Wang, W. K., et al., 1993, "Cloning and DNA sequence of the gene coding for Clostridium thermocellum cellulase Ss (CelS), a major cellulosome component", Journal of Bacteriology, vol. 175, pp. 1293-1302.*

Karpol, A., et al., 2008, Functional asymmetry in cohesin binding belies inherent symmetry of the dockerin module: insight into cellulosome assembly revealed by systematic mutagenesis, Biochemical Journal, vol. 410, pp. 331-338.*

Knapp, K.M., et al., 2012, "Crystallization and preliminary x-ray analysis of the open form of human ecto-5'-nucleotidase (CD73)", Acta Crystallographica, Section F: Structural Biology and Crystallization Communications, vol. 68, No. 12, pp. 1545-1549.*

Jun. 12, 2012 Office Action issued in Japanese Patent Application No. 2008-198497 (with translation).

Bayer, Edward et al., "The cellulosome—a treasure-trove for biotechnology", Trends Biotechnol., 1994, 12 [9], pp. 379-386.

Ohmiya, Kunio, "Analysis of a Nano Arrangement of Cellulase Complex and Construction of an Artificial Enzyme Complex for Converting $CO_2$ to Methanol," Wave Mie University, 2004, [30], pp. 13-14 (with translation).

Perret et al., "Use of antisense RNA to modify the composition of cellulosomes produced by Clostridium cellulolyticum," Molecular Microbiology, 2004, vol. 51, No. 2, pp. 599-607, Blackwell Publishing Ltd., France.

Desvaux, "The cellulosome of Clostridium cellulolyticum," Enzyme and Microbial Technology, 2005, vol. 37, pp. 373-385, Elsevier Inc.

Pages, et al., "Sequence Analysis of Scaffolding Protein CipC and ORFXp, a New Cohesin-Containing Protein in Clostridium cellulolyticum: Comparison of Various Cohesin Domains and Subcellular Localization of ORFXp," Journal of Bacteriology, 1999, vol. 181, No. 6, pp. 1801-1810, American Society for Microbiology, United States.

Office Action issued in U.S. Appl. No. 12/219,911 dated Jan. 27, 2012.

Feb. 26, 2013 Office Action issued in Japanese Patent Application No. 2010-088952; with translation.

Karpol et al., "Functional asymmetry in cohesin binding belies inherent symmetry of the dockerin module: insight into cellulosome assembly revealed by systematic mutagenesis," Biochem. J., 2008, pp. 331-338, vol. 410, Great Britain.

Carvalho et al.,"Evidence for a dual binding mode of dockerin modules to cohesins," PNAS, 2007, pp. 3089-3094, vol. 104, No. 9.

Mechaly et al., "Cohesin-Dockerin Interaction in Cellulosome Assembly," The Journal of Biological Chemistry, 2001, pp. 9883-9888, vol. 276, No. 13, United States.

Perret et al., "Production of Heterologous and Chimeric Scaffoldins by Clostridium acetobutylicum ATCC 824," Journal of Bacteriology, 2004, pp. 253-257, vol. 186, No. 1.

Ito et al., "Development of Immobilization Method for Protein to Cell Surface of Yeast via Binding Between Proteins," SCE 71$^{st}$ Annual Meeting, 2006, Tokyo, Japan (with English-language translation).

U.S. Appl. No. 12/219,911, filed Jul. 30, 2008 in the name of Kohda et al.

Arnold L. Demain et al., "Cellulase, Clostridia, and Ethanol," Microbiology and Molecular Biology Reviews, 2005, pp. 124-154 vol. 69-1.

Roy H. Doi et al., "Cellulosomes from Mesophilic Bacteria," Journal of Bacteriology, 2003, pp. 5907-5914, vol. 185-20.

Apr. 3, 2012 Japanese Office Action issued in Japanese Application No. 2010-088952 (with partial English-language Translation).

Japanese Society of Enzyme Engineering Meeting Proceeding, pp. 62, C-1, 2005.

Tal Handelsman et al., "Cohesin-dockerin interaction in cellulosome assembly: a single Asp-to-Asn mutation disrupts high-affinity cohesion-dockerin binding," FEBS Letters, 572, 2004, pp. 195-200.

Annette Herscovics et al., "Glycoprotein Biosynthesis in Yeast," FASEB, 7, pp. 540-550, 1993.

Protein, Nucleic Acid and Enzyme (PNE), 44(10), pp. 1487-1496, 1999.

Jun. 4, 2013 Office Action issued in Japanese Patent Application No. 2012-212947 (with partial English translation).

Jul. 1, 2014 Office Action issued in Japanese Patent Application No. 2010-088952 (with translation).

Ichinose, Hitomi, et al., 2006, "Characterization of an Exo-β-1,3-Galactanase from Clostridium thermocellum", Applied and Environmental Microbiology, vol. 72, No. 5, pp. 3515-3523.

* cited by examiner

FIG. 3A

Cel 48S Docherin

GTPSTKLYGD VNDDGKVNST DAVALKRYVL
RSGISINTDN ADLNEDGRVN STDLGILKRY
ILKEIDTLPY KN

Replace N to A or D

FIG. 3B

```
48Sdock-N18A-Fw  ctcgagcGGTACTCCTTCTACTAAATTATACGGGACGTCAATGATGACGGAAAAGTTGCT →A
48Sdock-N18D-Fw  ctcgagcGGTACTCCTTCTACTAAATTATACGGGACGTCAATGATGACGGAAAAGTTGAT →D ctcgagcGGTACTCCTTCTACTAAATTATACGGGACGTCAATGATGACGGAAAAGTTAAC
                  G  T  P  S  T  K  L  Y  G  D  V  N  D  D  G  K  V  N TCAACTGACG
                 TCAACTGACG
                 TCAACTGACGGCTGTGAGCATTGAAGAGATATGTTTGAGATCAGGTATAAGCATCAACACT
                  S  T  D  A  V  A  L  K  R  Y  V  L  R  S  G  I  S  I  N  T
                                    A→ GCCGTCTCAACGAAGTGACTGAATCCTTAAAACTTC
                                    D→ GCCGTGTCAACTAAGTGACTGAATCCTTAAAACTTC
                 GACAATGCCGATTTGAATGAAGACGGACGAGTTAATTCAACTGACTTAGGAATTTTGAAG
                  D  N  A  D  L  N  E  D  G  R  V  N  S  T  D  L  G  I  L  K TCTATATAAGAGTTTCTTATCTATGTAACGCGGCATGTTCTTGATTcctagg   48Sdock-N50A-Rv
                 TCTATATAAGAGTTTCTTATCTATGTAACGGGCATGTTCTTGATTcctagg    48Sdock-N50D-Rv
                 AGATATATTCTCAAGAATAGATACATTGCCGTACAAGAACTAAggatcc
                  R  Y  I  L  K  E  I  D  T  L  P  Y  K  N  *
```

Co-express Ct CBD1coh and Dockerin and compare displayed amounts depending on the presence or absence of mutation to sugar ch

FIG. 6B

10Cdock-N18D-Fw
ctcgagcGAAACCGCCGGTTCAGGTTATACCCGGTGATGTAAACGGTGTCGTGTAGAT ⟵ D
        E  P  P  V  Q  V  I  P  G  D  V  N ctcgagcGAAACCGCCGGTTCAGGTTATACCCGGTGATGTAAACGGTGTCGTGTAAAT
        E  P  P  V  Q  V  I  P  G  D  V  N  G  D  G  R  V  N TCATCCGACT ⟶
TCATCCGACTTGACTCTTTATGAAAAGATACCTTTAAAATCCATAAGGCGACTTCCCGACA
S  S  D  L  T  L  M  K  R  Y  L  L  K  S  I  S  D  F  P  T GCCGTTCCATGTGTAAGCTGTCTA ⟵ D
CCGGAAGGAAAAATTGCGGGCGGATTTAAACGGAAGAGGCAAGGTAAACGGACGACAGAT
P  E  G  K  I  A  A  D  L  N  E  D  G  K  V  N  S  T  D
                                            10Cdock-N50D-Rv AACAATCGGCGACTCTCTTGAGCAAGACTCTCTTGAAACTCTTGAAAACTTTGAGgatcc
                              10Cdock-N50D-Rv TTGTTAGCGCTGAAAAAACTCGTTCTGAGAGAACTTTGAggatcc
L  L  A  L  K  K  L  V  L  R  E  L  *

Co-express Ct CBD1coh and Dockerin and compare displayed amounts depending on the presence or absence of mutation to sugar chain mod Co-express Ct CBD1coh and Dockerin type Cellulase and compare displayed amounts depending on the presence or absence of mutation to sugar chain modification site

PROTEIN FOR CONSTRUCTING PROTEIN COMPLEX FROM CLOSTRIDIUM THERMOCELLUM, AND USE THEREOF

CROSS-REFERENCE TO RELATED APPLICATION(S)

This application claims priority to Japanese Patent Application No. 2010-088952 filed on Apr. 7, 2010, the contents of which are hereby incorporated by reference into the present application.

TECHNICAL FIELD

The present application relates to a protein for constructing a protein complex from *Clostridium thermocellum*, and to a use thereof.

DESCRIPTION OF RELATED ART

In recent years there has been increased interest in biomass resources derived from plant photosynthesis as a substitute for limited petroleum supplies, and various attempts have been made to use biomass for energy and various kinds of materials. In order for biomass to be used effectively as an energy source or other raw material, it must be saccharified into a carbon source that is readily available to animals and microorganisms.

Using typical forms of biomass such as cellulose and hemicellulose requires good cellulases for saccharifying (decomposing) these materials. Attention has focused on cellulosomes, which are produced by certain bacteria, as a source of such cellulases. Cellulosomes are protein complexes formed on the cell surfaces of bacteria, and comprise cellulases and scaffolding proteins (scaffoldins) to which the cellulases bind. Scaffolding proteins have sites called cohesins, and cellulases are known to bind to these cohesins via their own dockerins. Cellulosomes are capable of providing a variety of cellulases in large quantities and at high densities on bacterial cell surfaces.

Artificial construction of cellulosomes by genetic engineering has been studied in recent years. In the context of cellulosome construction, various studies have been made of binding between cohesins and dockerins, which is the basis of cellulosome construction. For example, several amino acid residues have been deleted or alanine scanned from dockerins of *Clostridium thermocellum* to evaluate binding with cohesins and identify the residues necessary for binding ability (Non-patent Document 1). According to this document, a dockerin produced in *E. coli* maintains about 70% the amount of binding with a cohesin when asparagine in the amino acid sequence is replaced with alanine, but interactions with calcium ions contributing to structural stability are weakened. It has also been reported that when binding ability is eliminated by substituting AA (alanine-alanine) for ST (serine-threonine) in one of two repeating amino acid sequences making up two helixes in a dockerin of *C. thermocellum*, the other helix binds with a cohesin (Non-patent document 2). With respect to cohesins, when several amino acid residues of a cohesin of *C. thermocellum* were replaced and binding with dockerins was evaluated, it was found that binding with dockerins from *C. thermocellum* was eliminated by replacing certain threonines with leucine, and instead, the cohesin bound to a dockerin from *Clostridium cellulolyticum* with which it did not ordinarily interact (Non-patent Document 3).

[Non-patent Document 1] A. Karpol et al., Biochem. J 410, 331-338 (2008)
[Non-patent Document 2] A. L. Carvalho et al., PNAS 104(9), 3089-3094 (2007)
[Non-patent Document 3] A. Mechaly et al., J. Biol. Chem. 276 (13), 9883-9888 (2001)

BRIEF SUMMARY OF INVENTION

Causing a yeast or the like to produce and excrete large quantities of cellulase is considered as desirable when constructing an artificial cellulosome. If a cellulosome can be constructed on the cell surface of a yeast or other eukaryotic microorganism, the glucose decomposed by the cellulosome can be used immediately by the yeast as a carbon source for efficient production of various useful substances. However, when a foreign protein from a bacteria or other prokaryote is produced with a yeast or other eukaryote, interaction between proteins can be affected by giant sugar chain modification.

According to the reports above, it appears that amino acid substitution of dockerin domains affects cohesin-dockerin binding, either by reducing binding ability (Non-patent Documents 1, 2) or altering binding specificity (Non-patent Document 3). However, there have been no reports on improving cohesin-dockerin binding ability. Moreover, the reports above pertain only to cohesins and dockerins produced in *E. coli*, in which sugar chain modification of proteins does not occur. Thus, at present there are no reports at all on how amino acid substitution of dockerin domains affects cohesin-dockerin binding in yeasts and other eukaryotic microorganisms, in which sugar chain modification does occur.

It is an object of the disclosures of this Description to provide a protein having a dockerin, wherein the protein is useful for producing a protein complex derived from *Clostridium thermocellum* in a yeast or other eukaryotic microorganism in which sugar chain modification is expected, and provides excellent cohesin-dockerin binding ability, along with a use thereof.

In a search for dockerins of *C. thermocellum* using DDBJ (www.ddbj.nig.ac.jp/index-j.html), the inventors in this case discovered 72 attributed dockerins on the genome of *C. thermocellum*, and after using UniProt (www.uniprot.org) and the like to identify specific sequences thought to be associated with cohesin-dockerin binding in these dockerins, we analyzed these specific sequences by multiple alignment and the like. As a result, the similarity of these 142 specific sequences exceeded 90%. It is therefore thought that all these specific sequences have binding ability with cohesins.

The inventors also discovered that of these specific sequences, 113 or about 80% of the relevant sequences have predicted sugar chain modification sites, while the remaining 29 sequences lack predicted sugar chain modification sites. The inventors then targeted two predicted sugar chain binding sites located near the scaffolding protein binding region of a dockerin from *C. thermocellum*, replacing the asparagines at these sites with alanine or aspartic acid. Sugar chain modification was eliminated by replacing asparagine with alanine in the dockerin, but cohesin binding ability was not improved. It is possible that the dockerin with asparagine replaced with alanine could not bind with cohesin because it does not assume a stable structure when produced in yeast. On the other hand, when a dockerin having the asparagine of the target site replaced with aspartic acid was produced in yeast, however, cohesin-dockerin binding increased, resulting in improved yeast saccharification ability.

From this, it was found that cohesin-dockerin binding ability can be increased and saccharification ability in eukaryotes in which sugar chain modification may occur can be improved if either predicted sugar chain modification sites are inherently lacking, or if when such a site is present, and an asparagine at the predicted site is replaced with aspartic acid to eliminate sugar chain modification, thereby improving cohesin-dockerin binding ability.

The disclosures of this description provide a protein for constructing a protein complex using a framework including a type I cohesin from *C. thermocellum*, wherein the protein has a dockerin containing at least one dockerin-specific sequence associated with cohesin binding in type I dockerins from *C. thermocellum*, and this dockerin satisfies either of the following conditions (a) and (b):

(a) having no intrinsic predicted N-type sugar chain modification site;

(b) having aspartic acid substituted for an asparagine of an intrinsic predicted N-type sugar chain modification site.

In a dockerin-specific sequence satisfying condition (a) above, the intrinsic predicted N-type sugar chain modification site may be an aspartic acid.

The protein disclosed in this Description may also have cellulolysis promotion activity, and this cellulolysis promotion activity may be cellulase activity. The cellulolysis promotion activity may also be conferred by an amino acid sequence from *Clostridium thermocellum*.

The disclosures of this Description provide a eukaryotic microorganism having a protein complex using a scaffolding protein from *Clostridium thermocellum* in the cell surface, wherein the eukaryotic microorganism is provided with a scaffolding protein from *Clostridium thermocellum* and the protein disclosed in this description, which binds with this scaffolding protein.

The disclosures of this Description provide a method for producing a useful substance, having a step of saccharifying a cellulose-containing material using a process of fermenting a cellulose-containing material as a carbon source with the eukaryotic microorganism disclosed in this Description, which is a eukaryotic microorganism in which the aforementioned dockerin protein has cellulolysis promotion activity.

BRIEF DESCRIPTION OF DRAWINGS

FIG. 3 shows an amino acid sequence having alanine or aspartic acid substituted for the No. 18 and No. 50 asparagines in the amino acid sequence of a Cel48S dockerin gene, and the corresponding genetic sequence.

DETAILED DESCRIPTION OF INVENTION

Figure 1:
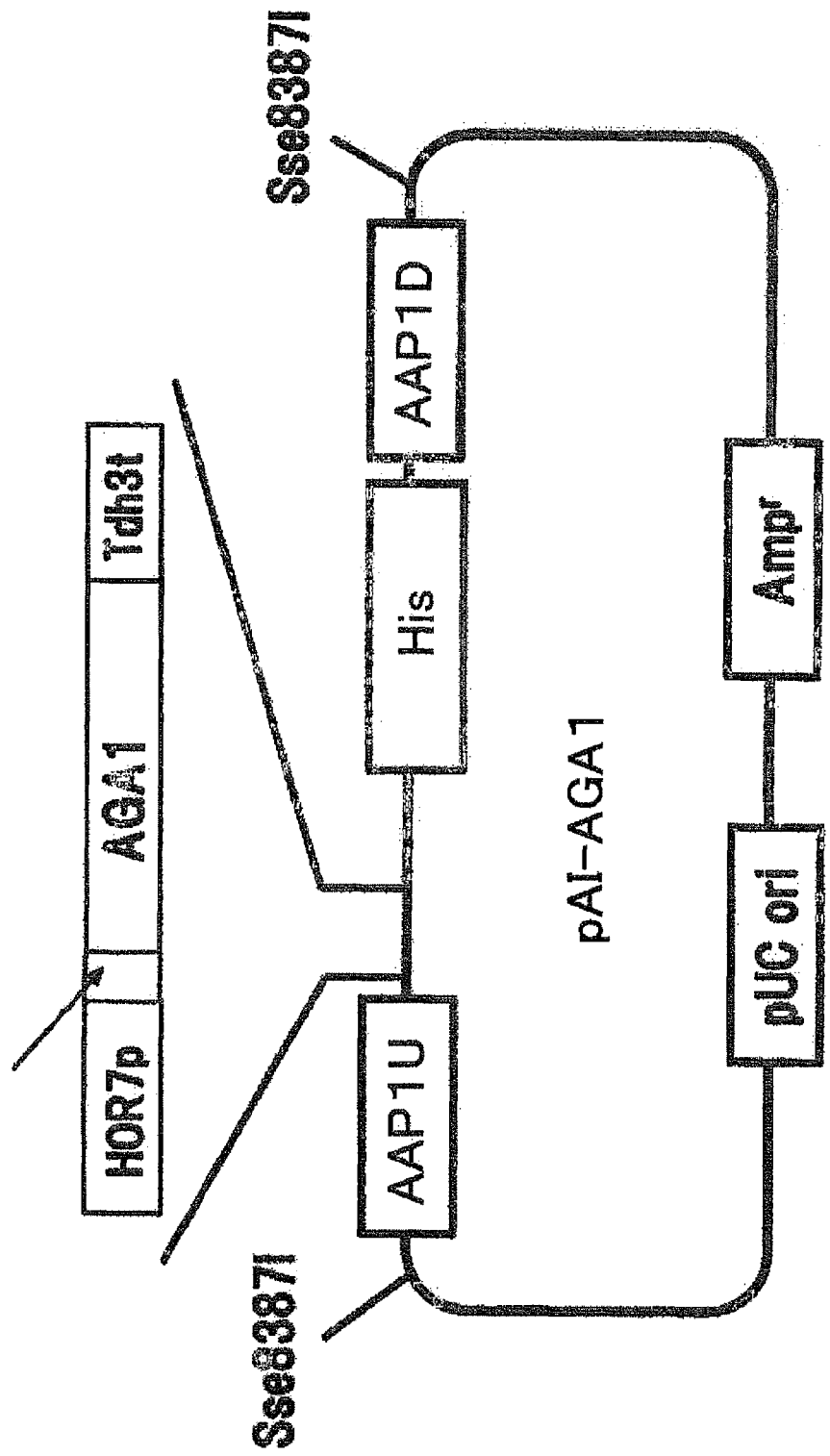
FIG. 1 shows a pAI-AGA1 vector prepared in Example 1.

The disclosures of this Description relate to a protein for constructing a protein complex using a scaffolding protein having type I cohesin from *C. thermocellum*, to a eukaryotic microorganism provided with a protein complex comprising this protein, and to a method for producing a useful substance using this eukaryotic microorganism.

The protein disclosed in this description has at least one dockerin-specific sequence which is a sequence associated with cohesin binding ability in a type I dockerin from *C. thermocellum*, and which either has no intrinsic predicted N-type sugar chain modification site or has aspartic acid substituted for asparagine at an intrinsic predicted N-type sugar chain modification site. Sugar chain modification is thus eliminated even if the protein disclosed in this Description is produced in a yeast or other eukaryotic microorganism in which sugar chain modification is expected to occur. As a result, the protein disclosed in this Description has excellent binding ability with type I cohesins of scaffolding proteins from *C. thermocellum*, and can be used to construct a protein complex in which this protein is bound densely and/or in large amounts.

The eukaryotic microorganism disclosed in this description may be provided in the cell surface with a protein complex in which the protein disclosed in this Description is accumulated densely and/or in large amounts. It is thus possible to obtain a eukaryotic microorganism in which the function of the protein of the invention is enhanced. Because the protein of the invention has excellent cohesin binding ability even when produced in a eukaryotic microorganism, this protein and the aforementioned scaffolding protein may both be produced by the eukaryotic microorganism disclosed in this Description. This eukaryotic microorganism may be a yeast.

The method of producing a useful substance disclosed in this Description comprises a step of fermenting a cellulose-containing material as a carbon source using the eukaryotic microorganism disclosed in this Description, in which the aforementioned protein is a protein having cellulolysis promotion activity. Because the eukaryotic microorganism disclosed in this Description has enhanced cellulolysis promotion activity, it can efficiently ferment a cellulose-containing material as a carbon source.

(Protein for Constructing Protein Complex Using Scaffolding Protein Having Type 1 Cohesin from *C. Thermocellum*)

The protein disclosed in this Description is a protein especially suited to constructing a protein complex using a scaffolding protein having a type I cohesin from *C. thermocellum*. This protein may have a dockerin comprising at least one dockerin-specific sequence that is associated with cohesin binding in a type I dockerin from *C. thermocellulum*, and that fulfills the condition of either (a) having no intrinsic predicted N-type sugar chain modification site or (b) having aspartic acid substituted for an asparagine of an intrinsic predicted N-type sugar chain modification site.

*C. thermocellum* is known as a cellulosome-producing microorganism. *C. thermocellum* also has cellulase activity, and produces proteins containing type I dockerins. Based on the results of a search of the *C. thermocellum* genome in DDBJ (www.ddbj.nig.ac.jp/index-j.html), the 72 amino acid sequences shown by Seq. Nos. 1 to 72 in Table 1 below can be given as examples of type I dockerin amino acid sequences from *C. thermocellum*. The locus (sequence) names shown in Table 1 are the names of each dockerin. Thus, the amino acid sequences specified by dockerin names in the locus column of Tables 2 to 21 derive from the amino acid sequences of dockerins having the same name in Table 1.

TABLE 1

| SEQ ID NO: | locus (SEQ. Name) | Amino Acid Sequence |
|---|---|---|
| 1 | Cthe0015 | DVNADGKDSTDLTLLKRYLLRSATLEEKLNADTDGNGTVNSTDLNYLKKYLRVI |
| 2 | Cthe0032 | DLNNDGNNSTDYMLKKYLKVLERMNVPEKAADLNGDGSINSTDLTLKRFIMKAI |
| 3 | Cthe0043 | DLNGDGNNSTDFTMLKRAILGNPAPGTNLAAGDLNRDGNTNSTDLMLRRYLLKLI |
| 4 | Cthe0044 | DNLDGKINSTDLSALKRHILRITTLSGKQLENADVNNDGSVNSTDASILKKYAKAI |
| 5 | Cthe0109 | DFNSDSSVNSTDLMILNRAVLGLG |
| 6 | Cthe0190 | ELNGDGKNSSDLNMMKRYLLRLIDGLNDTACADLNGDGKNSSDYSLKRYLLRMI |
| 7 | Cthe0191 | DLNGDAKINSTDLNMMKRYLLQMIDRFGVDDESCADLNGDGKITSSDYNLLKRYILHLI |
| 8 | Cthe0211 | DVNGDGHVNSSDYSLFKRYLLRVIDRFPVGDQSVADVNRDGRDSTDLTMLKRYLRAI |
| 9 | Cthe0239 | GDYNGDGAVNSTDLLACKRYLLYALKPEQNVIAGDLDGNGKINSTDYAYLKRYLLKQI |
| 10 | Cthe0246 | DLNADGKNSTDYNLGKRLILRTISELPISNGSVAFDLNGDSKVDSTDLTALKRYLLGVI |
| 11 | Cthe0258 | DVNGDSKNADVLLMKKYILKVINDLPSDGVKAADVNADGQINSDFTWLKKYMLKAV |
| 12 | Cthe0269 | DVNGDGNVNSTDLTMLKRYLLKSVTNINREAADVNRDGAINSSDMTILKRYLIKSI |
| 13 | Cthe0270 | DLNGDGKVNSSDLAILKRYMLRAISDFPIPEGRKLADLNRDGNVNSTDYSILKRYILKAI |
| 14 | Cthe0274 | CDVGDLNVDGSINSVDITYMKRYLLRSISVLPYQENERIRIPAADTNGDGAINSSDMVLLKRYVLRSI |
| 15 | Cthe0405 | DVNGDGNVNSTDVVWLRRFLLKLVEDFPVPSGKQAADMNDDGNINSTDMIALKRKVLKIP |
| 16 | Cthe0412 | DCNGDGKVNSTDAVALKRYILRSGISINTDNADVNADGRVNSTDLAILKRYLKEI |
| 17 | Cthe0413 | DCNDDGKVNSTDVAVMKRYLKKENVNINLDNADVNADGKVNSTDFSILKRYYMKNI |
| 18 | Cthe0433 | DLNGDGRVNSSDLALMKRYVVKQIEKLNVPVKAADLNGDDKVNSTDYSVLKRYLLRSI |
| 19 | Cthe0435 | DVNADGVVNISDYVLMKRYILRIIADFPADDDMWVGDVNGDNVINDIDCNYLKRYLLHMI |
| 20 | Cthe0438 | DLNGDNNINSSDYTLLKRYLLHTI |
| 21 | Cthe0536 | DVNGDGRVNSSDVALLKRYLLGLVENINKEAADVNVSGTVNSTDLAIMKRYVLRSI |
| 22 | Cthe0543 | DVNFDGRINSTDYSRLKRYVIKSLEFTDPEEHQKFIAAADVDGNGRINSTDLYVLNRYILKLI |
| 23 | Cthe0578 | DNLDGKINSSDVTLLKRYIVKSIDVFPTADPERSLIASDVNGDGRVNSTDYSYLKRYVLKII |
| 24 | Cthe0640 | DLNGDNNVNSTDLTLLKRYLTRVINDFPHPDGSVNADVNGDGKINSTDYSAMRIYILRII |
| 25 | Cthe0661 | DVNGDLKVNSTDFSMLRRYLLKTIDNFPTENGKQAADLNGDGRINSSDLTMLKRYLLMEV |
| 26 | Cthe0624 | DLNNDSKVNAVDIMMLKRYILGIIDNINLTADIYFDGVVNSSDYNIMKRYLLKAI |
| 27 | Cthe0625 | DLNGDGVVNSTDSVILKRHIIKFSEITDPVKLKAADLNGDGNINSSDVSLMKRYLLRII |
| 28 | Cthe0660 | DLNGDGKINSTDISLMKRYLLKQIVDLPVEDDIKAADINKDGKVNSTDMSILKRVILRNY |
| 29 | Cthe0729 | DSNSDCKVNSTDLTLMKRYLLQQSISYINLINADLNGDGKINSSDYTLLKRYLLGYI |
| 30 | Cthe0745 | DINNDKTVNSTDVTYLKRFLLKQINSLPNQKAADVNLDGNINSTDLVILKRYVLRGI |
| 31 | Cthe0797 | DVNGDGKINSTDCTMLKRYILRGIEEFPSPSGIIAADVNADLKINSTDLVLMKKYLLRSI |
| 32 | Cthe0798 | DVNLDGQVNSTDFSLLKRYILKVVDNSINVTNADMNINDGNNSTDISILKRILLRN |
| 33 | Cthe0821 | DINRDGKINSTDLGMLNRHILKLVILDDNLKLAAADIDGNGNINSTDYSWLKKYILKVI |
| 34 | Cthe0825 | DVNDDGKVNSTDLTLLKRYVLKAVSTLPSSKAEKNADVNRDGRVNSSDVTILSRYLIRVI |

TABLE 1-continued

| SEQ ID NO: | locus (SEQ. Name) | Amino Acid Sequence |
|---|---|---|
| 35 | Cthe0912 | DVNGDGTINSTDLTMLKRSVLRAITLTDDAKARADVDKNGSINSTDVLLLSRYLLRVI |
| 36 | Cthe0918 | DLNRNGIVNDEDYILLKNYLRGNKLVIDLNVADVNKDGKVNSTDCLFLKKYLGLI |
| 37 | Cthe1271 | DTNSDGKINSTDVTALKRHLLRVTQLTGDNLANADVNGDGVNSTDLLLLKRYILGEI |
| 38 | Cthe1398 | DLNGDNRINSTDLTLMKRYILKSIEDLPVEDDLWAADINGDGKINSTDYTYLKKYLLQAI |
| 39 | Cthe1400 | DLNGDGRVNSTDYTLLKRYLLGAIQTFPYERGIKAADLNLDGRINSTDYTVLKRYLLNAI |
| 40 | Cthe1472 | DLNFDNVAVNSTDLLMLKRYILKSLELGTSEQEEKFKKAADLNRDNKVDSTDLTILKRYLLKAI |
| 41 | Cthe1806 | EVIDTKVIDSTDDIVKYEYQFDKKILCADKETEILYFTVVADEEEIYTSDNTRTLVLSVNNDSTDKTTVSGYISVDF |
| 42 | Cthe1838 | DVNGDGRVNSSDLTLMKRYLLKSISDFPTPEGKIAADLNEDGKVNSTDLLALKKLVLREL |
| 43 | Cthe1890 | DLNADGSINSTDLMIMKRVLLKQRTLDDITPADLNGDGKVTSTDYSLMKRYLLKEI |
| 44 | Cthe1963 | DLNGDGNINSSDLQALKRHLLGISPLTGEALLRADVNRSGKVDSTDYSVLKRYILRII |
| 45 | Cthe2038 | DIVLDGNINSLDMMKLKKYLIRETQFNYDELLRADVNSDGEVNSTDYAYLKRYILRII |
| 46 | Cthe2089 | DVNDDGKVNSTDAVALKRYVLRSGISINTDNADLNEDGRVNSTDLGILKRYILKEI |
| 47 | Cthe2137 | DVDGNGTVNSTDVNYMKRYLLRQIEEFPYEKALMAGDVDGNGNINSTDLSYLKKYILKLI |
| 48 | Cthe2139 | DVNAGVINSSDIMVLKRFLLRTITLTEEMLLNADTNGDGAVNSSDFTLLKRYILRSI |
| 49 | Cthe2147 | DVNGDFAVNSNDLTLIKRYVLKNIDEFPSSHGLKAADVDGDEKITSSDAALVKRYVLRAI |
| 50 | Cthe2179 | DLNGDGNVNSTDSILMKRYLMKSVDLNEEQLKAADVNLDGRVNSTDRSILNRYLLKII |
| 51 | Cthe2193 | DINDDGNINSTDLQMLKRHLLRSIRLTEKQLLNADTNRDGRVDSTDLALLKRYILRVI |
| 52 | Cthe2194 | DLNGDGNINSTDLQILKKHLLRITLLTGKELSNADVTKDGKVDSTDLTLLKRYILRFV |
| 53 | Cthe2195 | DLNDDGKVNSTDFQILKKHLLRITLLTGKNLSNADLNKDGKVDSSDLSLMKRYLLQII |
| 54 | Cthe2196 | DLNNDGKVNSTDFQLLKMHVLRQELPAGTDLSNADVNRDGKVDSSDCTLLKRYILRVI |
| 55 | Cthe2197 | DLNGDGKVNSTDLQLMKMHVLRQRQLTGTSLLNADVNRDGKVDSTDVALLKRYILRQI |
| 56 | Cthe2271 | DVNLDGSVDSIDLALLYNTTYYAVPLPNRLQYIAADVNYDSSCTMLDFYMLEDYLLGRIS SFPAGQTYTVYYGDLNGDQLVTTDQSLLGRINLTFRQYVSADVNGDGTVNGDGTVDGIDLAIITAYINGQI |
| 57 | Cthe2360 | DLNGDGRVNSTDLLLMKKRIIREIDKFNVPDENADLNLDGKINSSDYTILKRYVLKSI |
| 58 | Cthe2549 | DVNKDGRINSTDIMYLKGYLLRNSAFNLDEYGLMAADVDGNGSVSSLDLTYLKRYILRRI |
| 59 | Cthe2590 | DLNQDGQVSSTDLVAMKRYLLKNFELSGVGLEAADLNSDGKVNSTDLVALKRFLLKEI |
| 60 | Cthe2760 | DLNYDGKVNSTDYLVLKRYLLGTIDKESDPNFLKAADLNRDGRVNSTDMSLMKRYLLGII |
| 61 | Cthe2761 | DVNGDGKVNSTDCSIVKRYLLKNIEDFPYEYGKEAGDVNGDGKVNSTDYSLLKRFVLRNI |
| 62 | CthE2811 | DLNGDGKVNSTDLTIMKRYILKNFDKLAVPEEAADLNGDGRINSTDLSILHRYLLRII |
| 63 | Cthe2812 | DLNGDQKVTSTDYTMLKRYLMKSIDRFNTSEQAADLNRDGKINSTDLTILKR |
| 64 | Cthe2872 | DINSDGNVNSTDLGILKRIIVKNPPASANMDAADVNADGKVNSTDYTVLKRYLLRSI |
| 65 | Cthe2879 | DINSDGSINSTDVTLLKRHLLRENILTGTAYSNADTDGDGKITSIDLSYLKRYVLRLI |
| 66 | Cthe2949 | DLNGDGLVNSSDYSLLKRYILKQIDLTEEKLKAADLNRNGSVDSVDYSILKRFLLKTI |
| 67 | Cthe2950 | DLNNDGRTNSTDYSLMKRYLLGSISFTNEQLKAADVNLDGKVNSSDYTVLRRFLLGSI |
| 68 | Cthe2972 | VLGDLNGDKQVNSTDYTALKRHLLNITRLSGTALANADLNGDGKVDSTDLMILHRYLLGII |
| 69 | Cthe3012 | DLNGDGNVNSTDSTLMSRYLLGIITTLPAGEKAADLNGDGKVNSTDYNILKRYLLKYI |
| 70 | Cthe3132 | DLNGDGRVNSTDLAVMKRYLLKQVQISDIRPADLNGDGKANSTDYQLLKRYILKTI |

TABLE 1-continued

| SEQ ID NO: | locus (SEQ. Name) | Amino Acid Sequence |
|---|---|---|
| 71 | Cthe3136 | DDGNGEISSIDYAILKSHLINSNLTFKQLAAADVDGNGYVNSIDLAILQMYLLGKGGTSDI |
| 72 | Cthe3141 | DVNGNGSIESTDCVWVKRYLLKQIDSFPNENGARAADVNGNGTIDSTDYQLLKRFILKVI |

Similar amino acid sequences that are dockerin-specific sequences associated with cohesin binding can be discovered in these 72 type I dockerins. A dockerin-specific sequence may consist of a naturally-derived consensus sequence (relevant sequence) consisting of 24 amino acids. The total of 142 amino acid sequences shown by SEQ ID NOS. 73 to 214 in Table 2 below can be given as examples of relevant sequences intrinsic to the 72 type I dockerins. These amino acid sequences can be obtained from databases such as UniProt (www.uniprot.org), InterPro (www.ebi.ac.uk/interpro) and Pfam (pfam.sanger.ac.uk). N-terminal relevant sequences are described in the 1st column of Table 2, while C-terminal relevant sequences are described in the 2nd column.

TABLE 2

| SEQ ID NO: | locus (SEQ Name) | - | Related Sequence |
|---|---|---|---|
| 73 | Cthe0015 | 1st | DVNADGKIDSTDLTLLKRYLLRSA |
| 74 | | 2nd | DTDGNGTVNSTDLNYLKKYILRVI |
| 75 | Cthe0032 | 1st | DLNNDGNINSTDYMILKKYILKVL |
| 76 | | 2nd | DLNGDGSINSTDLTILKRFIMKAI |
| 77 | Cthe0043 | 1st | DLNGDGNINSTDFTMLKRAILGNP |
| 78 | | 2nd | DLNRDGNTNSTDLMILRRYLLKLI |
| 79 | Cthe0044 | 1st | DINLDGKINSTDLSALKRHILRIT |
| 80 | | 2nd | DVNNDGSVNSTDASILKKYIAKAI |
| 81 | Cthe0109 | 1st | DFNSDSSVNSTDLMILNRAVLGLG |
| | | 2nd | |
| 82 | Cthe0190 | 1st | ELNGDGKINSSDLNMMKRYLLRLI |
| 83 | | 2nd | DLNGDGKINSSDYSILKRYLLRMI |
| 84 | Cthe0191 | 1st | DLNGDAKINSTDLNMMKRYLLQMI |
| 85 | | 2nd | DLNGDGKISSDYNLLKRYILHLI |
| 86 | Cthe0211 | 1st | DVNGDGHVNSSDYSLFKRYLLRVI |
| 87 | | 2nd | DVNRDGRIDSTDLTMLKRYLIRAI |
| 88 | Cthe0239 | 1st | DYNGDGAVNSTDLLACKRYLLYAL |
| 89 | | 2nd | DLDGNGKINSTDYAYLKRYLLKQI |
| 90 | Cthe0246 | 1st | DLNADGKINSTDYNLGKRLILRTI |
| 91 | | 2nd | DLNGDSKVDSTDLTALKRYLLGVI |
| 92 | Cthe0258 | 1st | DVNGDSKINAIDVLLMKKYILKVI |
| 93 | | 2nd | DVNADGQINSIDFTWLKKYMLKAV |
| 94 | Cthe0269 | 1st | DVNGDGNVNSTDLTMLKRYLLKSV |
| 95 | | 2nd | DVNRDGAINSSDMTILKRYLIKSI |
| 96 | Cthe0270 | 1st | DLNGDKVNSSDLAILKRYMLRAI |
| 97 | | 2nd | DLNRDGNVNSTDYSILKRYILKAI |
| 98 | Cthe0274 | 1st | DLNVDGSINSVDITYMKRYLLRSI |
| 99 | | 2nd | DTNGDGAINSSDMVLLKRYLVRSI |
| 100 | Cthe0405 | 1st | DVNGDGNVNSTDVVWLRRFLLKLV |
| 101 | | 2nd | DMNDDGNINSTDMIALKRKVLKIP |
| 102 | Cthe0412 | 1st | DCNGDGKVNSTDAVALKRYILRSG |
| 103 | | 2nd | DVNADGRVNSTDLAILKRYILKEI |
| 104 | Cthe0413 | 1st | DCNDDGKVNSTDVAVMKRYLKKEN |
| 105 | | 2nd | DVNADGKVNSTDFSILKRYVMKNI |
| 106 | Cthe0433 | 1st | DLNGDGRVNSSDLALMKRYVVKQI |
| 107 | | 2nd | DLNGDDKVNSTDYSVLKRYLLRSI |
| 108 | Cthe0435 | 1st | DVNADGVVNISDYVLMKRYILRII |
| 109 | | 2nd | DVNGDNVINDIDCNYLKRYLLHMI |
| 110 | Cthe0438 | 1st | DLNGDNNINSSDYTLLKRYLLHTI |
| | | 2nd | |
| 111 | Cthe0536 | 1st | DVNGDGRVNSSDVALLKRYLLGLV |
| 112 | | 2nd | DVNVSGTVNSTDLAIMKRYVLRSI |
| 113 | Cthe0543 | 1st | DVNFDGRINSTDYSRLKRYVIKSL |
| 114 | | 2nd | DVDGNGRINSTDLYVLNRYILKLI |
| 115 | Cthe0578 | 1st | DINLDGKINSSDVTLLKRYIVKSI |
| 116 | | 2nd | DVNGDGRVNSTDYSYLKRYVLKII |
| 117 | Cthe0640 | 1st | DLNGDNNVNSTDLTLLKRYLTRVI |
| 118 | | 2nd | DVNGDGKINSTDYSAMRYILRII |
| 119 | Cthe0661 | 1st | DVNGDLKVNSTDFSMLRRYLLKTI |
| 120 | | 2nd | DLNGDGRINSSDLTMLKRYLLMEV |
| 121 | Cthe0624 | 1st | DLNNDSKVNAVDIMMLKRYILGII |
| 122 | | 2nd | DIYFDGVVNSSDYNIMKRYLLKAI |
| 123 | Cthe0625 | 1st | DLNGDGVVNSTDSVILKRHIIKFS |
| 124 | | 2nd | DLNGDGNINSSDVSLMKRYLLRII |
| 125 | Cthe0660 | 1st | DLNGDGKINSTDISLMKRYLLKQI |
| 126 | | 2nd | DINKDGKVNSTDMSILKRVILRNY |
| 127 | Cthe0729 | 1st | DSNSDCKVNSTDLTLMKRYLLQQS |
| 128 | | 2nd | DLNGDGKINSSDYTLLKRYLLGYI |
| 129 | Cthe0745 | 1st | DINNDKTVNSTDVTYLKRFLLKQI |
| 130 | | 2nd | DVNLDGNINSTDLVILKRYVLRGI |
| 131 | Cthe0797 | 1st | DVNGDGKINSTDCTMLKRYILRGI |
| 132 | | 2nd | DVNADLKINSTDLVLMKKYLLRSI |
| 133 | Cthe0798 | 1st | DVNLDGQVNSTDFSLLKRYLKVV |
| 134 | | 2nd | DMNNDGNINSTDISILKRILLRN |
| 135 | Cthe0821 | 1st | DINRDGKINSTDLGMLNRHILKLV |
| 136 | | 2nd | DIDGNGNINSTDYSWLKKYILKVI |
| 137 | Cthe0825 | 1st | DVNDDGKVNSTDLTLLKRYVLKAV |
| 138 | | 2nd | DVNRDGRVNSSDVTILSRYLIRVI |
| 139 | Cthe0912 | 1st | DVNGDGTINSTDLTMLKRSVLRAI |
| 140 | | 2nd | DVDKNGSINSTDVLLLSRYLLRVI |
| 141 | Cthe0918 | 1st | DLNRNGIVNDEDYILLKNYLLRGN |
| 142 | | 2nd | DVNKDGKVNSTDCLFLKKYILGLI |

TABLE 2-continued

| SEQ ID NO: | locus (SEQ Name) | - | Related Sequence |
|---|---|---|---|
| 143 | Cthe1271 | 1st | DTNSDGKINSTDVTALKRHLLRVT |
| 144 | | 2nd | DVNGDGNVNSTDLLLLKRYILGEI |
| 145 | Cthe1398 | 1st | DLNGDNRINSTDLTLMKRYILKSI |
| 146 | | 2nd | DINGDGKINSTDYTYLKKYLLQAI |
| 147 | Cthe1400 | 1st | DLNGDGRVNSTDYTLLKRYLLGAI |
| 148 | | 2nd | DLNLDGRINSTDYTVLKRYLLNAI |
| 149 | Cthe1472 | 1st | DLNFDNAVNSTDLLMLKRYILKSL |
| 150 | | 2nd | DLNRDNKVDSTDLTILKRYLLKAI |
| 151 | Cthe1806 | 1st | EVIDTKVIDSTDDIVKYEYQFDKK |
| 152 | | 2nd | TLVLSVNNDSTDKTTVSGYISVDF |
| 153 | Cthe1838 | 1st | DVNGDGRVNSSDLTLMKRYLLKSI |
| 154 | | 2nd | DLNEDGKVNSTDLLALKKLVLREL |
| 155 | Cthe1890 | 1st | DLNADGSINSTDLMIMKRVLLKQR |
| 156 | | 2nd | DLNGDGKVTSTDYSLMKRYLLKEI |
| 157 | Cthe1963 | 1st | DLNGDGNINSSDLQALKRHLLGIS |
| 158 | | 2nd | DVNRSGKVDSTDYSVLKRYILRII |
| 159 | Cthe2038 | 1st | DIVLDGNINSLDMMKLKKYLIRET |
| 160 | | 2nd | DVNSDGEVNSTDYAYLKRYILRII |
| 161 | Cthe2089 | 1st | DVNDDGKVNSTDAVALKRYVLRSG |
| 162 | | 2nd | DLNEDGRVNSTDLGILKRYILKEI |
| 163 | Cthe2137 | 1st | DVDGNGTVNSTDVNYMKRYLLRQI |
| 164 | | 2nd | DVDGNGNINSTDLSYLKKYILKLI |
| 165 | Cthe2139 | 1st | DVNADGVINSSDIMVLKRFLLRTI |
| 166 | | 2nd | DTNGDGAVNSSDFTLLKRVILRSI |
| 167 | Cthe2147 | 1st | DVNGDFAVNSNDLTLIKRYVLKNI |
| 168 | | 2nd | DVDGDEKITSSDAALVKRYVLRAI |
| 169 | Cthe2179 | 1st | DLNGDGNVNSTDSILMKRYLMKSV |
| 170 | | 2nd | DVNLDGRVNSTDRSILNRYLLKII |
| 171 | Cthe2193 | 1st | DINDDGNINSTDLQMLKRHLLRSI |
| 172 | | 2nd | DTNRDGRVDSTDLALLKRYILRVI |
| 173 | Cthe2194 | 1st | DLNGDGNINSTDLQILKKHLLRIT |
| 174 | | 2nd | DVTKDGKVDSTDLTLLKRYILRFV |
| 175 | Cthe2195 | 1st | DLNDDGKVNSTDFQILKKHLLRIT |
| 176 | | 2nd | DLNKDGKVDSSDLSLMKRYLLQII |
| 177 | Cthe2196 | 1st | DLNNDGKVNSTDFQLLKMHVLRQE |
| 178 | | 2nd | DVNRDGKVDSSDCTLLKRYILRVI |
| 179 | Cthe2197 | 1st | DLNGDGKVNSTDLQLMKMHVLRQR |
| 180 | | 2nd | DVNRDGKVDSTDVALLKRYILRQI |
| 181 | Cthe2271 | 1st | DVNLDGSVDSTDLALLYNTTYYAV |
| 182 | | 2nd | DVNGDGTVDGIDLAIITAYINGQI |
| 183 | Cthe2360 | 1st | DLNGDGRVNSTDLLLMKKRIIREI |
| 184 | | 2nd | DLNLDGKINSSDYTILKRVVLKSI |
| 185 | Cthe2549 | 1st | DVNKDGRINSTDIMYLKGVLLRNS |
| 186 | | 2nd | DVDGNGSVSSLDLTYLKRYILRRI |
| 187 | Cthe2590 | 1st | DLNQDGQVSSTDLVAMKRYLLKNF |
| 188 | | 2nd | DLNSDGKVNSTDLVALKRFLLKEI |
| 189 | Cthe2760 | 1st | DLNYDGKVNSTDYLVLKRYLLGTI |
| 190 | | 2nd | DLNRDGRVNSTDMSLMKRYLLGII |
| 191 | Cthe2761 | 1st | DVNGDGKVNSTDCSIVKRYLLKNI |
| 192 | | 2nd | DVNGDGKVNSTDYSLLKRFVLRNI |
| 193 | Cthe2811 | 1st | DLNGDGKVNSTDLTIMKRYILKNF |
| 194 | | 2nd | DLNGDGRINSTDLSILHRYLLRII |
| 195 | Cthe2812 | 1st | DLNGDQKVTSTDYTMLKRYLMKSI |
| 196 | | 2nd | DLNRDGKINSTDLTILKRYLLYSI |
| 197 | Cthe2872 | 1st | DINSDGNVNSTDLGILKRIIVKNP |
| 198 | | 2nd | DVNADGKVNSTDYTVLKRYLLRSI |
| 199 | Cthe2879 | 1st | DINSDGSINSTDVTLLKRHLLREN |
| 200 | | 2nd | DTDGDGKITSIDLSVLKRVVLRLI |
| 201 | Cthe2949 | 1st | DLNGDGLVNSSDYSLLKRYILKQI |
| 202 | | 2nd | DLNRNGSVDSVDYSILKRFLLKTI |
| 203 | Cthe2950 | 1st | DLNNDGRTNSTDYSLMKRYLLGSI |
| 204 | | 2nd | DVNLDGKVNSSDYTVLRRFLLGSI |
| 205 | Cthe2972 | 1st | DLNGDKQVNSTDYTALKRHLLNIT |
| 206 | | 2nd | DLNGDGKVDSTDLMILHRYLLGII |
| 207 | Cthe3012 | 1st | DLNGDGNVNSTDSTLMSRYLLGII |
| 208 | | 2nd | DLNGDGKVNSTDYNILKRYLLKVI |
| 209 | Cthe3132 | 1st | DLNGDGRVNSTDLAVMKRYLLKQV |
| 210 | | 2nd | DLNGDGKANSTDYQLLKRYILKTI |
| 211 | Cthe3136 | 1st | DIDGNGEISSIDYAILKSHLINSN |
| 212 | | 2nd | DVDGNGYVNSIDLAILQMYLLGKG |
| 213 | Cthe3141 | 1st | DVNGNGSIESTDCVWVKRYLLKQI |
| 214 | | 2nd | DVNGNGTIDSTDYQLLKRFILKVI |

While a homology search of the doekerins shown in Table 1 revealed that the "homology" among these amino acid sequences does not exceed 90%, there is 90% or more "similarity" among the relevant sequences shown in Table 2. This suggests that the dockerins shown in Table 1 all have similar functions. It is therefore presumed that the relevant sequences shown in Table 2 are responsible for these functions.

In the dockerins shown in Table 1 or in other words in the relevant sequences shown in Table 2, the predicted N-type sugar chain modification sites are known to be N positions in N-X-T or N-X-S (in which N is asparagine, X is an amino acid other than proline, T is threonine and S is serine), which are consensus sequences that undergo N-type sugar chain modification in yeasts and other eukaryotic microorganisms (A. Herscovics et al., The FASEB Journal (6): 540-550 (1993)). An N-X-T/S of a dockerin or its relevant sequence can be found by suitable application of one of the databases described above or the like. A site corresponding to a predicted N-type sugar chain modification site in a dockerin or its relevant sequence may also correspond to N even when the amino acid sequence does not include one of the aforementioned consensus sequences. A site corresponding to a predicted N-type sugar chain modification site may be discovered by comparing an amino acid sequence that may contain this site by multiple alignment with the amino acid sequence of a known dockerin or its relevant sequence. If the amino acid sequence of a relevant sequence consists of about 24 or fewer amino acids, the predicted N-type sugar chain modification site in a dockerin, or a site corresponding to such a site, is typically the 9$^{th}$ amino acid from the N terminal.

The protein of the invention preferably has a dockerin comprising at least one dockerin-specific sequence having no predicted N-type sugar chain modification site. It also preferably has at least one dockerin-specific sequence in which the amino acid of a site corresponding to a predicted N-type sugar chain modification site is aspartic acid (D). It is thought that N-type sugar chain modification by yeasts and other eukaryotic microorganisms is eliminated when there is no N-type sugar chain modification site or when a site corresponding to a predicted sugar chain modification site is occupied by aspartic acid. A dockerin-specific sequence in which a site corresponding to a predicted sugar chain modification site is occupied by aspartic acid may be intrinsic to the original dockerin, or may have a N-type sugar chain modification site at which aspartic acid (D) has been substituted for asparagine (N).

Examples of one embodiment of this dockerin-specific sequence include dockerin-specific sequences having aspartic acid substituted for asparagine in the dockerins disclosed in Table 1 and the relevant sequences in these dockerins disclosed in Table 2 when these have intrinsic predicted N-type sugar chain modification sites. It is sufficient that the protein of the invention have a dockerin containing at least one such dockerin-specific sequence. Examples of relevant sequences having candidate N→D substitution sites include the following 113 relevant sequences. Consequently, preferred dockerin-specific sequences are sequences in which D is substituted for N (N-X-T/S) in the relevant sequences below.

TABLE 3

| locus | | Amino Acid Sequence |
|---|---|---|
| Cthe0015 | 2nd | DTDGNGTVNSTDLNYLKKYILRVI (SEQ ID NO: 74) |
| Cthe0032 | 1st | DLNNDGNINSTDYMILKKYILKVL (SEQ ID NO: 75) |
| Cthe0032 | 2nd | DLNGDGSINSTDLTILKRFIMKAI (SEQ ID NO: 76) |
| Cthe0043 | 1st | DLNGDGNINSTDFTMLKRAILGNP (SEQ ID NO: 77) |
| Cthe0043 | 2nd | DLNRDGNTNSTDLMILRRYLLKLI (SEQ ID NO: 78) |
| Cthe0044 | 1st | DINLDGKINSTDLSALKRHILRIT (SEQ ID NO: 79) |
| Cthe0044 | 2nd | DVNNDGSVNSTDASILKKYIAKAI (SEQ ID NO: 80) |
| Cthe0109 | 1st | DFNSDSSVNSTDLMILNRAVLGLG (SEQ ID NO: 81) |
| Cthe0190 | 1st | ELNGDGKINSSDLNMMKRYLLRLI (SEQ ID NO: 82) |
| Cthe0190 | 2nd | DLNGDGKINSSDYSILKRYLLRMI (SEQ ID NO: 83) |
| Cthe0191 | 1st | DLNGDAKINSTDLNMMKRYLLQMI (SEQ ID NO: 84) |
| Cthe0211 | 1st | DVNGDGHVNSSDYSLFKRYLLRVI (SEQ ID NO: 86) |
| Cthe0239 | 1st | DYNGDGAVNSTDLLACKRYLLYAL (SEQ ID NO: 88) |
| Cthe0239 | 2nd | DLDGNGKINSTDYAYLKRYLLKQI (SEQ ID NO: 89) |
| Cthe0246 | 1st | DLNADGKINSTDYNLGKRLILRTI (SEQ ID NO: 90) |

TABLE 3-continued

| locus | | Amino Acid Sequence |
|---|---|---|
| Cthe0269 | 1st | DVNGDGNVNSTDLTMLKRYLLKSV (SEQ ID NO: 94) |
| Cthe0269 | 2nd | DVNRDGAINSSDMTILKRYLIKSI (SEQ ID NO: 95) |
| Cthe0270 | 1st | DLNGDGKVNSSDLAILKRYMLRAI (SEQ ID NO: 96) |
| Cthe0270 | 2nd | DLNRDGNVNSTDYSILKRYILKAI (SEQ ID NO: 97) |
| Cthe0274 | 2nd | DTNGDGAINSSDMVLLKRYVLRSI (SEQ ID NO: 99) |
| Cthe0405 | 1st | DVNGDGNVNSTDVVWLRRFLLKLV (SEQ ID NO: 100) |
| Cthe0405 | 2nd | DMNDDGNINSTDMIALKRKVLKIP (SEQ ID NO: 101) |
| Cthe0412 | 1st | DCNGDGKVNSTDAVALKRYILRSG (SEQ ID NO: 102) |
| Cthe0412 | 2nd | DVNADGRVNSTDLAILKRYILKEI (SEQ ID NO: 103) |
| Cthe0413 | 1st | DCNDDGKVNSTDVAVMKRYLKKEN (SEQ ID NO: 104) |
| Cthe0413 | 2nd | DVNADGKVNSTDFSILKRYVMKNI (SEQ ID NO: 105) |
| Cthe0433 | 1st | DLNGDGRVNSSDLALMKRYVVKQI (SEQ ID NO: 106) |
| Cthe0433 | 2nd | DLNGDDKVNSTDYSVLKRYLLRSI (SEQ ID NO: 107) |
| Cthe0435 | 1st | DVNADGVVNISDYVLMKRYILRII (SEQ ID NO: 108) |
| Cthe0438 | 1st | DLNGDNNINSSDYTLLKRYLLHTI (SEQ ID NO: 110) |
| Cthe0536 | 1st | DVNGDGRVNSSDVALLKRYLLGLV (SEQ ID NO: 111) |
| Cthe0536 | 2nd | DVNVSGTVNSTDLAIMKRYVLRSI (SEQ ID NO: 112) |
| Cthe0543 | 1st | DVNFDGRINSTDYSRLKRYVIKSL (SEQ ID NO: 113) |
| Cthe0543 | 2nd | DVDGNGRINSTDLYVLNRYILKLI (SEQ ID NO: 114) |
| Cthe0578 | 1st | DINLDGKINSSDVTLLKRYIVKSI (SEQ ID NO: 115) |
| Cthe0578 | 2nd | DVNGDGRVNSTDYSYLKRYVLKII (SEQ ID NO: 116) |
| Cthe0624 | 1st | DLNNDSKVNAVDIMMLKRYILGII (SEQ ID NO: 121) |
| Cthe0624 | 2nd | DIYFDGVVNSSDYNIMKRYLLKAI (SEQ ID NO: 122) |
| Cthe0625 | 1st | DLNGDGVVNSTDSVILKRHIIKFS (SEQ ID NO: 123) |
| Cthe0625 | 2nd | DLNGDGNINSSDVSLMKRYLLRII (SEQ ID NO: 124) |
| Cthe0640 | 1st | DLNGDNNVNSTDLTLLKRYLTRVI (SEQ ID NO: 117) |

TABLE 3-continued

| locus | | Amino Acid Sequence |
|---|---|---|
| Cthe0640 | 2nd | DVNGDGKINSTDYSAMIRYILRII (SEQ ID NO: 118) |
| Cthe0660 | 1st | DLNGDGKINSTDISLMKRYLLKQI (SEQ ID NO: 125) |
| Cthe0660 | 2nd | DINKDGKVNSTDMSILKRVILRNY (SEQ ID NO: 126) |
| Cthe0661 | 1st | DVNGDLKVNSTDFSMLRRYLLKTI (SEQ ID NO: 119) |
| Cthe0661 | 2nd | DLNGDGRINSSDLTMLKRYLLMEV (SEQ ID NO: 120) |
| Cthe0729 | 1st | DSNSDCKVNSTDLTLMKRYLLQQS (SEQ ID NO: 127) |
| Cthe0729 | 2nd | DLNGDGKINSSDYTLLKRYLLGYI (SEQ ID NO: 128) |
| Cthe0745 | 1st | DINNDKTVNSTDVTYLKRFLLKQI (SEQ ID NO: 129) |
| Cthe0745 | 2nd | DVNLDGNINSTDLVILKRYVLRGI (SEQ ID NO: 130) |
| Cthe0797 | 1st | DVNGDGKINSTDCTMLKRYILRGI (SEQ ID NO: 131) |
| Cthe0797 | 2nd | DVNADLKINSTDLVLMKKYLLRSI (SEQ ID NO: 132) |
| Cthe0798 | 1st | DVNLDGQVNSTDFSLLKRYILKVV (SEQ ID NO: 133) |
| Cthe0798 | 2nd | DMNNDGNINSTDISILKRILLRN (SEQ ID NO: 134) |
| Cthe0821 | 1st | DINRDGKINSTDLGMLNRHILKLV (SEQ ID NO: 135) |
| Cthe0821 | 2nd | DIDGNGNINSTDYSWLKKYILKVI (SEQ ID NO: 136) |
| Cthe0825 | 1st | DVNDDGKVNSTDLTLLKRYVLKAV (SEQ ID NO: 137) |
| Cthe0825 | 2nd | DVNRDGRVNSSDVTILSRYLIRVI (SEQ ID NO: 138) |
| Cthe0912 | 1st | DVNGDGTINSTDLTMLKRSVLRAI (SEQ ID NO: 139) |
| Cthe0912 | 2nd | DVDKNGSINSTDVLLLSRYLLRVI (SEQ ID NO: 140) |
| Cthe0918 | 2nd | DVNKDGKVNSTDCLFLKKYILGLI (SEQ ID NO: 142) |
| Cthe1271 | 1st | DTNSDGKINSTDVTALKRHLLRVT (SEQ ID NO: 143) |
| Cthe1271 | 2nd | DVNGDGNVNSTDLLLLKRYILGEI (SEQ ID NO: 144) |
| Cthe1398 | 1st | DLNGDNRINSTDLTLMKRYILKSI (SEQ ID NO: 145) |
| Cthe1398 | 2nd | DINGDGKINSTDYTYLKKYLLQAI (SEQ ID NO: 146) |
| Cthe1400 | 1st | DLNGDGRVNSTDYTLLKRYLLGAI (SEQ ID NO: 147) |
| Cthe1400 | 2nd | DLNLDGRINSTDYTVLKRYLLNAI (SEQ ID NO: 148) |
| Cthe1472 | 1st | DLNFDNAVNSTDLLMLKRYILKSL (SEQ ID NO: 149) |
| Cthe1806 | 2nd | TLVLSVNNDSTDKTTVSGYISVDF (SEQ ID NO: 152) |
| Cthe1838 | 1st | DVNGDGRVNSSDLTLMKRYLLKSI (SEQ ID NO: 153) |
| Cthe1838 | 2nd | DLNEDGKVNSTDLLALKKLVLREL (SEQ ID NO: 154) |
| Cthe1890 | 1st | DLNADGSINSTDLMIMKRVLLKQR (SEQ ID NO: 155) |
| Cthe1963 | 1st | DLNGDGNINSSDLQALKRHLLGIS (SEQ ID NO: 157) |
| Cthe1963 | 2nd | DVNRSGKVDSTDYSVLKRYILRII (SEQ ID NO: 158) |
| Cthe2038 | 2nd | DVNSDGEVNSTDYAYLKRYILRII (SEQ ID NO: 160) |
| Cthe2089 | 1st | DVNDDGKVNSTDAVALKRYVLRSG (SEQ ID NO: 161) |
| Cthe2089 | 2nd | DLNEDGRVNSTDLGILKRYILKEI (SEQ ID NO: 162) |
| Cthe2137 | 1st | DVDGNGTVNSTDVNYMKRYLLRQI (SEQ ID NO: 163) |
| Cthe2137 | 2nd | DVDGNGNINSTDLSYLKKYILKLI (SEQ ID NO: 164) |
| Cthe2139 | 1st | DVNADGVINSSDIMVLKRFLLRTI (SEQ ID NO: 165) |
| Cthe2139 | 2nd | DTNGDGAVNSSDFTLLKRYILRSI (SEQ ID NO: 166) |
| Cthe2179 | 1st | DLNGDGNVNSTDSILMKRYLMKSV (SEQ ID NO: 169) |
| Cthe2179 | 2nd | DVNLDGRVNSTDRSILNRYLLKII (SEQ ID NO: 170) |
| Cthe2193 | 1st | DINDDGNINSTDLQMLKRHLLRSI (SEQ ID NO: 171) |
| Cthe2194 | 1st | DLNGDGNINSTDLQILKKHLLRIT (SEQ ID NO: 173) |
| Cthe2195 | 1st | DLNDDGKVNSTDFQILKKHLLRIT (SEQ ID NO: 175) |
| Cthe2196 | 1st | DLNNDGKVNSTDFQLLKMHVLRQE (SEQ ID NO: 177) |
| Cthe2197 | 1st | DLNGDGKVNSTDLQLMKMHVLRQR (SEQ ID NO: 179) |
| Cthe2360 | 1st | DLNGDGRVNSTDLLLMKKRIIREI (SEQ ID NO: 183) |
| Cthe2360 | 2nd | DLNLDGKINSSDYTILKRYVLKSI (SEQ ID NO: 184) |
| Cthe2549 | 1st | DVNKDGRINSTDIMYLKGYLLRNS (SEQ ID NO: 185) |
| Cthe2590 | 2nd | DLNSDGKVNSTDLVALKRFLLKEI (SEQ ID NO: 188) |
| Cthe2760 | 1st | DLNYDGKVNSTDYLVLKRYLLGTI (SEQ ID NO: 189) |

TABLE 3-continued

| locus | | Amino Acid Sequence |
|---|---|---|
| Cthe2760 | 2nd | DLNRDGRVNSTDMSLMKRYLLGII (SEQ ID NO: 190) |
| Cthe2761 | 1st | DVNGDGKVNSTDCSIVKRYLLKNI (SEQ ID NO: 191) |
| Cthe2761 | 2nd | DVNGDGKVNSTDYSLLKRFVLRNI (SEQ ID NO: 192) |
| Cthe2811 | 1st | DLNGDGKVNSTDLTIMKRYILKNF (SEQ ID NO: 193) |
| Cthe2811 | 2nd | DLNGDGRINSTDLSILHRYLLRII (SEQ ID NO: 194) |
| Cthe2812 | 2nd | DLNRDGKINSTDLTILKRYLLYSI (SEQ ID NO: 196) |
| Cthe2872 | 1st | DINSDGNVNSTDLGILKRIIVKNP (SEQ ID NO: 197) |
| Cthe2872 | 2nd | DVNADGKVNSTDYTVLKRYLLRSI (SEQ ID NO: 198) |
| Cthe2879 | 1st | DINSDGSINSTDVTLLKRHLLREN (SEQ ID NO: 199) |
| Cthe2949 | 1st | DLNGDGLVNSSDYSLLKRYILKQI (SEQ ID NO: 201) |
| Cthe2949 | 2nd | DLNRNGSVDSVDYSILKRFLLKTI (SEQ ID NO: 202) |
| Cthe2950 | 1st | DLNNDGRTNSTDYSLMKRYLLGSI (SEQ ID NO: 203) |

TABLE 3-continued

| locus | | Amino Acid Sequence |
|---|---|---|
| Cthe2950 | 2nd | DVNLDGKVNSSDYTVLRRFLLGSI (SEQ ID NO: 204) |
| Cthe2972 | 1st | DLNGDKQVNSTDYTALKRHLLNIT (SEQ ID NO: 205) |
| Cthe3012 | 1st | DLNGDGNVNSTDSTLMSRYLLGII (SEQ ID NO: 207) |
| Cthe3012 | 2nd | DLNGDGKVNSTDYNILKRYLLKYI (SEQ ID NO: 208) |
| Cthe3132 | 1st | DLNGDGRVNSTDLAVMKRYLLKQV (SEQ ID NO: 209) |
| Cthe3132 | 2nd | DLNGDGKANSTDYQLLKRYILKTI (SEQ ID NO: 210) |
| Cthe3141 | 1st | DVNGDNSIESTDCVWVKRYLLKQI (SEQ ID NO: 213) |
| Cthe3141 | 2nd | DVNGNGTIDSTDYQLLKRFILKVI (SEQ ID NO: 214) |

The protein of the invention may be provided with a dockerin comprising one or two such dockerin-specific sequences, but typically, aspartic acid is substituted for asparagine at a predicted sugar chain modification site in the relevant sequence. The dockerins shown in the table below are examples of such dockerins. In these tables, the dockerins are specified by means of their relevant sequences. Thus, a preferred dockerin can have a dockerin-specific sequence in which D is substituted for N in (N-X-T/S) in one or two relevant sequences of any of the dockerins in the table below.

TABLE 4

| locus | | Amino Acid Sequence | | |
|---|---|---|---|---|
| Cthe0032 | 1st | DLNNDGNINSTDYMILKKYILKVL (SEQ ID NO: 75) | 2nd | DLNGDGSINSTDLTILKRFIMKAI (SEQ ID NO: 76) |
| Cthe0043 | 1st | DLNGDGNINSTDFTMLKRAILGNP (SEQ ID NO: 77) | 2nd | DLNRDGNTNSTDLMILRRYLLKLI (SEQ ID NO: 78) |
| Cthe0044 | 1st | DINLDGKINSTDLSALKRHILRIT (SEQ ID NO: 79) | 2nd | DVNNDGSVNSTDASILKKYIAKAI (SEQ ID NO: 80) |
| Cthe0190 | 1st | ELNGDGKINSSDLNMMKRYLLRLI (SEQ ID NO: 81) | 2nd | DLNGDGKINSSDYSILKRYLLRMI (SEQ ID NO: 82) |
| Cthe0239 | 1st | DYNGDGAVNSTDLLACKRYLLYAL (SEQ ID NO: 88) | 2nd | DLDGNGKINSTDYAYLKRYLLKQI (SEQ ID NO: 89) |
| Cthe0269 | 1st | DVNGDGNVNSTDLTMLKRYLLKSV (SEQ ID NO: 94) | 2nd | DVNRDGAINSSDMTILKRYLIKSI (SEQ ID NO: 95) |
| Cthe0270 | 1st | DLNGDGKVNSSDLAILKRYMLRAI (SEQ ID NO: 96) | 2nd | DLNRDGNVNSTDYSILKRYILKAI (SEQ ID NO: 97) |
| Cthe0405 | 1st | DVNGDGNVNSTDVVWLRRFLLKLV (SEQ ID NO: 100) | 2nd | DMNDDGNINSTDMIALKRKVLKIP (SEQ ID NO: 101) |
| Cthe0412 | 1st | DCNGDGKVNSTDAVALKRYILRSG (SEQ ID NO: 102) | 2nd | DVNADGRVNSTDLAILKRYILKEI (SEQ ID NO: 103) |
| Cthe0413 | 1st | DCNDDGKVNSTDVAVMKRYLKKEN (SEQ ID NO: 104) | 2nd | DVNADGKVNSTDFSILKRYVMKNI (SEQ ID NO: 105) |
| Cthe0433 | 1st | DLNGDGRVNSSDLALMKRYVVKQI (SEQ ID NO: 106) | 2nd | DLNGDDKVNSTDYSVLKRYLLRSI (SEQ ID NO: 107) |
| Cthe0536 | 1st | DVNGDGRVNSSDVALLKRYLLGLV (SEQ ID NO: 111) | 2nd | DVNVSGTVNSTDLAIMKRYVLRSI (SEQ ID NO: 112) |

TABLE 4-continued

| locus | Amino Acid Sequence | | |
|---|---|---|---|
| Cthe0543 | 1st DVNFDGRINSTDYSRLKRYVIKSL (SEQ ID NO: 113) | 2nd | DVDGNGRINSTDLYVLNRYILKLI (SEQ ID NO: 114) |
| Cthe0578 | 1st DINLDGKNSSDVTLLKRYIVNKSI (SEQ ID NO: 115) | 2nd | DVNGDGRVNSTDYSYLKRYVLKII (SEQ ID NO: 116) |
| Cthe0624 | 1st DLNNDSKVNAVDImMLKRYILGII (SEQ ID NO: 121) | 2nd | DIYFDGVVNSSDYNIMKRYLLKAI (SEQ ID NO: 122) |
| Cthe0625 | 1st DLNGDGVVNSTDSVILKRHIIKFS (SEQ ID NO: 123) | 2nd | DLNGDGNINSSDVSLMKRYLLRII (SEQ ID NO: 124) |
| Cthe0640 | 1st DLNGDNNVNSTDLTLLKRYLTRVI (SEQ ID NO: 117) | 2nd | DVNGDGKINSTDYSAMIRYILRII (SEQ ID NO: 118) |
| Cthe0660 | 1st DLNGDGKINSTDISLMKRYLLKQI (SEQ ID NO: 125) | 2nd | DINKDGKVNSTDMSILKRVILRNY (SEQ ID NO: 126) |
| Cthe0661 | 1st DVNGDLKVNSTDFSMLRRYLLKTI (SEQ ID NO: 119) | 2nd | DLNGDGRINSSDLTMLKRYLLMEV (SEQ ID NO: 120) |
| Cthe0729 | 1st DSNSDCKVNSTDLTLMKRYLLQQS (SEQ ID NO: 127) | 2nd | DLNGDGKINSSDYTLLKRYLLGYI (SEQ ID NO: 128) |
| Cthe0745 | 1st DINNDKTVNSTDVTYLKRFLLKQI (SEQ ID NO: 129) | 2nd | DVNLDGNINSTDLVILKRYVLRGI (SEQ ID NO: 130) |
| Cthe0797 | 1st DVNGDGKINSTDCTMLKRYILRGI (SEQ ID NO: 131) | 2nd | DVNADLKINSTDLVLMKKYLLRSI (SEQ ID NO: 132) |
| Cthe0798 | 1st DVNLDGQVNSTDFSLLKRYILKVV (SEQ ID NO: 133) | 2nd | DMNNDGNINSTDISILKRILLRN (SEQ ID NO: 134) |
| Cthe0821 | 1st DINRDGKINSTDLGMLNRHILKLV (SEQ ID NO: 135) | 2nd | DIDGNGNINSTDYSWLKKYLKVI (SEQ ID NO: 136) |
| Cthe0825 | 1st DVNDDGKVNSTDLTLLKRYVLKAV (SEQ ID NO: 137) | 2nd | DVNRDGRVNSSDVTLSRYLIRVI (SEQ ID NO: 138) |
| Cthe0912 | 1st DVNGDGTINSTDLTMLKRSVLRAI (SEQ ID NO: 139) | 2nd | DVDKNGSINSTDVLLLSRYLLRVI (SEQ ID NO: 140) |
| Cthe1271 | 1st DTNSDGKINSTDVTALKRHLLRVT (SEQ ID NO: 143) | 2nd | DVNGDGNVNSTDLLLLKRYILGEI (SEQ ID NO: 144) |
| Cthe1398 | 1st DLNGDNRINSTDLTLMKRYILKSI (SEQ ID NO: 145) | 2nd | DINGDGKINSTDYTYLKKYLLQAI (SEQ ID NO: 146) |
| Cthe1400 | 1st DLNGDGRVNSTDYTLLKRYLLGAI (SEQ ID NO: 147) | 2nd | DLNLDGRINSTDYTVLKRYLLNAI (SEQ ID NO: 148) |
| Cthe1838 | 1st DVNGDGRVNSSDLTLMKRYLLKSI (SEQ ID NO: 153) | 2nd | DLNEDGKVNSTDLLALKKLVLREL (SEQ ID NO: 154) |
| Cthe2089 | 1st DVNDDGKVNSTDAVALKRYVLRSG (SEQ ID NO: 161) | 2nd | DLNEDGRVNSTDLGILKRYILKEI (SEQ ID NO: 162) |
| Cthe2137 | 1st DVDGNGTVNSTDVNYMKRYLLRQI (SEQ ID NO: 163) | 2nd | DVDGNGNINSTDLSYLKKYILKLI (SEQ ID NO: 164) |
| Cthe2139 | 1st DVNADGVINSSDIMVLKRFLLRTI (SEQ ID NO: 165) | 2nd | DTNGDGAVNSSDFTLLKRYILRSI (SEQ ID NO: 166) |
| Cthe2179 | 1st DLNGDGNVNSTDSILMKRYLMKSV (SEQ ID NO: 169) | 2nd | DVNLDGRVNSTDRSILNRYLLKII (SEQ ID NO: 170) |
| Cthe2360 | 1st DLNGDGRVNSTDLLLMKKRIIREI (SEQ ID NO: 183) | 2nd | DLNLDGKINSSDYTILKRYVLKSI (SEQ ID NO: 184) |
| Cthe2549 | 1st DVNKDGRINSTDIMYLKGYLLRNS (SEQ ID NO: 185) | 2nd | DVDGNGSVSSLDLTYLKRYILRRI (SEQ ID NO: 186) |
| Cthe2760 | 1st DLNYDGKVNSTDYLVLKRYLLGTI (SEQ ID NO: 189) | 2nd | DLNRDGRVNSTDMSLMKRYLLGII (SEQ ID NO: 190) |
| Cthe2761 | 1st DVNGDGKVNSTDCSIVKRYLLKNI (SEQ ID NO: 191) | 2nd | DVNGDGKVNSTDYSLLKRFVLRNI (SEQ ID NO: 192) |

TABLE 4-continued

| locus | Amino Acid Sequence | | |
|---|---|---|---|
| Cthe2811 | 1st DLNGDGKVNSTDLTIMKRYILKNF (SEQ ID NO: 193) | 2nd | DLNGDGRINSTDLSILHRYLLRII (SEQ ID NO: 194) |
| Cthe2872 | 1st DINSDGNVNSTDLGILKRIIVKNP (SEQ ID NO: 197) | 2nd | DVNADGKVNSTDYTVLKRYLLRSI (SEQ ID NO: 198) |
| Cthe2949 | 1st DLNGDGLVNSSDYSLLKRYILKQI (SEQ ID NO: 201) | 2nd | DLNRNGSVDSVDYSILKRFLLKTI (SEQ ID NO: 202) |
| Cthe2950 | 1st DLNNDGRTNSTDYSLMKRYLLGSI (SEQ ID NO: 203) | 2nd | DVNLDGKVNSSDYTVLRRFLLGSI (SEQ ID NO: 204) |
| Cthe3012 | 1st DLNGDGNVNSTDSTLMSRYLLGII (SEQ ID NO: 207) | 2nd | DLNGDGKVNSTDYNILKRYLLKYI (SEQ ID NO: 208) |
| Cthe3132 | 1st DLNGDGRVNSTDLAVMKRYLLKQV (SEQ ID NO: 209) | 2nd | DLNGDGKANSTDYQLLKRYILKTI (SEQ ID NO: 210) |

The dockerins shown in Table 4 each have two relevant sequences in the dockerin, and each relevant sequence has a predicted N-type sugar chain modification site. A preferred dockerin can be obtained with any of these dockerins by making a dockerin-specific sequence in which aspartic acid is substituted for asparagine at the predicted N-type sugar chain modification site of one or both of the two relevant sequences.

TABLE 5

| locus | Amino Acid Sequence | |
|---|---|---|
| Cthe0109 | 1st DFNSDSSVNSTDLMILNRAVLGLG (SEQ ID NO: 81) | 2nd |
| Cthe0191 | 1st DLNGDAKINSTDLNMMKRYLLQMI (SEQ ID NO: 84) | 2nd DLNGDGKITSSDYNLLKRYILHLI (SEQ ID NO: 85) |
| Cthe0211 | 1st DVNGDGHVNSSDYSLFKRYLLRVI (SEQ ID NO: 86) | 2nd DVNRDGRIDSTDLTMLKRYLIRAI (SEQ ID NO: 87) |
| Cthe0246 | 1st DLNADGKINSTDYNLGKRLILRTI (SEQ ID NO: 90) | 2nd DLNGDSKVDSTDLTALKRYLLGVI (SEQ ID NO: 91) |
| Cthe0435 | 1st DVNADGVVNISDYVLMKRYILRII (SEQ ID NO: 108) | 2nd DVNGDNVINDIDCNYLKRYLLHMI (SEQ ID NO: 109) |
| Cthe0438 | 1st DLNGDNNINSSDYTLLKRYLLHTI (SEQ ID NO: 110) | 2nd |
| Cthe1472 | 1st DLNFDNAVNSTDLLMLKRYILKSL (SEQ ID NO: 149) | 2nd DLNRDNKVDSTDLTILKRYLLKAI (SEQ ID NO: 150) |
| Cthe1890 | 1st DLNADGSINSTDLMIMKRVLLKQR (SEQ ID NO: 155) | 2nd DLNGDGKVTSTDYSLMKRYLLKEI (SEQ ID NO: 156) |
| Cthe1963 | 1st DLNGDGNINSSDLQALKRHLLGIS (SEQ ID NO: 157) | 2nd DVNRSGKVDSTDYSVLKRYILRII (SEQ ID NO: 158) |
| Cthe2193 | 1st DINDDGNINDSTDLQMLKRHLLRSI (SEQ ID NO: 171) | 2nd DTNRDGRVDSTDLALLKRYILRVI (SEQ ID NO: 172) |
| Cthe2194 | 1st DLNGDGNINSTDLQILKKHLLRIT (SEQ ID NO: 173) | 2nd DVTKDGKVDSTDLTLLKRYILRFV (SEQ ID NO: 174) |
| Cthe2195 | 1st DLNDDGKVNSTDFQILKKHLLRIT (SEQ ID NO: 175) | 2nd DLNKDGKVDSSDLSLMKRYLLQII (SEQ ID NO: 176) |
| Cthe2196 | 1st DLNNDGKVNSTDFQLLKMHVLRQE (SEQ ID NO: 177) | 2nd DVNRDGKVDSSDCTLLKRYILRVI (SEQ ID NO: 178) |
| Cthe2197 | 1st DLNGDGKVNSTDLQLMKMHVLRQR (SEQ ID NO: 179) | 2nd DVNRDGKVDSTDVALLKRYILRQI (SEQ ID NO: 180) |

TABLE 5-continued

| locus | Amino Acid Sequence | | |
|---|---|---|---|
| Cthe2879 | 1st DINSDGSINSTDVTLLKRHLLREN (SEQ ID NO: 199) | 2nd | DTDGDGKITSIDLSYLKRYVLRLI (SEQ ID NO: 200) |
| Cthe2972 | 1st DLNGDKQVNSTDYTALKRHLLNIT (SEQ ID NO: 205) | 2nd | DLNGDGKVDSTDLMILHRYLLGII (SEQ ID NO: 206) |

The dockerins shown in Table 5 each have one or two relevant sequences in the dockerin, and have a predicted N-type sugar chain modification site in the N-terminal relevant sequence. A preferred dockerin can be obtained with these dockerins by making a dockerin-specific sequence in which aspartic acid is substituted for asparagine at the predicted N-type sugar chain modification site of this relevant sequence.

TABLE 6

| locus | Amino Acid Sequence | | |
|---|---|---|---|
| Cthe0015 | 1st DVNADGKIDSTDLTLLKRYLLRSA (SEQ ID NO: 73) | 2nd | DTDGNGTVNSTDLNYLKKYILRVI (SEQ ID NO: 74) |
| Cthe0274 | 1st DLNVDGSINSVDITYMKRYLLRSI (SEQ ID NO: 98) | 2nd | DINGDGAINSSDMVLLKRYVLRSI (SEQ ID NO: 99) |
| cthe0918 | 1st DLNRNGIVNDEDYILLKNYLLRGN (SEQ ID NO: 141) | 2nd | DVNKDGKVNSTDCLFLKKYILGLI (SEQ ID NO: 142) |
| Cthe1806 | 1st EVIDTKVIDSTDDIVKYEYQFDKK (SEQ ID NO: 151) | 2nd | TLVLSVNNDSTDKTTVSGYISVDF (SEQ ID NO: 152) |
| Cthe2038 | 1st DIVLDGNINSLDMMKLKKYLIRET (SEQ ID NO: 159) | 2nd | DVNSDGEVNSTDYAYLKRYILRII (SEQ ID NO: 160) |
| Cthe2590 | 1st DLNQDGQVSSTDLVAMKRYLLKNF (SEQ ID NO: 187) | 2nd | DLNSDGKVNSTDLVALKRFLLKEI (SEQ ID NO: 188) |
| Cthe2812 | 1st DLNGDQKVTSTDYTMLKRYLMKSI (SEQ ID NO: 195) | 2nd | DLNRDGKINSTDLTILKRYLLYSI (SEQ ID NO: 196) |

The dockerins shown in Table 6 each have two relevant sequences in the dockerin, and have a predicted N-type sugar chain modification site in the C-terminal relevant sequence. A preferred dockerin can be obtained with these dockerins by making a dockerin-specific sequence in which aspartic acid is substituted for asparagine in the predicted N-type sugar chain modification site of this relevant sequence.

The *C. thermocellum* type I dockerins shown in the following table, the binding ability of which with cohesins has been confirmed from existing literature and the like, are considered when selecting dockerin-specific sequences including preferred dockerins in the protein of the invention. In the following table, the dockerins are each specified by two relevant sequences. A preferred dockerin comprising a dockerin-specific sequence with aspartic acid substituted for asparagine at a predicted N-type sugar chain modification site in a relevant sequence can be obtained if this relevant sequence has 90% or more amino acid sequence similarity with any of the relevant sequences contained in these dockerins.

TABLE 7

| locus | protein | Related Sequence | |
|---|---|---|---|
| Cthe0269 | Cel8A | 1st DVNGDGNVNSTDLTMLKRYLLKSV (SEQ ID NO: 94) | 2nd DVNRDGAINSSDMTILKRYLIKSI (SEQ ID NO: 95) |
| Cthe0412 | Cel9K | 1st DCNGDGKVNSTDAVALKRYILRSG (SEQ ID NO: 102) | 2nd DVNADGRVNSTDLAILKRYILKEI (SEQ ID NO: 103) |
| Cthe0413 | Cbh9A | 1st DCNDDGKVNSTDVAVMKRYLKKEN (SEQ ID NO: 104) | 2nd DVNADGKVNSTDFSILKRYVMNKNI (SEQ ID NO: 105) |
| Cthe0578 | Cel9R | 1st DINLDGKINSSDVTLLKRYIVKSI (SEQ ID NO: 115) | 2nd DVNGDGRVNSTDYSYLKRYVLKII (SEQ ID NO: 116) |
| Cthe0825 | Cel9D | 1st DVNDDGKVNSTDLTLLKRYVLKAV (SEQ ID NO: 137) | 2nd DVNRDGRVNSSDVTILSRYLIRVI (SEQ ID NO: 138) |
| Cthe1838 | Xyn10C | 1st DVNGDGRVNSSDLTLMKRYLLKSI (SEQ ID NO: 153) | 2nd DLNEDGKVNSTDLLALKKLVLREL (SEQ ID NO: 154) |

TABLE 7-continued

| locus | protein | Related Sequence | |
|---|---|---|---|
| Cthe2089 | Cel48S | 1st DVNDDGKVNSTDAVALKRYVLRSG (SEQ ID NO: 161) | 2nd DLNEDGRVNSTDLGILKRYILKEI (SEQ ID NO: 162) |
| Cthe2147 | Cel50 | 1st DVNGDFAVNSNDLTLIKRYVLKNI (SEQ ID NO: 167) | 2nd DVDGDEKITSSDAALVKRYVLRAI (SEQ ID NO: 168) |

TABLE 8

| | | Similarity of Amino Acid Sequence | | | | | | | | | | | | | | |
|---|---|---|---|---|---|---|---|---|---|---|---|---|---|---|---|---|
| | | Cel8A | | Cel9K | | Cbh9A | | Cel9R | | Cel9D | | Xyn10C | | Cel48S | | Cel50 | |
| locus | Related Sequence | 1st | 2nd | 1st | 2nd | 1st | 2nd | 1st | 2nd | 1st | 2nd | 1st | 2nd | 1st | 2nd | 1st 2nd |
| Cthe-0109 | 1st DFNSDSSVNSTDLMILNRAVLGLG (SEQ ID NO: 81) | 85 | 85 | 84 | 85 | 93 | 85 | 85 | 76 | 85 | 85 | 85 | 90 | 80 | 90 | 80 80 |
| | 2nd - | - | - | - | - | - | - | - | - | - | - | - | - | - | - | - - |
| Cthe-0438 | 1st DLNGDNNNSSDYTLLKRYLLHTI (SEQ ID NO: 110) | 95 | 91 | 90 | 95 | 94 | 100 | 91 | 95 | 95 | 91 | 95 | 83 | 91 | 95 | 91 95 |
| | 2nd - | - | - | - | - | - | - | - | - | - | - | - | - | - | - | - - |

The dockerins shown in Table 8 each have one relevant sequence on the N-terminal side, and this relevant sequence has 90% or greater amino acid sequence similarity to one of the relevant sequences in the 8 dockerins shown in Table 7, which have confirmed cohesin binding ability. A preferred dockerin can be obtained by making a dockerin-specific sequence in which aspartic acid has been substituted for asparagine at a predicted N-type sugar chain modification site in this relevant sequence.

The dockerins shown in Table 9 each have two relevant sequences, and the relevant sequence on the C-terminal side has 90% or greater amino acid similarity to one of the relevant sequences in the 8 dockerins shown in Table 7, which have confirmed cohesin binding ability. A preferred dockerin can be obtained by making a dockerin-specific sequence in which aspartic acid has been substituted for asparagine at a predicted N-type sugar chain modification site in this relevant sequence.

TABLE 9

| | | Similarity of Amino Acid Sequence | | | | | | | | | | | | | | |
|---|---|---|---|---|---|---|---|---|---|---|---|---|---|---|---|---|
| | | Cel8a | | Cel9K | | Cbh9A | | Cel9R | | Cel9D | | Xyn10C | | Cel48S | | Cel50 | |
| locus | Related Sequence | 1st | 2nd | 1st | 2nd | 1st | 2nd | 1st | 2nd | 1st | 2nd | 1st | 2nd | 1st | 2nd | 1st | 2nd |
| Cthe0239 | 1st DYNGDGAVNSTDLLACKRYLLYAL (SEQ ID NO: 88) | 80 | 76 | 85 | 76 | 85 | 76 | 71 | 71 | 76 | 71 | 76 | 79 | 80 | 76 | 76 | 71 |
| | 2nd DLDGNGKINSTDYAYLKRVLLKQI (SEQ ID NO: 89) | 87 | 79 | 90 | 91 | 85 | 95 | 83 | 95 | 91 | 83 | 87 | 83 | 90 | 91 | 83 | 91 |
| Cthe0435 | 1st DVNADGVVNISDYVLMKRYILRII (SEQ ID NO: 108) | 83 | 83 | 77 | 83 | 80 | 83 | 79 | 83 | 83 | 83 | 83 | 77 | 81 | 79 | 83 | 83 |
| | 2nd DVNGDNVINDIDCNYLKRYLLHMI (SEQ ID NO: 109) | 83 | 79 | 77 | 83 | 80 | 83 | 75 | 95 | 83 | 79 | 79 | 77 | 81 | 83 | 79 | 79 |
| Cthe2038 | 1st DIVLDGNINSLDMMKLKKYLIRET (SEQ ID NO: 159) | 81 | 77 | 83 | 78 | 78 | 78 | 81 | 72 | 77 | 77 | 77 | 78 | 77 | 78 | 73 | 72 |
| | 2nd DVNSDGEVNSTDYAYLKRYILRII (SEQ ID NO: 160) | 87 | 87 | 86 | 85 | 85 | 91 | 83 | 95 | 87 | 87 | 83 | 81 | 90 | 83 | 83 | 87 |
| Cthe2549 | 1st DVNKDGRINSTDIMYLKGYLLRNS (SEQ ID NO: 185) | 82 | 82 | 79 | 79 | 79 | 82 | 82 | 81 | 86 | 86 | 82 | 86 | 87 | 86 | 73 | 77 |
| | 2nd DVDGNGSVSSLDLTYILKRYLRRI (SEQ ID NO: 186) | 91 | 87 | 81 | 85 | 85 | 91 | 87 | 87 | 87 | 83 | 91 | 79 | 86 | 87 | 87 | 83 |

TABLE 10

| locus | Related Sequence | Similarity of Amino Acid Sequence |||||||||||||| 
| | | Cel8A || Cel9K || Cbh9A || Cel9R || Cel9D || Xyn10C || Cel48S || Cel50 ||
| | | 1st | 2nd | 1st | 2nd | 1st | 2nd | 1st | 2nd | 1st | 2nd | 1st | 2nd | 1st | 2nd |
|---|---|---|---|---|---|---|---|---|---|---|---|---|---|---|---|
| Cthe0015 | 1st DVNADGKIDSTDLTLLKRVLLRSA (SEQ ID NO: 73) | 100 | 91 | 87 | 100 | 95 | 100 | 95 | 90 | 100 | 95 | 100 | 86 | 91 | 100 | 91 | 95 |
| | 2nd DTDGNGTVNSTDLNYLKKYILRVI (SEQ ID NO: 74) | 91 | 87 | 81 | 87 | 90 | 91 | 87 | 91 | 95 | 87 | 87 | 81 | 86 | 83 | 87 | 91 |
| Cthe0032 | 1st DLNNDGNINSTDYMILKKYILKVL (SEQ ID NO: 75) | 87 | 87 | 90 | 90 | 85 | 95 | 83 | 91 | 91 | 91 | 87 | 83 | 90 | 90 | 86 | 91 |
| | 2nd DLNGDGSINSTDLTILKRFIMKAI (SEQ ID NO: 76) | 100 | 95 | 90 | 100 | 100 | 100 | 95 | 87 | 100 | 95 | 100 | 91 | 91 | 100 | 95 | 96 |
| Cthe0043 | 1st DLNGDGNINSTDFTMLKRAILGNP (SEQ ID NO: 77) | 95 | 90 | 84 | 95 | 93 | 95 | 85 | 90 | 95 | 85 | 95 | 85 | 85 | 95 | 90 | 90 |
| | 2nd DLNRDGNTNSTDLMILRRYLLKLI (SEQ ID NO: 78) | 87 | 91 | 88 | 87 | 85 | 87 | 87 | 83 | 87 | 95 | 87 | 86 | 86 | 87 | 83 | 83 |
| Cthe0044 | 1st DINLDGKINSTDLSALKRHILRIT (SEQ ID NO: 79) | 90 | 86 | 88 | 90 | 100 | 90 | 95 | 86 | 90 | 91 | 90 | 86 | 86 | 90 | 81 | 86 |
| | 2nd DVNNDGSVNSTDASILKKYIAKAI (SEQ ID NO: 80) | 91 | 91 | 82 | 91 | 90 | 91 | 95 | 83 | 91 | 95 | 91 | 79 | 86 | 91 | 87 | 95 |
| Cthe0190 | 1st ELNGDGKINSSDLNMMKRYLLRLI (SEQ ID NO: 82) | 95 | 87 | 85 | 95 | 100 | 95 | 91 | 91 | 95 | 95 | 95 | 86 | 86 | 95 | 87 | 91 |
| | 2nd DLNGDGKINSSDYSILKRYLLRMI (SEQ ID NO: 83) | 91 | 83 | 85 | 91 | 94 | 95 | 87 | 95 | 91 | 91 | 91 | 81 | 86 | 91 | 83 | 91 |
| Cthe0191 | 1st DLNGDAKINSTDLNMMKRYLLQMI (SEQ ID NO: 84) | 95 | 87 | 85 | 95 | 100 | 95 | 91 | 91 | 95 | 95 | 95 | 86 | 86 | 95 | 87 | 91 |
| | 2nd DLNGDGKITSSDYNLLKRYILHLI (SEQ ID NO: 85) | 91 | 83 | 85 | 91 | 94 | 95 | 87 | 95 | 91 | 91 | 91 | 81 | 86 | 91 | 83 | 91 |
| Cthe0211 | 1st DVNGDGHVNSSDYSLFKRYLLRVI (SEQ ID NO: 86) | 91 | 83 | 81 | 91 | 90 | 95 | 87 | 95 | 95 | 91 | 91 | 81 | 86 | 91 | 83 | 91 |
| | 2nd DVNRDGRIDSTDLTMLKRYLIRAI (SEQ ID NO: 87) | 95 | 95 | 82 | 95 | 86 | 95 | 95 | 83 | 95 | 100 | 95 | 83 | 86 | 95 | 87 | 91 |
| Cthe0246 | 1st DLNADGKINSTDYNLGKRLILRTI (SEQ ID NO: 90) | 87 | 79 | 76 | 87 | 83 | 91 | 83 | 87 | 87 | 83 | 87 | 83 | 78 | 87 | 79 | 87 |
| | 2nd DLNGDSKVDSTDLTALKRYLLGVI (SEQ ID NO: 91) | 87 | 79 | 94 | 87 | 100 | 87 | 83 | 87 | 91 | 87 | 87 | 90 | 95 | 87 | 79 | 87 |
| Cthe0269 | 1st DVNGDGNVNSTDLTMLKRYLLKSV (SEQ ID NO: 94) | 100 | 95 | 86 | 100 | 90 | 100 | 95 | 87 | 100 | 91 | 100 | 87 | 91 | 100 | 95 | 95 |
| | 2nd DVNRDGAINDDSMTILKRYLIKSI (SEQ ID NO: 95) | 95 | 100 | 78 | 91 | 81 | 91 | 91 | 79 | 91 | 91 | 91 | 79 | 82 | 91 | 91 | 87 |
| Cthe0270 | 1st DLNGDGKVNSSDLAILKRYMLRAI (SEQ ID NO: 96) | 100 | 91 | 90 | 100 | 100 | 100 | 95 | 87 | 100 | 95 | 100 | 87 | 91 | 100 | 91 | 95 |
| | 2nd DLNRDGNVNSTDYSILKRYILKAI (SEQ ID NO: 97) | 91 | 95 | 84 | 91 | 85 | 95 | 91 | 87 | 91 | 95 | 91 | 79 | 82 | 91 | 87 | 91 |
| Cthe0274 | 1st DLNVDGSINSVDITYMKRYLLRSI (SEQ ID NO: 98) | 91 | 87 | 85 | 95 | 93 | 95 | 91 | 87 | 91 | 83 | 87 | 83 | 86 | 91 | 83 | 83 |
| | 2nd DTNGDGAINSSDMVLLKRYVLRSI (SEQ ID NO: 99) | 100 | 95 | 82 | 95 | 90 | 91 | 91 | 79 | 95 | 87 | 95 | 83 | 86 | 87 | 95 | 91 |
| Cthe0405 | 1st DVNGDGNVNSTDVVWLRRFLLKLV (SEQ ID NO: 100) | 91 | 87 | 90 | 91 | 86 | 83 | 87 | 91 | 91 | 91 | 91 | 95 | 95 | 87 | 87 | 91 |
| | 2nd DMNDDGNINSTDMIALKRKVLKIP (SEQ ID NO: 101) | 90 | 86 | 90 | 86 | 93 | 86 | 86 | 82 | 90 | 86 | 90 | 95 | 90 | 86 | 86 | 81 |
| Cthe0412 | 1st DCNGDGKVNSTDAVALKRYILRSG (SEQ ID NO: 102) | 86 | 78 | 100 | 86 | 100 | 82 | 94 | 81 | 86 | 86 | 86 | 90 | 95 | 85 | 78 | 91 |
| | 2nd DVNADGRVNSTDLAILKRYILKEI (SEQ ID NO: 103) | 100 | 91 | 86 | 100 | 91 | 100 | 95 | 87 | 100 | 91 | 100 | 87 | 90 | 100 | 91 | 95 |
| Cthe0413 | 1st DCNDDGKVNSTDVAVMKRYLKKEN (SEQ ID NO: 104) | 90 | 81 | 100 | 91 | 100 | 91 | 94 | 81 | 90 | 86 | 90 | 85 | 95 | 95 | 82 | 95 |
| | 2nd DVNADGKVNSTDFSILKRYVMKNI (SEQ ID NO: 105) | 100 | 91 | 82 | 100 | 91 | 100 | 91 | 91 | 100 | 87 | 100 | 87 | 86 | 100 | 91 | 95 |
| Cthe0433 | 1st DLNGDGRVNSSDLAMKRYVVKQI (SEQ ID NO: 106) | 95 | 87 | 90 | 100 | 95 | 100 | 91 | 87 | 100 | 91 | 95 | 87 | 90 | 100 | 91 | 95 |
| | 2nd DLNGDDKVNSTDYSVLKRYLLRSI (SEQ ID NO: 107) | 95 | 87 | 90 | 95 | 94 | 100 | 91 | 91 | 95 | 87 | 95 | 87 | 91 | 95 | 87 | 95 |

TABLE 10-continued

| locus | Related Sequence | Cel8A 1st | Cel8A 2nd | Cel9K 1st | Cel9K 2nd | Cbh9A 1st | Cbh9A 2nd | Cel9R 1st | Cel9R 2nd | Cel9D 1st | Cel9D 2nd | Xyn10C 1st | Xyn10C 2nd | Cel48S 1st | Cel48S 2nd | Cel50 1st | Cel50 2nd |
|---|---|---|---|---|---|---|---|---|---|---|---|---|---|---|---|---|---|
| Cthe0536 | 1st DVNGDGRVNSSDVALLKRYLLGLV (SEQ ID NO: 111) | 100 | 90 | 90 | 100 | 95 | 95 | 95 | 87 | 100 | 91 | 100 | 85 | 95 | 100 | 90 | 100 |
| | 2nd DVNVSGTVNSTDLAIMKRYVLRSI (SEQ ID NO: 112) | 95 | 95 | 82 | 95 | 90 | 100 | 100 | 79 | 95 | 87 | 91 | 83 | 86 | 91 | 91 | 91 |
| Cthe0543 | 1st DVNFDGRINSTDYSRLKRYYIKSL (SEQ ID NO: 113) | 91 | 83 | 84 | 87 | 83 | 91 | 91 | 87 | 87 | 83 | 87 | 79 | 82 | 87 | 79 | 87 |
| | 2nd DVDGNGRINSTDLYVLNRYILKLI (SEQ ID NO: 114) | 91 | 83 | 86 | 91 | 86 | 91 | 87 | 87 | 91 | 91 | 91 | 90 | 90 | 91 | 83 | 87 |
| Cthe0578 | 1st DINLDGKINSSDVTLLKRYIVKSI (SEQ ID NO: 115) | 95 | 91 | 94 | 95 | 94 | 91 | 100 | 83 | 95 | 91 | 95 | 83 | 91 | 95 | 87 | 95 |
| | 2nd DVNGDGRVNSTDYSYLKRYVLKII (SEQ ID NO: 116) | 87 | 79 | 81 | 87 | 81 | 91 | 83 | 100 | 87 | 87 | 87 | 81 | 86 | 87 | 79 | 87 |
| Cthe0640 | 1st DLNGDNNVNSTDLTLLKRYLTRVI (SEQ ID NO: 117) | 91 | 91 | 85 | 91 | 100 | 91 | 91 | 87 | 95 | 95 | 91 | 81 | 86 | 91 | 87 | 91 |
| | 2nd DVNGDGKINSTDYSAMIRYILRII (SEQ ID NO: 118) | 83 | 75 | 81 | 83 | 85 | 87 | 79 | 91 | 83 | 83 | 83 | 81 | 86 | 83 | 75 | 83 |
| Cthe0661 | 1st DVNGDLKVNSTDFSMLRRYLLKTI (SEQ ID NO: 119) | 95 | 87 | 78 | 95 | 81 | 95 | 87 | 91 | 95 | 87 | 95 | 83 | 82 | 95 | 95 | 91 |
| | 2nd DLNGDGRINSSDLTMLKRYLLMEV (SEQ ID NO: 120) | 100 | 91 | 89 | 100 | 95 | 100 | 95 | 87 | 100 | 91 | 100 | 87 | 90 | 100 | 91 | 95 |
| Cthe0624 | 1st DLNNDSKVNAVDIMMLKRYILGII (SEQ ID NO: 121) | 87 | 79 | 89 | 87 | 94 | 87 | 79 | 83 | 87 | 87 | 83 | 90 | 90 | 87 | 75 | 79 |
| | 2nd DIYFDGVVNSSDYNIMKRYLLKAI (SEQ ID NO: 122) | 83 | 87 | 78 | 83 | 83 | 87 | 87 | 79 | 90 | 83 | 83 | 75 | 78 | 90 | 94 | 90 |
| Cthe0625 | 1st DLNGDGVVNSTDSVILKRHIIKFS (SEQ ID NO: 123) | 90 | 90 | 90 | 90 | 85 | 86 | 86 | 82 | 90 | 86 | 90 | 81 | 90 | 86 | 90 | 95 |
| | 2nd DLNGDGNINSSDVSLMKRYLLRII (SEQ ID NO: 124) | 95 | 91 | 90 | 95 | 100 | 91 | 91 | 91 | 95 | 95 | 95 | 86 | 90 | 95 | 91 | 95 |
| Cthe0660 | 1st DLNGDGKINSTDISLMKRYLLKQI (SEQ ID NO: 125) | 95 | 87 | 85 | 100 | 95 | 100 | 91 | 87 | 100 | 91 | 95 | 87 | 86 | 100 | 91 | 95 |
| | 2nd DINKDGKVNSTDMSILKRVILRNY (SEQ ID NO: 126) | 91 | 91 | 73 | 91 | 86 | 91 | 91 | 81 | 95 | 95 | 91 | 91 | 82 | 95 | 82 | 86 |
| Cthe0729 | 1st DSNSDCKVNSTDLTLMKRYLLQQS (SEQ ID NO: 127) | 90 | 86 | 86 | 91 | 91 | 91 | 86 | 81 | 90 | 90 | 90 | 78 | 81 | 91 | 86 | 86 |
| | 2nd DLNGDGKINSSDYTLLKRYLLGYI (SEQ ID NO: 128) | 95 | 85 | 89 | 95 | 94 | 91 | 90 | 87 | 95 | 90 | 95 | 80 | 90 | 95 | 79 | 95 |
| Cthe0745 | 1st DINNDKTVNSTDVTYLKRFLLKQI (SEQ ID NO: 129) | 87 | 87 | 86 | 87 | 82 | 87 | 83 | 83 | 91 | 83 | 83 | 87 | 90 | 87 | 91 | 95 |
| | 2nd DVNLDGNINSTDLVILKRYVLRGI (SEQ ID NO: 130) | 95 | 95 | 89 | 95 | 100 | 91 | 100 | 79 | 95 | 91 | 95 | 87 | 86 | 91 | 91 | 91 |
| Cthe0797 | 1st DVNGDGKINSTDCTMLKRYILRGI (SEQ ID NO: 131) | 95 | 87 | 86 | 95 | 90 | 95 | 91 | 91 | 95 | 87 | 95 | 83 | 91 | 95 | 87 | 96 |
| | 2nd DVNADLKINSTDLVLMKKYLLRSI (SEQ ID NO: 132) | 95 | 87 | 82 | 95 | 90 | 91 | 91 | 79 | 95 | 87 | 95 | 87 | 86 | 91 | 95 | 91 |
| Cthe0798 | 1st DVNLDGQVNSTDFSLLKRYILKVV (SEQ ID NO: 133) | 91 | 91 | 83 | 91 | 88 | 91 | 91 | 91 | 95 | 91 | 91 | 81 | 81 | 91 | 87 | 91 |
| | 2nd DMNNDGNINSTDSILKRILLRN (SEQ ID NO: 134) | 95 | 95 | 80 | 95 | 90 | 95 | 91 | 86 | 95 | 95 | 95 | 91 | 82 | 96 | 91 | 90 |
| Cthe0821 | 1st DINRDGKINSTDLGMLNRHILKLV (SEQ ID NO: 135) | 91 | 91 | 77 | 91 | 86 | 91 | 91 | 87 | 91 | 100 | 91 | 81 | 81 | 91 | 83 | 87 |
| | 2nd DIDGNGNINSTDYSWLKKYILKVI (SEQ ID NO: 136) | 87 | 83 | 81 | 87 | 81 | 91 | 83 | 100 | 91 | 87 | 87 | 81 | 86 | 87 | 83 | 91 |
| Cthe0825 | 1st DVNDDGKVNSTDLTLLKRYVLKAV (SEQ ID NO: 137) | 100 | 91 | 86 | 100 | 90 | 100 | 95 | 87 | 100 | 95 | 100 | 87 | 91 | 100 | 91 | 95 |
| | 2nd DVNRDGRVNSSDVTILSRYLIRVI (SEQ ID NO: 138) | 91 | 91 | 86 | 91 | 86 | 87 | 91 | 87 | 95 | 100 | 91 | 81 | 90 | 91 | 83 | 95 |

TABLE 10-continued

| locus | Related Sequence | Similarity of Amino Acid Sequence | | | | | | | | | | | | | |
|---|---|---|---|---|---|---|---|---|---|---|---|---|---|---|---|
| | | Cel8A | | Cel9K | | Cbh9A | | Cel9R | | Cel9D | | Xyn10C | | Cel48S | | Cel50 | |
| | | 1st | 2nd | 1st | 2nd | 1st | 2nd | 1st | 2nd | 1st | 2nd | 1st | 2nd | 1st | 2nd | 1st | 2nd |
| Cthe0912 | 1st DVNGDGTINSTDLTMLKRSVLRAI (SEQ ID NO: 139) | 95 | 91 | 82 | 91 | 94 | 95 | 91 | 79 | 95 | 87 | 91 | 87 | 86 | 91 | 91 | 91 |
| | 2nd DVDKNGSINSTDVLLLSRYLLRVI (SEQ ID NO: 140) | 87 | 91 | 86 | 87 | 90 | 83 | 87 | 83 | 95 | 95 | 87 | 90 | 95 | 91 | 83 | 91 |
| Cthe0918 | 1st DLNRNGIVNDEDYILLKNYLLRGN (SEQ ID NO: 141) | 86 | 91 | 84 | 81 | 77 | 86 | 86 | 81 | 86 | 90 | 86 | 77 | 82 | 81 | 81 | 82 |
| | 2nd DVNKDGKVNSTDCLFLKKYILGLI (SEQ ID NO: 142) | 85 | 85 | 80 | 85 | 80 | 85 | 85 | 87 | 90 | 87 | 85 | 85 | 90 | 90 | 76 | 85 |
| Cthe1271 | 1st DTNSDGKINSTDVTALKRHLLRVT (SEQ ID NO: 143) | 95 | 90 | 95 | 95 | 95 | 90 | 90 | 91 | 95 | 95 | 95 | 86 | 100 | 90 | 86 | 95 |
| | 2nd DVNGDGNVNSTDLLLLKRYILGEI (SEQ ID NO: 144) | 91 | 87 | 85 | 91 | 90 | 91 | 87 | 79 | 91 | 90 | 91 | 87 | 90 | 91 | 87 | 87 |
| Cthe1398 | 1st DLNGDNRINSTDLTLMKRYILKSI (SEQ ID NO: 145) | 100 | 91 | 90 | 100 | 95 | 100 | 95 | 87 | 100 | 91 | 100 | 87 | 91 | 100 | 91 | 95 |
| | 2nd DINGDGKINSTDYTYLKKYLLQAI (SEQ ID NO: 146) | 91 | 83 | 86 | 91 | 85 | 95 | 87 | 95 | 91 | 87 | 91 | 83 | 91 | 91 | 83 | 91 |
| Cthe1400 | 1st DLNGDGRVNSTDYTLLKRVLLGAI (SEQ ID NO: 147) | 91 | 83 | 89 | 91 | 94 | 95 | 87 | 87 | 91 | 87 | 91 | 80 | 90 | 91 | 83 | 91 |
| | 2nd DLNLDGRINSTDYTVLKRYLLNAI (SEQ ID NO: 148) | 91 | 87 | 94 | 91 | 93 | 95 | 95 | 87 | 91 | 91 | 91 | 83 | 91 | 91 | 83 | 91 |
| Cthe1472 | 1st DLNFDNAVNSTDLLMLKRYILKSL (SEQ ID NO: 149) | 91 | 91 | 84 | 87 | 83 | 87 | 91 | 75 | 87 | 83 | 87 | 83 | 82 | 87 | 87 | 83 |
| | 2nd DLNRDNKVDSTDLTILKRYLLKAI (SEQ ID NO: 150) | 95 | 95 | 89 | 95 | 90 | 95 | 95 | 83 | 95 | 100 | 95 | 83 | 86 | 95 | 87 | 91 |
| Cthe1806 | 1st EVIDTKVIDSTDDIVKVEYQFDKK (SEQ ID NO: 151) | 75 | — | 75 | 84 | 84 | 76 | 85 | 70 | 75 | 100 | — | 75 | 68 | 84 | — | 100 |
| | 2nd TLVLSVNNDSTDKTTVSGYISVDF (SEQ ID NO: 152) | 75 | 91 | 83 | 83 | 80 | 83 | 70 | 73 | 75 | 83 | 75 | 100 | 83 | 83 | 75 | 100 |
| Cthe1838 | 1st DVNGDGRVNSSDLTLMKRYLLKSI (SEQ ID NO: 153) | 100 | 91 | 86 | 100 | 90 | 100 | 95 | 87 | 100 | 91 | 100 | 87 | 91 | 100 | 91 | 95 |
| | 2nd DLNEDGKVNSTDLLALKKLVLREL (SEQ ID NO: 154) | 87 | 79 | 90 | 87 | 85 | 87 | 83 | 81 | 87 | 81 | 87 | 100 | 90 | 87 | 79 | 83 |
| Cthe1890 | 1st DLNADGSINSTDLMIMKRVLLKQR (SEQ ID NO: 155) | 90 | 86 | 85 | 91 | 85 | 91 | 86 | 81 | 90 | 86 | 90 | 95 | 86 | 91 | 86 | 86 |
| | 2nd DLNGDGKVTSTDYSLMKRYLLKEI (SEQ ID NO: 156) | 95 | 87 | 85 | 95 | 90 | 100 | 91 | 91 | 95 | 87 | 95 | 83 | 86 | 95 | 87 | 95 |
| Cthe1963 | 1st DLNGDGNINSSDLQALKRHLLGIS (SEQ ID NO: 157) | 90 | 85 | 89 | 95 | 100 | 90 | 85 | 82 | 90 | 82 | 90 | 90 | 90 | 90 | 85 | 90 |
| | 2nd DVNRSGKVDSTDYSVLKRYILRII (SEQ ID NO: 158) | 87 | 87 | 81 | 87 | 85 | 91 | 87 | 91 | 87 | 95 | 87 | 81 | 86 | 87 | 79 | 87 |
| Cthe2089 | 1st DVNDDGKVNSTDAVALKRYVLRSG (SEQ ID NO: 161) | 91 | 82 | 95 | 90 | 95 | 86 | 91 | 86 | 91 | 90 | 91 | 90 | 100 | 86 | 82 | 95 |
| | 2nd DLNEDGRVNSTDLGILKRYILKEI (SEQ ID NO: 162) | 100 | 91 | 85 | 100 | 95 | 100 | 95 | 87 | 100 | 91 | 100 | 87 | 86 | 100 | 91 | 95 |
| Cthe2137 | 1st DVDGNGTVNSTDVNYMKRYLLRQI (SEQ ID NO: 163) | 91 | 87 | 86 | 91 | 86 | 91 | 87 | 87 | 95 | 83 | 87 | 87 | 90 | 91 | 91 | 95 |
| | 2nd DVNGNGNINSTDLSYLKKYILKLI (SEQ ID NO: 164) | 91 | 87 | 81 | 91 | 86 | 91 | 87 | 95 | 91 | 91 | 91 | 86 | 86 | 91 | 87 | 87 |
| Cthe2139 | 1st DVNADGVINSSDIMVLKRFLLRTI (SEQ ID NO: 165) | 91 | 91 | 86 | 91 | 85 | 91 | 87 | 83 | 91 | 87 | 91 | 95 | 91 | 91 | 91 | 87 |
| | 2nd DTNGDGAVNSSDFTLLKRYILRSI (SEQ ID NO: 166) | 100 | 95 | 82 | 95 | 85 | 95 | 87 | 87 | 95 | 83 | 95 | 79 | 86 | 91 | 95 | 91 |
| Cthe2179 | 1st DLNGDGNVNSTDSILMKRYLMKSV (SEQ ID NO: 169) | 95 | 91 | 95 | 91 | 90 | 91 | 91 | 83 | 95 | 87 | 95 | 87 | 95 | 91 | 91 | 95 |
| | 2nd DVNLDGRVNSTDRSILNRYLLKII (SEQ ID NO: 170) | 87 | 87 | 83 | 87 | 88 | 87 | 91 | 87 | 87 | 91 | 87 | 77 | 81 | 87 | 79 | 87 |

TABLE 10-continued

| | | Similarity of Amino Acid Sequence | | | | | | | | | | | | | |
|---|---|---|---|---|---|---|---|---|---|---|---|---|---|---|---|
| | | Cel8A | | Cel9K | | Cbh9A | | Cel9R | | Cel9D | | Xyn10C | | Cel48S | | Cel50 | |
| locus | Related Sequence | 1st | 2nd | 1st | 2nd | 1st | 2nd | 1st | 2nd | 1st | 2nd | 1st | 2nd | 1st | 2nd |
| Cthe2193 | 1st DINDDGNINSTDLQMLKRHLLRSI (SEQ ID NO: 171) | 95 | 91 | 82 | 100 | 95 | 95 | 91 | 83 | 95 | 87 | 95 | 87 | 86 | 95 | 91 | 95 |
| | 2nd DTNRDGRVDSTDLALLKRYILRVI (SEQ ID NO: 172) | 91 | 91 | 81 | 91 | 90 | 91 | 91 | 87 | 95 | 100 | 91 | 77 | 86 | 87 | 94 | 91 |
| Cthe2194 | 1st DLNGDGNINSTDLQILKKHLLRIT (SEQ ID NO: 173) | 95 | 90 | 85 | 100 | 100 | 95 | 90 | 86 | 96 | 91 | 95 | 86 | 86 | 95 | 90 | 95 |
| | 2nd DVTKDGKVDSTDLTLLKRYILRFV (SEQ ID NO: 174) | 91 | 91 | 88 | 95 | 95 | 95 | 91 | 87 | 100 | 95 | 91 | 86 | 90 | 100 | 86 | 90 |
| Cthe2195 | 1st DLNDDGKVNSTDFQILKKHLLRIT (SEQ ID NO: 175) | 95 | 86 | 85 | 100 | 94 | 95 | 86 | 91 | 95 | 86 | 95 | 86 | 86 | 95 | 86 | 95 |
| | 2nd DLNKDGKVDSSDLSLMKRYLLQII (SEQ ID NO: 176) | 91 | 91 | 83 | 91 | 100 | 91 | 91 | 87 | 95 | 100 | 91 | 86 | 86 | 95 | 83 | 87 |
| Cthe2196 | 1st DLNNDGKVNSTDFQLLKMHVLRQE (SEQ ID NO: 177) | 95 | 90 | 85 | 100 | 90 | 95 | 86 | 90 | 95 | 90 | 95 | 86 | 86 | 95 | 86 | 95 |
| | 2nd DVNRDGKVDSSDCTLLKRYILRVI (SEQ ID NO: 178) | 87 | 87 | 81 | 87 | 85 | 87 | 87 | 91 | 91 | 95 | 87 | 77 | 86 | 87 | 79 | 91 |
| Cthe2197 | 1st DLNGDGKVNSTDLQLMKMHVLRQR (SEQ ID NO: 179) | 95 | 86 | 85 | 100 | 95 | 95 | 90 | 86 | 95 | 90 | 95 | 86 | 86 | 95 | 86 | 95 |
| | 2nd DVNRDGKVDSTDVALLKRYILRQI (SEQ ID NO: 180) | 91 | 91 | 86 | 95 | 86 | 91 | 91 | 83 | 95 | 95 | 91 | 83 | 90 | 95 | 87 | 95 |
| Cthe2360 | 1st DLNGDGRVNSTDLLLMKKRIIREI (SEQ ID NO: 183) | 91 | 83 | 85 | 91 | 85 | 91 | 87 | 79 | 91 | 83 | 91 | 91 | 86 | 91 | 83 | 87 |
| | 2nd DLNLDGKINSSDYTILKRYVLKSI (SEQ ID NO: 184) | 91 | 87 | 89 | 91 | 88 | 95 | 95 | 87 | 91 | 87 | 91 | 79 | 86 | 91 | 83 | 91 |
| Cthe2590 | 1st DLNQDGQVSSTDLVAMKRYLLKNF (SEQ ID NO: 187) | 91 | 95 | 90 | 95 | 95 | 91 | 91 | 81 | 95 | 95 | 91 | 95 | 95 | 91 | 87 | 87 |
| | 2nd DLNSDGKVNSTDLVALKRFLLKEI (SEQ ID NO: 188) | 95 | 91 | 95 | 95 | 95 | 91 | 91 | 83 | 95 | 91 | 95 | 100 | 95 | 91 | 87 | 91 |
| Cthe2760 | 1st DLNVDGKVNSTDYLVLKRYLLGTI (SEQ ID NO: 189) | 83 | 79 | 94 | 83 | 87 | 87 | 83 | 83 | 83 | 83 | 83 | 85 | 90 | 83 | 75 | 83 |
| | 2nd DLNRDGRVNSTDMSLMKRYLLGII (SEQ ID NO: 190) | 87 | 87 | 82 | 87 | 94 | 87 | 87 | 83 | 87 | 95 | 87 | 80 | 80 | 87 | 79 | 83 |
| Cthe2761 | 1st DVNGDGKVNSTDCSIVKRYLLKNI (SEQ ID NO: 191) | 95 | 87 | 82 | 95 | 86 | 95 | 91 | 91 | 95 | 87 | 95 | 83 | 86 | 95 | 87 | 95 |
| | 2nd DVNGDGKVNSTDYSLLKRFVLRNI (SEQ ID NO: 192) | 95 | 87 | 82 | 95 | 86 | 100 | 91 | 91 | 95 | 87 | 95 | 87 | 86 | 95 | 87 | 95 |
| Cthe2811 | 1st DLNGDGKVNSTDLTIMKRYILKNF (SEQ ID NO: 193) | 100 | 91 | 90 | 100 | 95 | 100 | 95 | 90 | 100 | 95 | 100 | 87 | 91 | 100 | 91 | 95 |
| | 2nd DLNGDGRINSTDLSILHRYLLRII (SEQ ID NO: 194) | 95 | 87 | 85 | 95 | 100 | 95 | 91 | 91 | 95 | 91 | 95 | 86 | 86 | 95 | 87 | 91 |
| Cthe2812 | 1st DLNGDQKVTSTDYTMLKRYLMKSI (SEQ ID NO: 195) | 91 | 83 | 85 | 91 | 90 | 95 | 87 | 87 | 91 | 83 | 91 | 79 | 86 | 91 | 87 | 95 |
| | 2nd DLNRDGKINSTDLTILKRYLLYSI (SEQ ID NO: 196) | 91 | 91 | 88 | 91 | 94 | 91 | 91 | 85 | 91 | 100 | 91 | 80 | 85 | 91 | 83 | 87 |
| Cthe2872 | 1st DINSDGNVNSTDLGILKRIIVKNP (SEQ ID NO: 197) | 95 | 95 | 78 | 95 | 86 | 95 | 91 | 86 | 95 | 95 | 95 | 91 | 82 | 95 | 91 | 90 |
| | 2nd DVNADGKVNSTDYTVLKRYLLRSI (SEQ ID NO: 198) | 95 | 87 | 91 | 95 | 90 | 100 | 91 | 91 | 95 | 87 | 95 | 87 | 95 | 95 | 87 | 95 |
| Cthe2879 | 1st DINSDGSINSTDVTLLKRHLLREN (SEQ ID NO: 199) | 100 | 100 | 90 | 100 | 91 | 95 | 95 | 90 | 100 | 100 | 100 | 86 | 95 | 100 | 95 | 100 |
| | 2nd DTDGDGKITSIDLSYLKRYVLRLI (SEQ ID NO: 200) | 91 | 79 | 81 | 91 | 90 | 91 | 83 | 95 | 91 | 87 | 87 | 81 | 86 | 87 | 79 | 83 |
| Cthe2949 | 1st DLNGDLVNSSDYSLLKRYILKQI (SEQ ID NO: 201) | 87 | 83 | 80 | 91 | 85 | 95 | 83 | 87 | 91 | 83 | 87 | 79 | 81 | 91 | 87 | 91 |
| | 2nd DLNRNGSVDSVDYSILKRFLLKTI (SEQ ID NO: 202) | 91 | 91 | 84 | 91 | 85 | 95 | 87 | 91 | 91 | 91 | 87 | 83 | 82 | 91 | 83 | 87 |

TABLE 10-continued

| locus | Related Sequence | Similarity of Amino Acid Sequence | | | | | | | | | | | | | |
|---|---|---|---|---|---|---|---|---|---|---|---|---|---|---|---|
| | | Cel8A | | Cel9K | | Cbh9A | | Cel9R | | Cel9D | | Xyn10C | | Cel48S | Cel50 |
| | | 1st | 2nd | 1st | 2nd | 1st | 2nd | 1st | 2nd | 1st | 2nd | 1st | 2nd | 1st | 2nd |
| Cthe2950 | 1st DLNNDGRTNSTDYSLMKRYLLGSI (SEQ ID NO: 203) | 91 | 87 | 84 | 91 | 94 | 95 | 87 | 87 | 91 | 87 | 91 | 80 | 85 | 91 83 91 |
| | 2nd DVNLDGKVNSSDYTVLRRFLLGSI (SEQ ID NO: 204) | 87 | 83 | 94 | 87 | 93 | 91 | 91 | 83 | 87 | 83 | 87 | 85 | 90 | 87 79 87 |
| Cthe2972 | 1st DLNGDKQVNSTDYTALKRHLLNII (SEQ ID NO: 205) | 86 | 81 | 89 | 86 | 88 | 90 | 81 | 91 | 86 | 82 | 86 | 80 | 90 | 86 86 90 |
| | 2nd DLNGDGKVDSTDLMILHRVLLGII (SEQ ID NO: 206) | 87 | 79 | 89 | 87 | 94 | 87 | 83 | 83 | 87 | 83 | 87 | 90 | 90 | 87 79 83 |
| Cthe3012 | 1st DLNGDGNVNSTDSTLMSRYLLGII (SEQ ID NO: 207) | 87 | 83 | 94 | 87 | 94 | 87 | 83 | 87 | 87 | 87 | 87 | 80 | 95 | 87 83 91 |
| | 2nd DLNGDGKVNSTDYNILKRYLLKYI (SEQ ID NO: 208) | 91 | 83 | 85 | 91 | 90 | 95 | 87 | 91 | 91 | 87 | 91 | 81 | 86 | 91 83 91 |
| Cthe3132 | 1st DLNGDGRVNSTDLAVMKRYLLKQV (SEQ ID NO: 209) | 95 | 87 | 95 | 100 | 95 | 100 | 91 | 87 | 100 | 91 | 95 | 91 | 95 | 100 91 95 |
| | 2nd DLNGDGKANSTDYQLLKRYILKTI (SEQ ID NO: 210) | 91 | 79 | 85 | 95 | 90 | 95 | 83 | 91 | 91 | 87 | 91 | 83 | 86 | 91 83 91 |

The dockerins shown in Table 10 each have two relevant sequences, and each of the relevant sequences has 90% or greater amino acid similarity to one of the relevant sequences in the 8 dockerins shown in Table 7, which have confirmed cohesin binding ability. A preferred dockerin can be obtained by making a dockerin-specific sequence in which aspartic acid has been substituted for asparagine at a predicted N-type sugar chain modification site in one or both of these relevant sequences.

When the amino acid sequence of a dockerin has 90% or greater similarity to the amino acid sequence of any of the known dockerins having cohesin binding ability shown in Table 7, moreover, a preferred dockerin can be obtained by making a dockerin-specific sequence in which aspartic acid has been substituted for asparagine at a predicted N-type sugar chain modification site in this dockerin.

TABLE 11

| locus | Amino Acid Sequence | Similarity of Amino Acid Sequence | | | |
|---|---|---|---|---|---|
| | | Cel8A | Cel9K | Cbh9A | Cel9R |
| Cthe0043 | DLNGDGNINSTDFTHLKRAILGNPAPGTNLAAGDLNRDGNTNSTDLMILRRYLLKLI (SEQ ID NO: 3) | 91 | 83 | 83 | 76 |
| Cthe0044 | DNLDGKINSTDLSALKRHILRITTLSGKQLENADVNNDGSVNSTDASILKKYIAKAI (SEQ ID NO: 4) | 86 | 81 | 88 | 77 |
| Cthe0109 | DFNSDSSVNSTDLMILNRAVLGLG (SEQ ID NO: 5) | 85 | 85 | 85 | 76 |
| Cthe0211 | DVNGDHVNSSDYSLFKRYLLRVIDRFPVGDQSVADVNRDGRIDSTDLTMLKRYLIRAI (SEQ ID NO: 8) | 86 | 83 | 88 | 91 |
| Cthe0269 | DVNGDGNVNSTDLTMLKRYLLKSVTNINREAADVNRDGAINSSDMTILKRYLIKSI (SEQ ID NO: 12) | 100 | 87 | 89 | 77 |
| Cthe0270 | DLNGDGKVNSSDLAILKRYMLRAISDFPIPEGRKLADLNRDGNVNSTDYSILKRYILKAI (SEQ ID NO: 13) | 88 | 82 | 82 | 87 |
| Cthe0405 | DVNGDGNVNSTDVVWLRRFLLKLVEDFPVPSGKQAADMNDDGNINSTDMILKRKVLKIP (SEQ ID NO: 15) | 82 | 79 | 77 | 75 |
| Cthe0412 | DCNGDGKVNSTDAVALKRYILRSGISINTDNADVNADGRVNSTDLAILKRYILKEI (SEQ ID NO: 16) | 87 | 100 | 96 | 74 |
| Cthe0413 | DCNDDGKVNSTDVAVMKRYLKKENVNINLDNADVNADGKVNSTDFSILKRYVMKNI (SEQ ID NO: 17) | 89 | 96 | 100 | 79 |
| Cthe0433 | DLNGDGRVNSSDLALMKRYVVKQIEKLNVPVKAADLNGDDKVNSTDYSVLKRYLLRSI (SEQ ID NO: 18) | 87 | 87 | 92 | 80 |
| Cthe0438 | DLNGDNNINSSDYTLLKRYLLHTI (SEQ ID NO: 20) | 95 | 95 | 100 | 95 |

TABLE 11-continued

| locus | Amino Acid Sequence | Cel9D | Xyn10C | Cel48S | Cel50 |
|---|---|---|---|---|---|
| Cthe0536 | DVNGDGRVNSSDVALLKRYLLGLVENINKEAADVNVSGTVNSTDLAIMKRYVLRSI (SEQ ID NO: 21) | 94 | 87 | 87 | 74 |
| Cthe0578 | DINLDGKINSSDVTLLKRYIVKSIDVFPTADPERSLISDVNGDGRVNSTDVSYLKRYVLKII (SEQ ID NO: 23) | 77 | 74 | 79 | 100 |
| Cthe0625 | DLNGDGVVNSTDSVILKRHIIKFSEITDPVKLKAADLNGDGNINSSDVSLMKRYLLRII (SEQ ID NO: 27) | 86 | 82 | 84 | 80 |
| Cthe0660 | DLNGDGKINSTDISLMKRYLLKQIVDLPVEDDIKAADINKDGKVNSTDMSILKRVILRNY (SEQ ID NO: 28) | 88 | 85 | 80 | 82 |
| Cthe0661 | DVNGDLKVNSTDFSMLRRYLLKTIDNFPTENGKQAADLNGDGRINSSDLTMLKRYLLMEV (SEQ ID NO: 25) | 86 | 87 | 84 | 79 |
| Cthe0745 | DINNDKTVNSTDVTYLKRPLLKQINSLPNQKAADVNLDGNINSTDLVILKRYVLRGI (SEQ ID NO: 30) | 91 | 84 | 82 | 74 |
| Cthe0797 | DVNGDGKINSTDCTMLKRYILRGIEEFPSPSGIIAADVNADLKINSTDLVLMKKYLLRSI (SEQ ID NO: 31) | 83 | 80 | 76 | 80 |
| Cthe0798 | DVNLDGQVNSTDFSLLKRYILKVVDINSINVTNADMNNDGNINSTDISILKRLLRN (SEQ ID NO: 32) | 91 | 86 | 88 | 80 |
| Cthe0825 | DVNDDGKVNSTDLTLLKRYVLKAVSTLPSSKAEKNADVNRDGRVNSSDVTILSRYLRVI (SEQ ID NO: 34) | 88 | 80 | 78 | 88 |
| Cthe0912 | DVNGDGTINSTDLTMLKRSVLRAITLTDDAKARADVDKNGSINSTDVLLLSRYLLRVI (SEQ ID NO: 35) | 87 | 82 | 79 | 74 |
| Cthe1398 | DLNGDNRINSTDLTLMKRYLKSIEDLPVEDDLWAADINGDGKINSTDYTYLKKYLLQAI (SEQ ID NO: 38) | 85 | 86 | 84 | 88 |
| Cthe1838 | DVNGDGRVNSSDLTLMKRYLLKSISDFPTPEGKIADLNEDGKVNSTDLLALKKLVLREL (SEQ ID NO: 42) | 83 | 81 | 78 | 83 |
| Cthe2089 | DVNDDGKVNSTDAVALKRYVLRSGISINTDNADLNEDGRVNSTDLGILKRYILKEI (SEQ ID NO: 46) | 89 | 98 | 94 | 74 |
| Cthe2137 | DVDGNGTVNSTDVNYMKRYLLRQIEEFPYEKALMAGDVDGNGNINSTDLSYLKKYILKLI (SEQ ID NO: 47) | 81 | 83 | 80 | 85 |
| Cthe2179 | DLNGDGNVNSTDSILMKRYLMKSVDLNEEQLKAADVNLDGRVNSTDRISLNRYLLKII (SEQ ID NO: 50) | 86 | 85 | 85 | 76 |
| Cthe2193 | DINDDGNINSTDLQMLKRHLLRSILTEKQLLNADTNRDGRVDSTDLALLKRYILRVI (SEQ ID NO: 51) | 81 | 79 | 87 | 91 |
| Cthe2195 | DLNDDGKVNSTDFQILKKHLLRITLLTGKNLSNADLNKDGKVDSSDLSLMKRYLLQII (SEQ ID NO: 53) | 86 | 81 | 86 | 90 |
| Cthe2196 | DLNNDGKVNSTDFQLLKMHVLRQELPAGTDLSNADVNRDGKVDSSDCTLLKRYILRVI (SEQ ID NO: 54) | 82 | 79 | 84 | 91 |
| Cthe2761 | DVNGDGKVNSTDCSIVKRYLLKNEDFPYEYGKEAGDVNGDGKVNSTDYSLLKRFVLRNI (SEQ ID NO: 61) | 86 | 80 | 83 | 80 |
| Cthe2811 | DLNGDGKVNSTDLTIMKRYILKNFDKLAVPEEAADLNGDGRNSTDLSILHRYLLRII (SEQ ID NO: 62) | 86 | 87 | 91 | 82 |
| Cthe2812 | DLNGDQKVTSTDYTMLKRYLMKSIDRFNTSEQAADLNRDGKINSTDLTILKR (SEQ ID NO: 63) | 88 | 84 | 86 | 75 |

| locus | Amino Acid Sequence | Similarity of Amino Acid Sequence | | | |
|---|---|---|---|---|---|
| | | Cel9D | Xyn10C | Cel48S | Cel50 |
| Cthe0043 | DLNGDGNINSTDFTHLKRAILGNPAPGTNLAAGDLNRDGNTNSTDLMILRRYLLKLI | 86 | 83 | 84 | 80 |
| Cthe0044 | DNLDGKINSTDLSALKRHILRITTLSGKQLENADVNNDGSVNSTDASILKKYIAKAI | 90 | 81 | 81 | 88 |
| Cthe0109 | DFNSDSSVNSTDLMILNRAVLGLG | 85 | 90 | 90 | 80 |
| Cthe0211 | DVNGDHVNSSDYSLFKRYLLRVIDRFPVGDQSVADVNRDGRIDSTDLTMLKRYLIRAI | 77 | 84 | 79 | 83 |
| Cthe0269 | DVNGDGNVNSTDLTMLKRYLLKSVTNINREAADVNRDGAINSSDMTILKRYLIKSI | 88 | 83 | 89 | 85 |
| Cthe0270 | DLNGDGKVNSSDLAILKRYMLRAISDFPIPEGRKLADLNRDGNVNSTDYSILKRYILKAI | 93 | 88 | 83 | 88 |
| Cthe0405 | DVNGDGNVNSTDVVWLRRFLLKLVEDFPVPSGKQAADMNDDGNINSTDMILKRKVLKIP | 89 | 93 | 81 | 82 |
| Cthe0412 | DCNGDGKVNSTDAVALKRYILRSGISINTDNADVNADGRVNSTDLAILKRYILKEI | 80 | 81 | 98 | 78 |
| Cthe0413 | DCNDDGKVNSTDVAVMKRYLKKENVNINLDNADVNADGKVNSTDFSILKRYVMKNI | 78 | 78 | 94 | 81 |
| Cthe0433 | DLNGDGRVNSSDLALMKRYVVKQIEKLNVPVKAADLNGDDKVNSTDYSVLKRYLLRSI | 88 | 85 | 87 | 88 |
| Cthe0438 | DLNGDNNINSSDYTLLKRYLLHTI | 95 | 95 | 95 | 95 |

TABLE 11-continued

| | | | | | |
|---|---|---|---|---|---|
| Cthe0536 | DVNGDGRVNSSDVALLKRYLLGLVENINKEAADVNVSGTVNSTDLAIMKRYVLRSI | 85 | 81 | 87 | 81 |
| Cthe0578 | DINLDGKINSSDVTLLKRYIVKSIDVFPTADPERSLISDVNGDGRVNSTDVSYLKRYVLKII | 88 | 83 | 74 | 82 |
| Cthe0625 | DLNGDGVVNSTDSVILKRHIIKFSEITDPVKLKAADLNGDGNINSSDVSLMKRYLLRII | 93 | 88 | 84 | 87 |
| Cthe0660 | DLNGDGKINSTDISLMKRYLLKQIVDLPVEDDIKAADINKDGKVNSTDMSILKRVILRNY | 95 | 90 | 86 | 95 |
| Cthe0661 | DVNGDLKVNSTDFSMLRRYLLKTIDNFPTENGKQAADLNGDGRINSSDLTMLKRYLLMEV | 86 | 82 | 88 | 90 |
| Cthe0745 | DINNDKTVNSTDVTYLKRPLLKQINSLPNQKAADVNLDGNINSTDLVILKRYVLRGI | 88 | 81 | 84 | 86 |
| Cthe0797 | DVNGDGKINSTDCTMLKRYILRGIEEFPSPSGIIAADVNADLKINSTDLVLMKKYLLRSI | 90 | 91 | 80 | 88 |
| Cthe0798 | DVNLDGQVNSTDFSLLKRYILKVVDINSINVTNADMNNDGNINSTDISILKRLLRN | 89 | 84 | 85 | 84 |
| Cthe0825 | DVNDDGKVNSTDLTLLKRYVLKAVSTLPSSKAEKNADVNRDGRVNSSDVTILSRYLRVI | 100 | 91 | 81 | 93 |
| Cthe0912 | DVNGDGTINSTDLTMLKRSVLRAITLTDDAKARADVDKNGSINSTDVLLLSRYLLRVI | 91 | 82 | 86 | 85 |
| Cthe1398 | DLNGDNRINSTDLTLMKRYLKSIEDLPVEDDLWAADINGDGKINSTDYTYLKKYLLQAI | 90 | 88 | 86 | 90 |
| Cthe1838 | DVNGDGRVNSSDLTLMKRYLLKSISDFPTPEGKIADLNEDGKVNSTDLLALKKLVLREL | 91 | 100 | 83 | 86 |
| Cthe2089 | DVNDDGKVNSTDAVALKRYVLRSGISINTDNADLNEDGRVNSTDLGILKRYILKEI | 81 | 83 | 100 | 80 |
| Cthe2137 | DVDGNGTVNSTDVNYMKRYLLRQIEEFPYEKALMAGDVDGNGNINSTDLSYLKKYILKLI | 91 | 84 | 85 | 90 |
| Cthe2179 | DLNGDGNVNSTDSILMKRYLMKSVDLNEEQLKAADVNLDGRVNSTDRISLNRYLLKII | 90 | 81 | 86 | 85 |
| Cthe2193 | DINDDGNINSTDLQMLKRHLLRSILTEKQLLNADTNRDGRVDSTDLALLKRYILRVI | 79 | 81 | 86 | 86 |
| Cthe2195 | DLNDDGKVNSTDFQILKKHLLRITLLTGKNLSNADLNKDGKVDSSDLSLMKRYLLQII | 80 | 83 | 85 | 83 |
| Cthe2196 | DLNNDGKVNSTDFQLLKMHVLRQELPAGTDLSNADVNRDGKVDSSDCTLLKRYILRVI | 79 | 82 | 85 | 86 |
| Cthe2761 | DVNGDGKVNSTDCSIVKRYLLKNEDFPYEYGKEAGDVNGDGKVNSTDYSLLKRFVLRNI | 90 | 86 | 81 | 90 |
| Cthe2811 | DLNGDGKVNSTDLTIMKRYILKNFDKLAVPEEAADLNGDGRNSTDLSILHRYLLRII | 90 | 89 | 87 | 88 |
| Cthe2812 | DLNGDQKVTSTDYTMLKRYLMKSIDRFNTSEQAADLNRDGKINSTDLTILKR | 90 | 81 | 84 | 83 |

The amino acid sequence of each of the dockerins shown in Table 11 has 90% or greater similarity to any amino acid sequence of the 8 dockerins shown in Table 7. A preferred dockerin can be obtained by substituting aspartic acid for asparagine in at least one predicted N-type sugar chain modification site of this amino acid sequence.

When a dockerin has a relevant sequence having 90% or greater homology with the amino acid sequence of a relevant sequence of any of the known dockerins with cohesin binding ability shown in Table 7, a preferred dockerin can be obtained by substituting aspartic acid for asparagine at a predicted N-type sugar chain modification site in that relevant sequence of the dockerin. A predicted N-type sugar chain modification site in a dockerin having 90% or greater homology with the amino acid sequence of such a known dockerin is also a preferred candidate for substitution. Only the dockerins shown in Table 7 are applicable to such dockerins. A preferred dockerin can be obtained by substituting aspartic acid for asparagine at a predicted N-type sugar modification site in a relevant sequence in one of these dockerins.

Another embodiment of a dockerin-specific sequence is a dockerin-specific sequence having no intrinsic predicted N-type sugar chain modification site in one of the dockerins disclosed in Table 1 or the relevant sequences of these dockerins disclosed in Table 2. It is sufficient for the protein of the invention to have a dockerin containing at least one such dockerin-specific sequence. The following 29 relevant sequences are examples of relevant sequences that are such dockerin-specific sequences.

TABLE 12

| SEQ ID NO.: | locus | Amino Acid Sequence |
|---|---|---|
| 73 | Cthe0015 1st | DVNADGKIDSTDLTLLKRYLLRSA |
| 85 | Cthe0191 2nd | DLNGDGKITSDYNLLKRYILHLI |
| 87 | Cthe0211 2nd | DVNRDGRIDSTDLTMLKRYLIRAI |
| 91 | Cthe0246 2nd | DLNGDSKVDSTDLTALKRYLLGVI |
| 92 | Cthe0258 1st | DVNGDSKINAIDVLLMKKYILKVI |
| 93 | Cthe0258 2nd | DVNADGQINSIDFTWLKKYMLKAV |

TABLE 12-continued

| SEQ ID NO.: | locus | Amino Acid Sequence |
|---|---|---|
| 98 | Cthe0274 1st | DLNVDGSINSVDITYMKRYLLRSI |
| 109 | Cthe0435 2nd | DVNGDNVINDIDCNYLKRYLLHMI |
| 141 | Cthe0918 1st | DLNRNGIVNDEDYILLKNYLLRGN |
| 150 | Cthe1472 2nd | DLNRDNKVDSTDLTILKRYLLKAI |
| 151 | Cthe1806 1st | EVIDTKVIDSTDDIVKYEYQFDKK |
| 156 | Cthe1890 2nd | DLNGDGKVTSTDYSLMKRYLLKEI |
| 159 | Cthe2038 1st | DIVLDGNINSLDMMKLKKYLIRET |
| 167 | Cthe2147 1st | DVNGDFAVNSNDLTLIKRYVLKNI |
| 168 | Cthe2147 2nd | DVDGDEKITSSDAALVKRYVLRAI |
| 171 | Cthe2193 2nd | DTNRDGRVDSTDLALLKRYILRVI |
| 174 | Cthe2194 2nd | DVTKDGKVDSTDLTLLKRYILRFV |
| 176 | Cthe2195 2nd | DLNKDGKVDSSDLSLMKRYLLQII |
| 178 | Cthe2196 2nd | DVNRDGKVDSSDCTLLKRYILRVI |
| 180 | Cthe2197 2nd | DVNRDGKVDSTDVALLKRYILRQI |
| 181 | Cthe2271 1st | DVNLDGSVDSIDLALLYNTTYYAV |
| 182 | Cthe2271 2nd | DVNGDGTVDGIDLAIITAYINGQI |
| 186 | Cthe2549 2nd | DVDGNGSVSSLDLTYLKRYILRRI |
| 187 | Cthe2590 1st | DLNQDGQVSSTDLVAMKRYLLKNF |
| 195 | Cthe2812 1st | DLNGDQKVTSTDYTMLKRYLMKSI |
| 200 | Cthe2879 2nd | DTDGDGKITSIDLSYLKRYVLRLI |
| 206 | Cthe2972 2nd | DLNGDGKVDSTDLMILHRYLLGII |
| 211 | Cthe3136 1st | DIDGNGEISSIDYAILKSHLINSN |
| 212 | Cthe3136 2nd | DVDGNGYVNSIDLAILQMYLLGKG |

The protein of the invention may be provided with a dockerin comprising one or two of the dockerin-specific sequences shown in Table 12, and typically a dockerin that inherently has such a dockerin-specific sequence is preferred. Examples of such dockerins are those shown in the following tables. In these tables, the dockerins are specified by their relevant sequences. In these dockerin-specific sequences, an amino acid at a site corresponding to a predicted N-type sugar chain modification site is preferably aspartic acid. A dockerin having one or two such dockerin-specific sequences is preferred.

cohesins has been confirmed from existing literature or the like, are considered when selecting a dockerin-specific sequence having no intrinsic predicted N-type sugar chain modification site in a preferred dockerin. When a dockerin has a relevant sequence with 90% or greater similarity to the amino acid sequence of any of the relevant sequences in these dockerins, it can be used as a preferred dockerin if the

TABLE 13

| locus | Amino Acid Sequence | |
|---|---|---|
| Cthe0258 | 1st DVNGDSKINAIDVLLMKKYILKVI (SEQ ID NO: 92) | 2nd DVNADGQINSIDFTWLKKYMLKAV (SEQ ID NO: 93) |
| Cthe2147 | 1st DVNGDFAVNSNDLTLIKRYVLKNI (SEQ ID NO: 167) | 2nd DVDGDEKITSSDAALVKRYVLRAI (SEQ ID NO: 168) |
| Cthe2271 | 1st DVNLDGSVDSIDLALLYNTTYYAV (SEQ ID NO: 181) | 2nd DVNGDGTVDGIDLAIITAYINGQI (SEQ ID NO: 182) |
| Cthe3136 | 1st DIDGNGEISSIDYAILKSHLINSN (SEQ ID NO: 211) | 2nd DVDGNGYVNSIDLAILQMYLLGKG (SEQ ID NO: 212) |
| Cthe3141 | 1st DVNGNGSIESTDCVWVKRYLLKQI (SEQ ID NO: 213) | 2nd DVNGNGTIDSTDYQLLKRFILKVI (SEQ ID NO: 214) | sequence is a natural dockerin-specific sequence with aspartic acid occupying a site corresponding to a predicted N-type sugar chain modification site in the relevant sequence.

TABLE 14

| | | Similarity of Amino Acid Sequence | | | | | | | | | | | | | | |
|---|---|---|---|---|---|---|---|---|---|---|---|---|---|---|---|---|
| | | Cel8A | | Cel9K | | Cbh9A | | Cel9R | | Cel9D | | Xyn10C | | Cel48S | | Cel50 | |
| locus | Amino Acid Sequence of repeated region | 1st | 2nd | 1st | 2nd | 1st | 2nd | 1st | 2nd | 1st | 2nd | 1st | 2nd | 1st | 2nd | 1st | 2nd |
| Cthe0258 | 1st DVNGDSKINAIDVLLMKKYILKVI (SEQ ID NO: 92) | 91 | 79 | 90 | 91 | 86 | 87 | 83 | 87 | 95 | 87 | 87 | 90 | 95 | 91 | 79 | 91 |
| | 2nd DVNADGQINSIDFTWLKKYMLKAY (SEQ ID NO: 93) | 95 | 87 | 86 | 95 | 81 | 95 | 83 | 95 | 95 | 83 | 91 | 87 | 91 | 95 | 87 | 87 |
| Cthe2147 | 1st DVNGDFAVNSNDLTLIKRYVLKNI (SEQ ID NO: 167) | 95 | 91 | 78 | 91 | 82 | 91 | 87 | 79 | 91 | 83 | 91 | 79 | 82 | 91 | 100 | 87 |
| | 2nd DVDGDEKITSSDAALVKRYVLRAI (SEQ ID NO: 168) | 95 | 87 | 91 | 95 | 96 | 95 | 95 | 87 | 95 | 95 | 95 | 83 | 95 | 95 | 87 | 100 |
| Cthe2271 | 1st DVNLDGSVDSIDLALLYNTTYYAV (SEQ ID NO: 181) | 93 | 87 | 83 | 93 | 100 | 93 | 93 | 81 | 93 | 87 | 87 | 81 | 81 | 93 | 81 | 81 |
| | 2nd DVNGDGTVDGIDLAIITAYINGQI (SEQ ID NO: 182) | 95 | 85 | 80 | 83 | 90 | 87 | 85 | 80 | 95 | 80 | 85 | 80 | 85 | 83 | 79 | 85 |
| Cthe3136 | 1st DIDGNGEISSIDYAILKSHLINSN (SEQ ID NO: 211) | 95 | 86 | 86 | 90 | 87 | 100 | 86 | 90 | 95 | 80 | 86 | 80 | 91 | 90 | 86 | 91 |
| | 2nd DVDGNGYVNSIDLAILQMYLLGKG (SEQ ID NO: 212) | 95 | 85 | 79 | 95 | 90 | 95 | 85 | 85 | 95 | 80 | 90 | 80 | 83 | 95 | 85 | 85 |
| Cthe3141 | 1st DVNGNGSIESTDCVWVKRYLLKQI (SEQ ID NO: 213) | 87 | 83 | 86 | 91 | 82 | 87 | 83 | 91 | 91 | 83 | 87 | 87 | 90 | 87 | 87 | 91 |
| | 2nd DVNGNGTIDSTDYQLLKRFILKVI (SEQ ID NO: 214) | 87 | 83 | 81 | 87 | 86 | 91 | 83 | 87 | 91 | 83 | 83 | 86 | 86 | 87 | 83 | 95 |

The dockerins shown in Table 13 have two relevant sequences in the dockerin, and no predicted N-type sugar chain modification site in either relevant sequence.

In the protein of the invention, the *C. thermocellum* type I dockerins shown in Table 7, the binding ability of which with The dockerins shown in Table 14 have two relevant sequences, and each of these relevant sequences has 90% or greater similarity to the amino acid sequence of one of the 8 dockerins shown in Table 7, the binding ability of which with cohesins has been confirmed from existing literature or the like. Moreover, one or both of these relevant sequences is a natural dockerin-specific sequence. Aspartic acid may also be substituted for asparagine at a predicted N-type sugar chain modification site in a relevant sequence that is not a natural dockerin-specific sequence.

When a dockerin has an amino acid sequence with 90% or greater similarity to the amino acid sequence of any of the aforementioned known dockerins, moreover, it can be used as a preferred dockerin if it has at least one natural dockerin-specific sequence in which a site corresponding to a predicted N-type sugar chain modification site is occupied by aspartic acid in an intrinsic relevant sequence of the dockerin.

They can be used as preferred dockerins because they have natural dockerin-specific sequences in which at least one site corresponding to a N-type sugar chain modification site in the amino acid sequence is occupied by aspartic acid. When there is another relevant sequence in which a predicted N-type sugar chain modification site is occupied by asparagine, aspartic acid can be substituted for that asparagine.

The protein of the invention can be provided with an active site in addition to the dockerin. The type of active site can be selected appropriately according to the use. The protein of the invention can also be an artificial protein in which a dockerin is suitably combined with an active site. A cellulase that is a

TABLE 15

| locus | Amino Acid Sequence | Similarity of Amino Acid Sequence | |
|---|---|---|---|
| | | Cel8A | Cel9K |
| Cthe1806 | EVITKVIDSTDDIVKYEYQFDKKILCADKETEILYFTVVADEEEIYTSDNTRTLVLSVNNDSTDKTTVSGY (SEQ ID NO: 41) | 67 | 75 |
| Cthe2147 | DVNGDFAVNSNDLTLIKRYVLKNIDEFPSSHGLKAADVDGDEKITSSDAALVKRYVLRAI (SEQ ID NO: 49) | 85 | 78 |
| Cthe3136 | DIDGNGEISSIDYAILKSHLINSNLTFKQLAAADVDGNGYVNSIDLAILQMYLLGKGGTSDI (SEQ ID NO: 71) | 87 | 88 |
| Cthe3141 | DVNGNGSIESTDCVWVKRYLLKQIDSFPNENGARAADVNGNGTIDSTDYQLLKRFILKVI (SEQ ID NO: 72) | 75 | 84 |

| locus | Amino Acid Sequence | Similarity of Amino Acid Sequence | |
|---|---|---|---|
| | | Cbh9A | Cel9R |
| Cthe1806 | EVITKVIDSTDDIVKYEYQFDKKILCADKETEILYFTVVADEEEIYTSDNTRTLVLSVNNDSTDKTTVSGY | 91 | 83 |
| Cthe2147 | DVNGDFAVNSNDLTLIKRYVLKNIDEFPSSHGLKAADVDGDEKITSSDAALVKRYVLRAI | 81 | 82 |
| Cthe3136 | DIDGNGEISSIDYAILKSHLINSNLTFKQLAAADVDGNGYVNSIDLAILQMYLLGKGGTSDI | 90 | 73 |
| Cthe3141 | DVNGNGSIESTDCVWVKRYLLKQIDSFPNENGARAADVNGNGTIDSTDYQLLKRFILKVI | 80 | 90 |

| locus | Amino Acid Sequence | Similarity of Amino Acid Sequence | |
|---|---|---|---|
| | | Cel9D | Xyn10C |
| Cthe1806 | EVITKVIDSTDDIVKYEYQFDKKILCADKETEILYFTVVADEEEIYTSDNTRTLVLSVNNDSTDKTTVSGY | 75 | 70 |
| Cthe2147 | DVNGDFAVNSNDLTLIKRYVLKNIDEFPSSHGLKAADVDGDEKITSSDAALVKRYVLRAI | 93 | 86 |
| Cthe3136 | DIDGNGEISSIDYAILKSHLINSNLTFKQLAAADVDGNGYVNSIDLAILQMYLLGKGGTSDI | 80 | 73 |
| Cthe3141 | DVNGNGSIESTDCVWVKRYLLKQIDSFPNENGARAADVNGNGTIDSTDYQLLKRFILKVI | 80 | 75 |

| locus | Amino Acid Sequence | Similarity of Amino Acid Sequence | |
|---|---|---|---|
| | | Cel48S | Cel50 |
| Cthe1806 | EVITKVIDSTDDIVKYEYQFDKKILCADKETEILYFTVVADEEEIYTSDNTRTLVLSVNNDSTDKTTVSGY | 70 | 100 |
| Cthe2147 | DVNGDFAVNSNDLTLIKRYVLKNIDEFPSSHGLKAADVDGDEKITSSDAALVKRYVLRAI | 80 | 100 |
| Cthe3136 | DIDGNGEISSIDYAILKSHLINSNLTFKQLAAADVDGNGYVNSIDLAILQMYLLGKGGTSDI | 90 | 77 |
| Cthe3141 | DVNGNGSIESTDCVWVKRYLLKQIDSFPNENGARAADVNGNGTIDSTDYQLLKRFILKVI | 76 | 91 |

The dockerins shown in Table 15 have amino acid sequences each having 90% or greater similarity to the amino acid sequence of any of the 8 dockerins shown in Table 7.

constituent protein of a cellulosome and already has an intrinsic dockerin can also be used either as is or after modifications.

The protein of the invention can have cellulolysis promoting activity for example when it is used to saccharify a cellulose-containing material from biomass. That is, it can be provided with a cellulolysis-promoting active site. Examples of cellulolysis-promoting activity include cellulase activity, cellulose-binding activity, cellulose loosening activity and the like.

An active site in a known cellulase can be used appropriately as a cellulase active site. Examples of cellulases include endoglucanase (EC 3.2.1.74), cellobiohydrolase (EC 3.2.1.91) and β-glucosidase (EC 23.2.4.1, EC 3.2.1.21). Cellulases are classified into 13 families (5, 6, 7, 8, 9, 10, 12, 44, 45, 48, 51, 61, 74) of the GHF (glycoside hydrolase family) (www.cazy.org/fam/acc.gh.html) based on similarity of amino acid sequence. It is also possible to combine cellulases of the same or different kinds classified into different families.

A cellulase is not particularly limited but is preferably one that itself has strong cellulase activity. Examples of such cellulases include those derived from *Phanerochaete, Trichoderma reesei* and other *Trichoderma, Fusarium, Tremetes, Penicillium, Humicola, Acremonium, Aspergillus* and other filamentous bacteria as well as from *Clostridium, Pseudomonas, Cellulomonas, Ruminococcus, Bacillus* and other bacteria, *Sulfolobus* and other Archaea, and *Streptomyces, Thermoactinomyces* and other *Actinomycetes*. These cellulases or their active sites may also be artificially modified.

Because the protein of the invention is derived from *C. thermocellum*, its cellulolysis-promoting activity is preferably conferred by an amino acid sequence derived from *Clostridium thermocellum*.

From the standpoint of effective use of biomass, the protein of the invention may be provided with a hemicellulase active site. A lignin decomposing enzyme such as lignin peroxidase, manganese peroxidase or laccase is also possible. Other examples include the cellulose loosening proteins expansin and swollenin, and cellulose-binding domains (proteins) that are constituents of cellulosomes and cellulases. Other examples include xylanase, hemicellulase and other biomass decomposing enzymes. All these proteins can improve the accessibility of the cellulase to cellulose.

This protein is preferably provided with the function of extracellular secretability in eukaryotic microorganisms. That is, it is preferably a protein that is produced as a secretory protein in eukaryotic microorganisms. Cellulase and other enzymes often have intrinsic signals for extracellular secretion. A known secretion signal can be used to confer extracellular secretability on a dockerin protein. The secretion signal is selected appropriately according to the type of eukaryotic microorganism. Secretion signals and the like will be explained below.

A person skilled in the art will be able to produce the protein of the invention by genetic recombination or the like in a suitable host microorganism, or obtain it by chemical synthesis.

As explained above, because the protein of the invention has a specific dockerin it has improved binding ability with type I cohesins from *C. thermocellum*, and may have improved accumulation and accumulated density on scaffolding proteins with such cohesins.

(Scaffolding Protein Having Type I Cohesin from *C. thermocellum*)

The protein of the present invention is suitable as a protein for constructing a complex with a scaffolding protein having a type I cohesin from *C. thermocellum*. A scaffolding protein having a type I cohesin from *C. thermocellum* can be provided with 1 or 2 or more type I cohesins from *C. thermocellum*. Cohesins are known as domains on type I and other scaffolding proteins that bind non-covalently to cellulases and the like with enzymatic activity in cellulosomes formed by cellulosome-producing microorganisms (Sakka et al., Protein, Nucleic Acid and Enzyme, Vol. 44, No. 10 (1999), pp. 41-50; Demain, A. L. et al., Microbiol. Mol. Biol. Rev., 69(1), 124-54 (2005); Doi, R. H. et al., J. Bacteriol., 185(20), 5907-5914 (2003), etc.). A scaffolding protein from *C. thermocellum* for binding with the protein of the invention has at least a type I cohesin domain on a type I scaffolding protein. It may also be provided with a type II cohesin domain on a type II scaffolding protein and a type III cohesin domain on a type III scaffolding protein. A number of sequences of such different types of cohesin domains have been determined in various cellulosome-producing microorganisms. The amino acid sequences and DNA sequences of these various types of cohesins can be easily obtained from various protein databases and DNA sequence databases accessible via the NCBI HP (www.ncbi.nlm.nih.gov).

A scaffolding protein having a cohesin from *C. thermocellum* need not itself be a scaffolding protein from *C. thermocellum* as long as it has a type I cohesin from *C. thermocellum*, and may be an artificial protein. The scaffolding protein may have a natural type I cohesin from *C. thermocellum*, or may have a modified cohesin with one or two or more mutations (additions, insertions, deletions or substitutions) introduced in the amino acid sequence of such a cohesin as long as binding ability is retained. Multiple such cohesins or the like may also be provided at suitable intervals in the cohesin protein. The amino acid sequence of a type I scaffolding protein and such a sequence with suitable mutations introduced therein can be used for the total amino acid sequence of the cohesin protein, and for the amino acid sequences between cohesins if such are present.

The scaffolding protein may also have a cellulose binding domain (CBD) of a scaffolding protein selected from types I to III. CBDs are known as domains in scaffolding proteins that bind to cellulose substrates (see Sakka et al above). There may be one or two or more cellulose binding domains. Many amino acid sequences and DNA sequences of CBDs in the cellulosomes of various cellulosome-producing microorganisms have already been determined. These various CBD amino acid sequences and DNA sequences can be easily obtained from various protein databases and DNA sequences databases accessible through the NCBI HP (www.ncbi.nlm.nih.gov) and the like.

The scaffolding protein preferably has extracellular secretability or cell surface display properties in eukaryotic microorganisms. That is, it is preferably a protein that is produced as a secretory protein in eukaryotic microorganisms, or a protein that is displayed on the cell surfaces of eukaryotic microorganisms. A known secretory signal or surface display system can be used to give a cohesin protein extracellular secretability or cell surface display properties.

A person skilled in the art can produce a scaffolding protein having these various domains as necessary by genetic recombination or the like in a suitable host microorganism. Cohesin proteins having cohesin domains of these various scaffolding proteins can also be obtained by chemical synthesis.

As explained above, because the protein of the invention has a specific dockerin, it has improved binding with type I cohesins from *C. thermocellum*, and may have enhanced accumulation and accumulated density on scaffolding proteins with such cohesins.

(Protein Complex)

The disclosures of this Description also provide a protein complex comprising a scaffolding protein having a type I cohesin from *C. thermocellum* and the protein of the invention bound to this scaffolding protein. This protein complex has enhanced activity of the protein of the invention because the accumulated amount and/or accumulated density of the protein of the invention is greater.

(Eukaryotic Microorganism Provided with Protein Complex on Cell Surface)

The eukaryotic microorganism disclosed in this Description is provided on the cell surface with the protein complex disclosed in this Description. In this eukaryotic microorganism, the scaffolding protein and protein of the invention making up the protein complex may be supplied from outside the cell and self-assembled on the cell surface to construct the protein complex, but preferably the microorganism produces these proteins itself. This is because sugar chain modification by the sugar chain modification system is eliminated or controlled even when the protein of the invention is produced within an eukaryotic microorganism, resulting in improved cohesin binding.

When the protein of the invention has cellulase activity or other cellulolysis promotion activity, a protein complex comprising accumulated proteins having cellulase or other cellulolysis promotion activity can be constructed on the cell surface of the eukaryotic microorganism. Such a eukaryotic microorganism can use glucose obtained by decomposition and saccharification of a cellulose-containing material on its cell surface as a carbon source.

There are no particular limits on how the DNA coding for such a protein is retained within the host microorganism as long as it is able to express the protein. For example, it can be linked under the control of a promoter capable of operating in the eukaryotic microorganism, and with a suitable terminator located downstream therefrom. The promoter may be a constitutive promoter or an inducible promoter. In this state, the DNA may be incorporated into a host chromosome, or may be in the form of a 2µ plasmid held within the host nucleus or a plasmid held outside the nucleus. In general, a selection marker gene that is usable in the host is retained at the same time when introducing such exogenous DNA.

The dockerin proteins and cohesin proteins produced in the eukaryotic microorganism are preferably given extracellular secretability or cell surface display properties. The protein of the invention is preferably given extracellular secretability, while the scaffolding protein is preferably given cell surface display properties, by which it is excreted outside the cell and displayed on the cell surface. To give it extracellular secretability, a protein is assigned a secretory signal. Examples of excretory signals include secretory signals of the *Rhizopus oryzae* and *C. albicans* glucoamylase genes, yeast invertase leaders, α-factor leaders and the like. Using an agglutinating protein or a part thereof, the protein can be secreted in such a way that it is displayed on the surface of the eukaryotic microorganism. One example is a peptide consisting of 320 amino acid residues of the 5' region of the SAG1 gene, which codes for the agglutinating protein α-agglutinin. Polypeptides and methods for displaying desired proteins on cell surfaces are disclosed in WO 01/79483, Japanese Patent Application Laid-open No. 2003-235579, WO 2002/042483 pamphlet, WO 2003/016525 pamphlet, Japanese Patent Application Laid-open No. 2006-136223, and the publications of Fujita et al (Fujita et al., 2004, Appl. Environ. Microbiol. 70:1207-1212 and Fujita et al., 2002, Appl. Environ. Microbiol. 68:5136-5141), and Murai et al., 1998, Appl. Environ. Microbiol. 64:4857-4861.

The eukaryotic microorganism is not particularly limited, and for example various known yeasts can be used. For purposes of ethanol fermentation and the like as discussed below, examples include *Saccharomyces cerevisiae* and other *Saccharomyces* yeasts, *Schizosaccharomyces pombe* and other *Schizosaccharomyces* yeasts, *Candida shehatae* and other *Candida* yeasts, *Pichia stipitis* and other *Pichia* yeasts, *Hansenula* yeasts, *Trichosporon* yeasts, *Brettanomyces* yeasts, *Pachysolen* yeasts, *Yamadazyma* yeasts, and *Kluyveromyces marxianus*, *Kluyveromyces lactis* and other *Kluyveromyces* yeasts. Of these, a *Saccharomyces* yeast is desirable from the standpoint of industrial utility and the like, and *Saccharomyces cerevisiae* is especially desirable.

A eukaryotic microorganism expressing an exogenous protein can be prepared according to the methods described in Molecular Cloning, $3^{rd}$ Ed., Current Protocols in Molecular Biology and the like. Vectors and methods for constructing vectors for expressing the protein of the invention and scaffolding protein in a eukaryotic microorganism are similarly well-known to those skilled in the art. The vector can be in various forms according to the mode of use. For example, it can assume the form of a DNA fragment, or of a 2 micron plasmid or other suitable yeast vector. The eukaryotic microorganism disclosed in this description can be obtained by transforming a eukaryotic microorganism with such a vector. Various conventional known methods can be adopted for transformation, such as transformation methods, transfection methods, conjugation methods, protoplast methods, electroporation, lipofection, lithium acetate methods and the like.

(Method for Producing Useful Substance)

The method for producing a useful substance disclosed in this Description may comprise a step of saccharifying and fermenting a cellulose-containing material by means of a process whereby a cellulose-containing material is fermented as a carbon source using the eukaryotic microorganism disclosed in this Description, in which the protein of the invention has cellulolysis promotion activity. With this method, a cellulose-containing material can be directly decomposed and saccharified with a eukaryotic microorganism, and used as glucose or the like by the eukaryotic microorganism. A useful substance is produced by this fermentation step according to the useful substance production ability of the eukaryotic microorganism used.

The useful substance is a product obtained by fermentation of glucose or the like by the eukaryotic microorganism, and differs both according to the type of eukaryotic microorganism and the fermentation conditions. The useful substance is not particularly limited, and can be any produced by yeasts and other eukaryotic microorganisms using glucose. The useful substance may also be a compound that is not an intrinsic metabolite, but one that the yeast or other eukaryotic microorganism has been made capable of synthesizing by a genetically engineered substitution, addition or the like in one or two or more enzymes in the glucose metabolism system. Examples of useful substances include ethanol as well as $C_{3-5}$ lower alcohols, lactic acid and other organic acids, fine chemicals obtained by addition of isoprenoid synthesis pathways (coenzyme Q10, vitamins and other raw materials and the like), glycerin, plastics, synthetic raw materials and the like obtained by modifications in the glycolytic system, and other materials used in biorefinery technology. The useful substance production step may be followed by a step of collecting a useful substance-containing fraction from the culture liquid, and a further step of refining or concentrating this fraction. The collection step and refining or other step can be selected appropriately according to the type of useful substance and the like.

Proteins of the invention retained as protein complexes on the surface of the eukaryotic microorganism preferably have two or more cellulolysis-promoting activities. For example, it is desirable to use two or more cellulases having endoglucanase and cellobiohydrolase or other activity, respectively.

A cellulose-containing material is a material containing cellulose, a β-glucan consisting of D-glucose units condensed through β-1,4 glycosidic bonds. The cellulose-containing material may be any containing cellulose, regardless of derivation or form. Consequently, the cellulose-containing material may include lignocellulose material, crystalline cellulose material, soluble cellulose material (amorphous cellulose material), insoluble cellulose material and various other cellulose materials and the like for example. Examples of lignocellulose materials include lignocellulose materials comprising complexes of lignin and the like in the wood and leaves of woody plants and the leaves, stalks, roots and the like of herbaceous plants. These lignocellulose materials may be rice straw, wheat straw, corn stalks, bagasse and other agricultural waste, collected wood, brush, dried leaves and the like and chips obtained by grinding these, sawdust, chips and other sawmill waste, forest thinnings, damaged wood and other forest waste, and construction waste and other waste products. Examples of crystalline cellulose materials and insoluble cellulose materials include crystalline or insoluble cellulose materials containing crystalline cellulose and insoluble cellulose after separation of lignin and the like from lignocellulose materials. Cellulose materials may also be derived from used paper containers, used paper, used clothes and other used fiber materials and pulp wastewater.

Prior to being brought into contact with a cellulase, cellulose-containing material may also be subjected to suitable pretreatment or the like in order to facilitate decomposition by the cellulase. For example, the cellulose can be partially hydrolyzed to render it amorphous or reduce its molecular weight under acidic conditions using an inorganic acid such as sulfuric acid, hydrochloric acid, phosphoric acid, nitric acid or the like. It can also be treated with supercritical water, alkali, pressurized hot water or the like to render it amorphous or reduce its molecular weight.

Cellulose-containing materials include polymers and derivatives of polymers of glucose units condensed through β-1,4-glycosidic bonds. The degree of glucose polymerization is not particularly limited. Derivatives include carboxymethylated, aldehyded, esterified and other derivatives. The cellulose may be either crystalline cellulose or amorphous cellulose.

As understood in the technical field, identity or similarity in this Description signifies a relationship between two or more proteins or polynucleotides, determined by comparing their sequences. In this field, "identity" signifies the degree of sequence invariance between proteins or polynucleotides as determined by alignment between proteins or polynucleotides or in some cases alignment between a series of such sequences. Similarity signifies the degree of correlation between protein or polynucleotide sequences as determined by alignment of protein or polynucleotide sequences, or in some cases alignment between a series of such sequences. More specifically, it is determined by the identity or conservation (substitution that maintains the physical characteristics of a sequence or specific amino acid in a sequence) of the sequence. In the BLAST sequence homology test results below, similarity is called similarity. The method of determining identity or similarity is preferably designed so as to show the longest possible alignment between sequences. Methods for determining identity or similarity are provided by available public programs. For example, they can be determined using the BLAST (Basic Local Alignment Search Tool) program of Altschul et al (for example, Altschul, S F, Gish W, Miller W, Myers E W, Lipman D J, J. Mol. Biol. 215:403-410 (1990); Altschul S F, Madden T L, Schaffer A A, Zhang J, Miller W, Lipman D J, Nucleic Acids Res. 25:3389-3402 (1997)). The conditions when using software such as BLAST are not particularly limited, but the default values are used by preference.

EXAMPLES

The present invention is explained in detail below using examples, but the present invention is not limited by these examples. The gene recombination operations below were performed in accordance with Molecular Cloning: A Laboratory Manual (T. Maniatis et al., Cold Spring Harbor Laboratory).

Example 1

A pAI-AGA1 vector (FIG. 1) was prepared having an AAP1 homologous region and a HOR7 promoter upstream and a Tdh3 terminator, His3 marker and AAP1 homologous region downstream from an aga1 gene, which was amplified and cloned by ordinary PCR methods. The yeast *S. cerevisiae* BY 4741 was transformed using this vector to obtain a BY-AGA1 yeast displaying large quantities of aga1 on the cell surface.

Example 2

Figure 2:
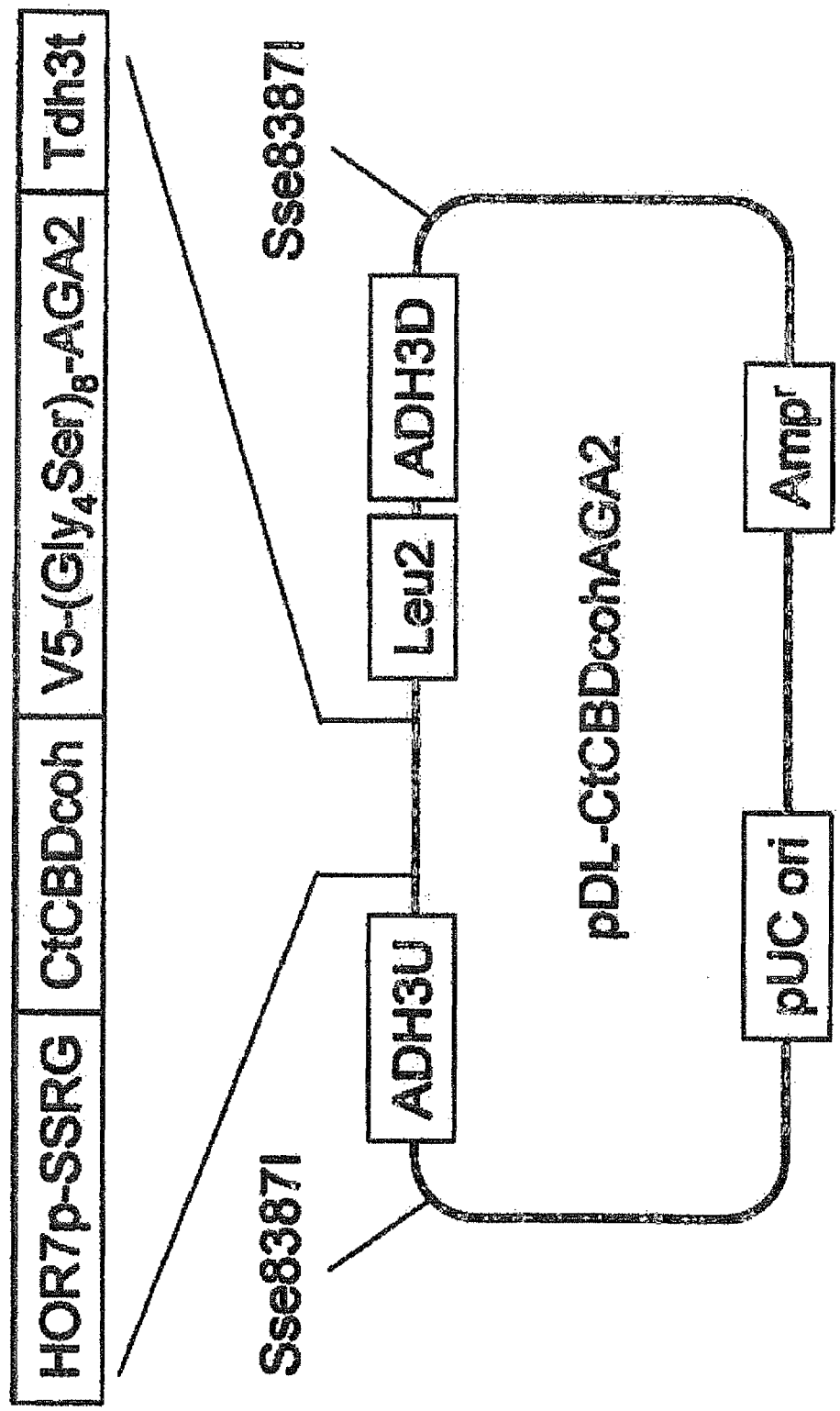
FIG. 2 shows a pDL-CtCBDCohAGA2 vector having a Leu2 marker and ADH3 homologous region prepared in Example 2.

CBD-cohesin was amplified and cloned by ordinary PCR methods from the *C. thermocellum* genome (SEQ ID NO. 215). A pDL-CtCBDCohAGA2 vector was then prepared having an ADH3 homologous region and HOR7 promoter upstream and a V5-tag, aga2, Tdh3 terminator, Leu2 marker and ADH3 homologous region downstream from the resulting gene (FIG. 2). The resulting vector was introduced into the BY-AGA1 yeast prepared in Example 1, to obtain a CtCBDcoh yeast displaying cohesin from *C. thermocellum* on the cell surface.

Example 3

Figure 4:
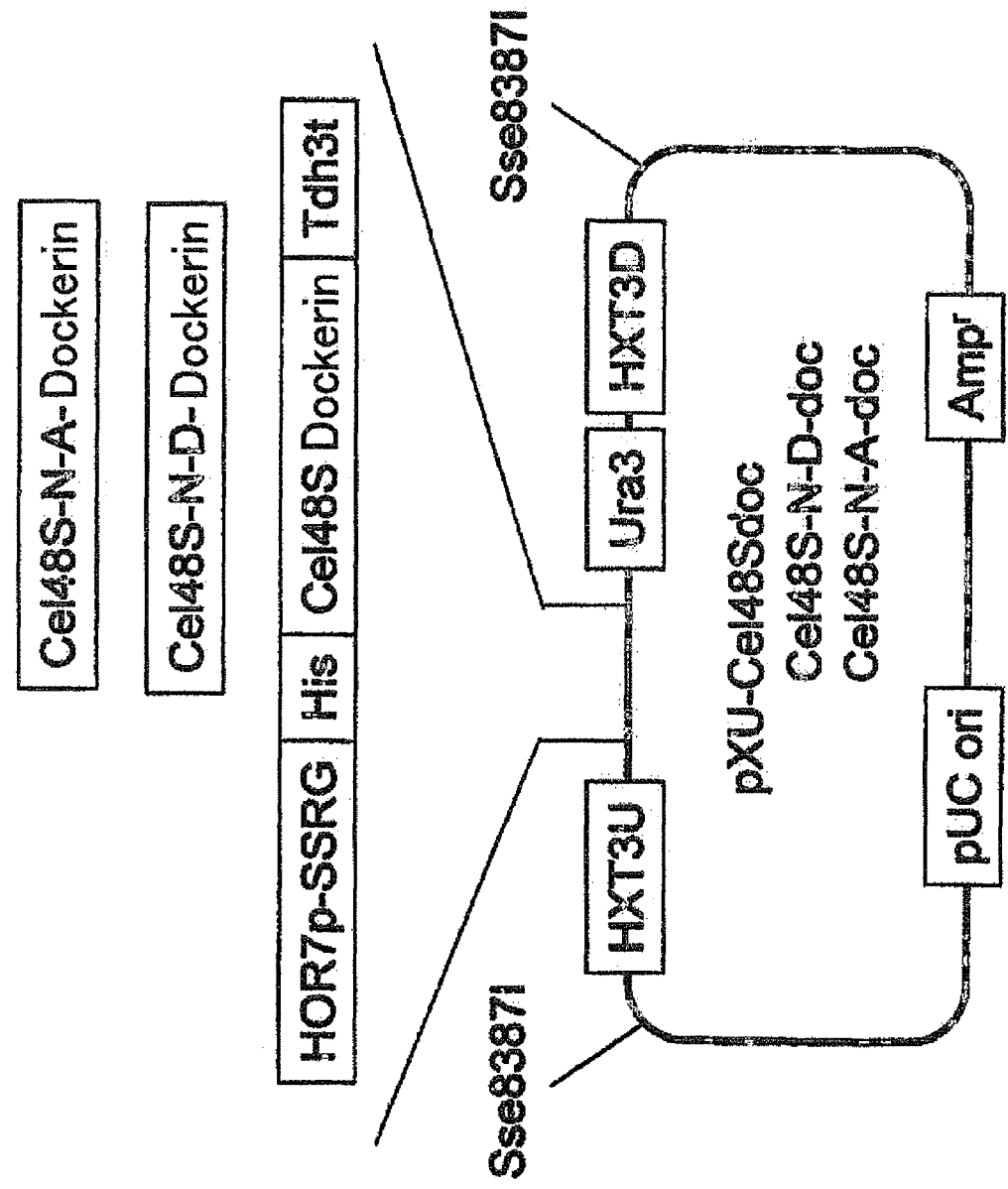
FIG. 4 shows a pXU-Cel48Sdoc vector, pXU-Cel48S-N-A-doc vector and pXU-Cel48S-N-D-doc vector prepared in Example 3.

The Cel48S dockerin gene was amplified and cloned by ordinary PCR methods from the *C. thermocellum* genome (SEQ ID NO. 216). Using the resulting Cel48S dockerin gene as a template, two primers, 48Sdock-N18A-Fw and 48Sdock-N50A-Rv (SEQ ID NOS. 217, 218) were used to obtain a gene having alanine substituted for the No. 18 and No. 50 asparagines. A gene having aspartic acid substituted for the No. 18 and No. 50 asparagines was obtained in the same way using the two primers 48Sdock-N18D-Fw and 48Sdock-N50D-Rv (SEQ ID NOS. 219, 220) with the Cel48S dockerin gene as the template (FIG. 3). A pXU-Cel48Sdoc vector, pXU-Cel48S-N-A-doc vector and pXU-Cel48S-N-Doc vector were prepared each having a HXT3 homologous region, HOR7 promoter and His-tag upstream and a Tdh3 terminator, Ura3 marker and HXT3 homologous region downstream from the respective gene (FIG. 4). The resulting vectors were introduced into the CtCBDcoh yeast obtained in Example 2 to obtain CtCBDcoh48Sdoc, CtCBDcoh48SdocN-A and CtCBDcoh48SdocN-D displaying cohesin from *C. thermocellum* on the cell surface and simultaneously producing a dockerin or amino acid-substituted dockerin.

Example 4

Figure 5:
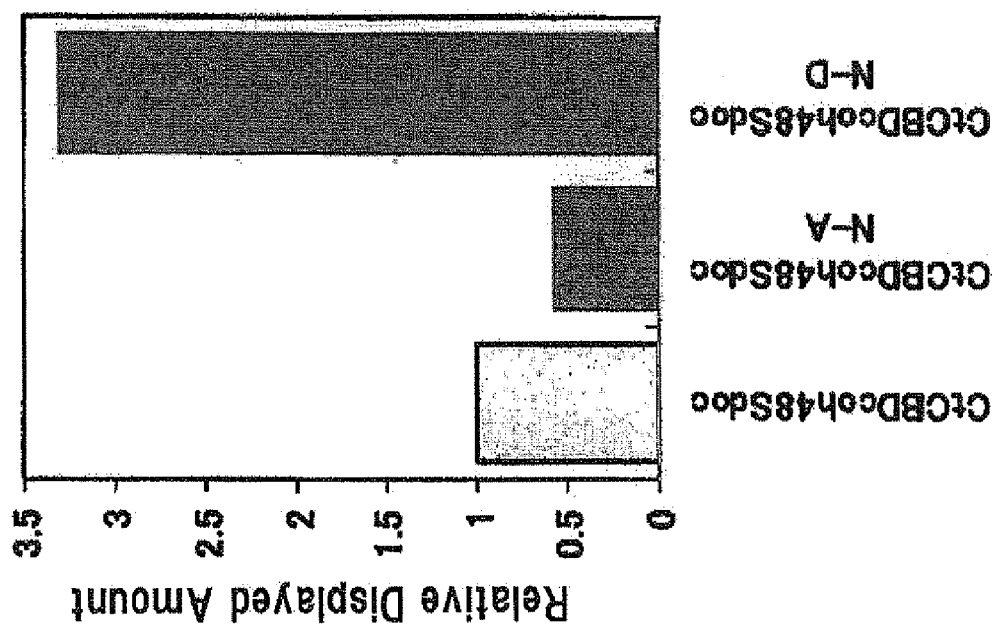
FIG. 5 shows the displayed amount of dockerin in a protein complex surface-displaying yeast containing an amino acid-substituted Cel48S dockerin.
Figure 5:
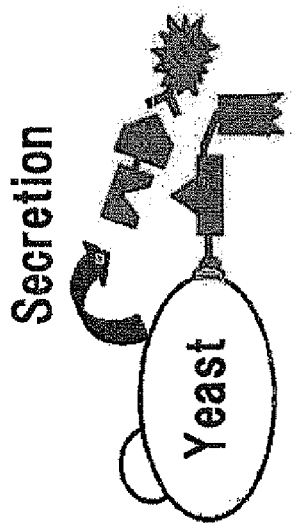

The three yeasts CtCBDcoh48Sdoc, CtCBDcoh48SdocN-A and CtCBDcoh48SdocN-D obtained in Example 3 were each cultured for 24 hours at 30° C. in YP+2% glucose medium, and the equivalent of OD 600=0.5, 62.5 µl was collected, washed with PBS solution, mixed with PBS+1 mg/ml BSA+anti-His-FITC solution, reacted for 30 minutes at 4° C., and washed twice with PBS solution, and the amount of dockerin displayed on the yeast cell surface was then evaluated by flow cytometry. The amount of Cel48S dockerin displayed was reduced by about half by substitution of alanine for asparagine. On the other hand, the amount of Cel48S dockerin displayed was increased by 3.3 times by substitution of aspartic acid for asparagine (FIG. 5).

Example 5

Figure 6A:
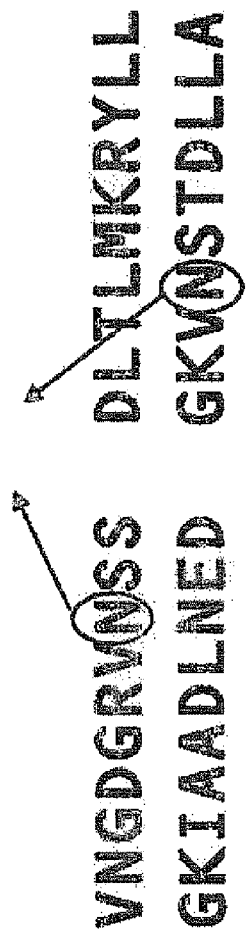
FIG. 6 shows an amino acid sequence having aspartic acid substituted for the No. 18 and No. 54 asparagines in the amino acid sequence of a Xyn10C dockerin gene, and a corresponding genetic sequence.
Figure 7:
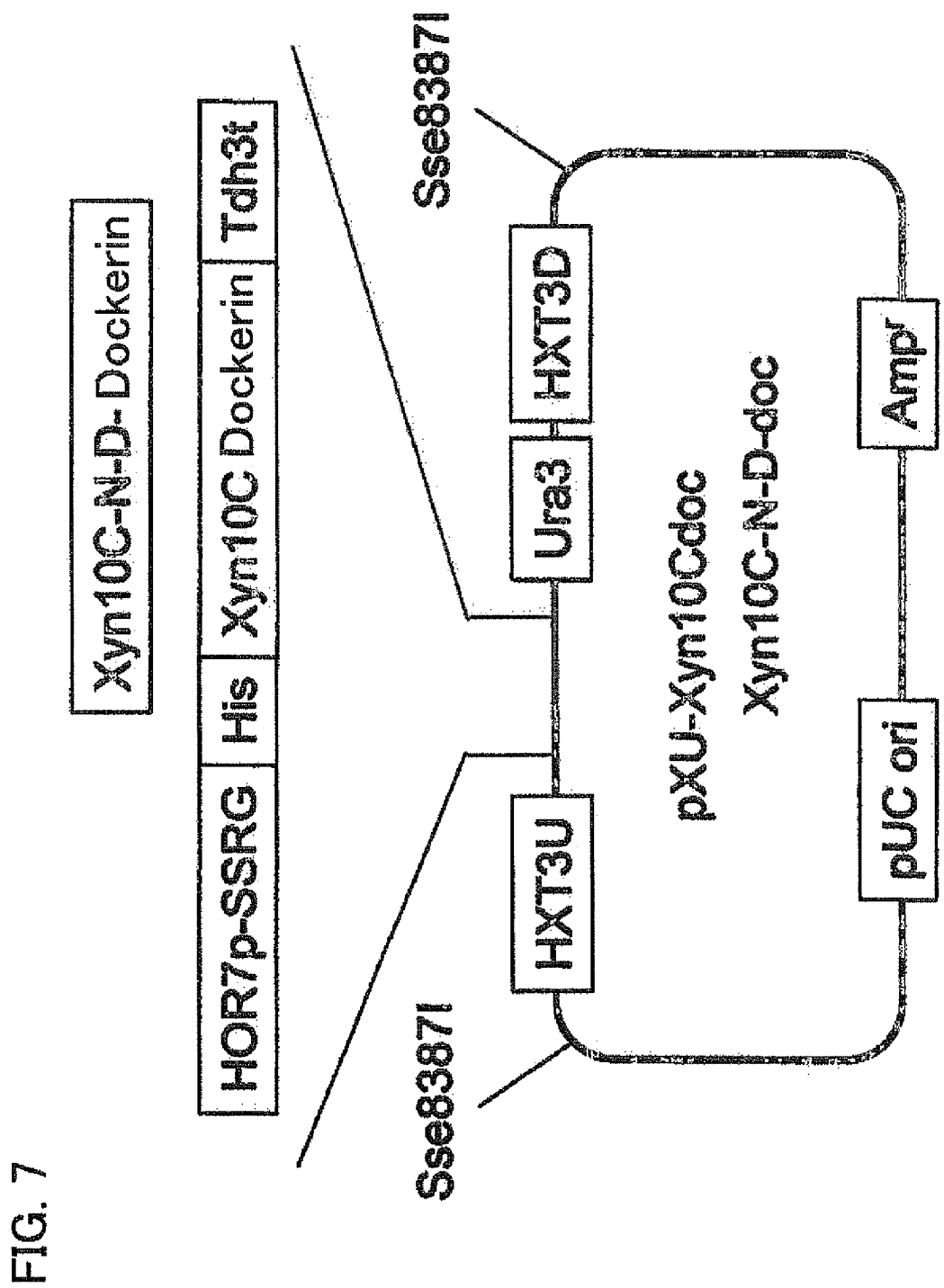
FIG. 7 shows a pXU-Xyn10Cdoc vector and pXU-Xyn10C-N-D-doc vector prepared in Example 5.

The Xyn10C dockerin gene was amplified and cloned by ordinary PCR methods from the C. thermocellum genome (SEQ ID NO. 221). Genes having aspartic acid substituted for the No. 18 and No. 54 asparagine were obtained using the two primers 10Cdock-N18D-Fw and 10Cdock-N50D-Rv (SEQ ID NOS. 222, 223) with this Xyn10C dockerin gene as the template (FIG. 6). A pXU-Xyn10Cdoc vector and pXU-Xyn10C-N-D-doc vector were prepared each having an HXT3 homologous region, HOR7 promoter and His-tag upstream and a Tdh3 terminator, Ura3 marker and HXT3 homologous region downstream from the respective genes (FIG. 7). The resulting vectors were each introduced into the CtCBDcoh yeast obtained in Example 2 to obtain CtCBDcoh10Cdoc and CtCBDcoh10CdocN-D displaying cohesin from C. thermocellum on the cell surface and simultaneously producing a dockerin or amino acid-substituted dockerin.

Example 6

Figure 8:
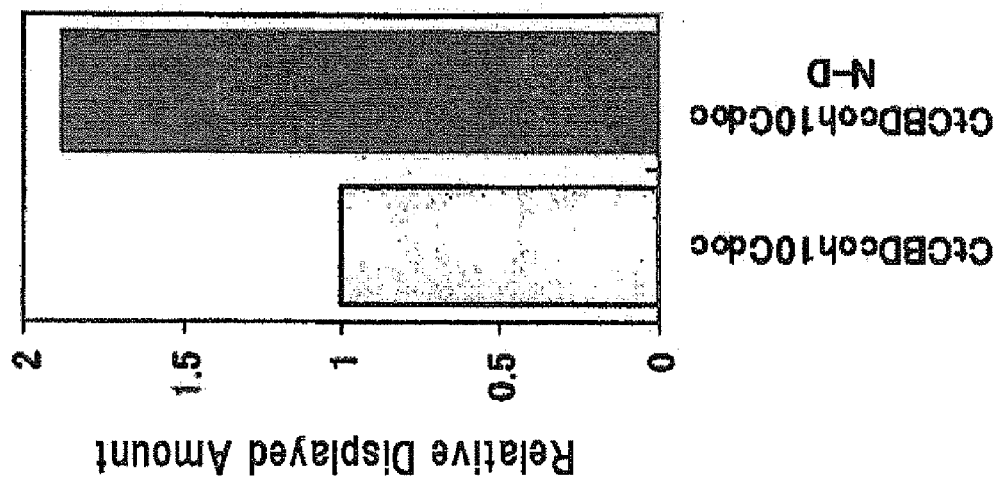
FIG. 8 shows the displayed amount of dockerin in a protein complex surface-displaying yeast containing an amino acid-substituted Xyn10C dockerin.
Figure 8:
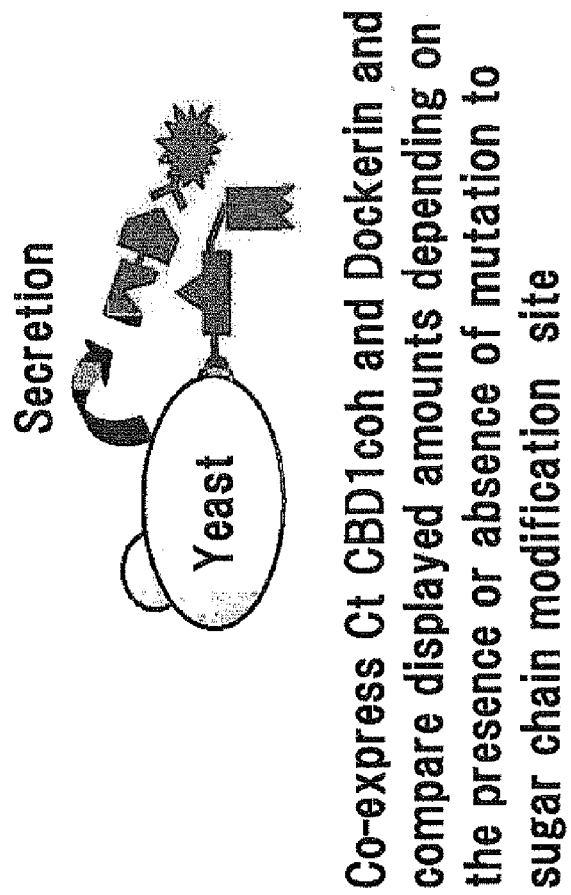

The two yeasts CtCBDcoh10Cdoc and CtCBDcoh10CdocN-D obtained in Example 5 were each cultured for 24 hours at 30° C. in YP+2% glucose medium, and the equivalent of OD 600=0.5, 62.5 µl was collected, washed with PBS solution, mixed with PBS+1 mg/ml BSA+anti-His-FITC solution, reacted for 30 minutes at 4° C., and washed twice with PBS solution, and the amount of dockerin displayed on the yeast cell surface was then evaluated by flow cytometry. The amount of Xyn10C dockerin displayed was increased by 1.8 times by substitution of aspartic acid for asparagine (FIG. 8). The two asparagines targeted in the dockerin in this case are conserved in about 82% of the 142 dockerins attributed to the C. thermocellum genome. Since amino acid substitution had a similar effect in two different dockerins, Cel48S and Xyn10C, it appears that this is applicable to most enzyme groups of C. thermocellum.

Example 7

Figure 9:
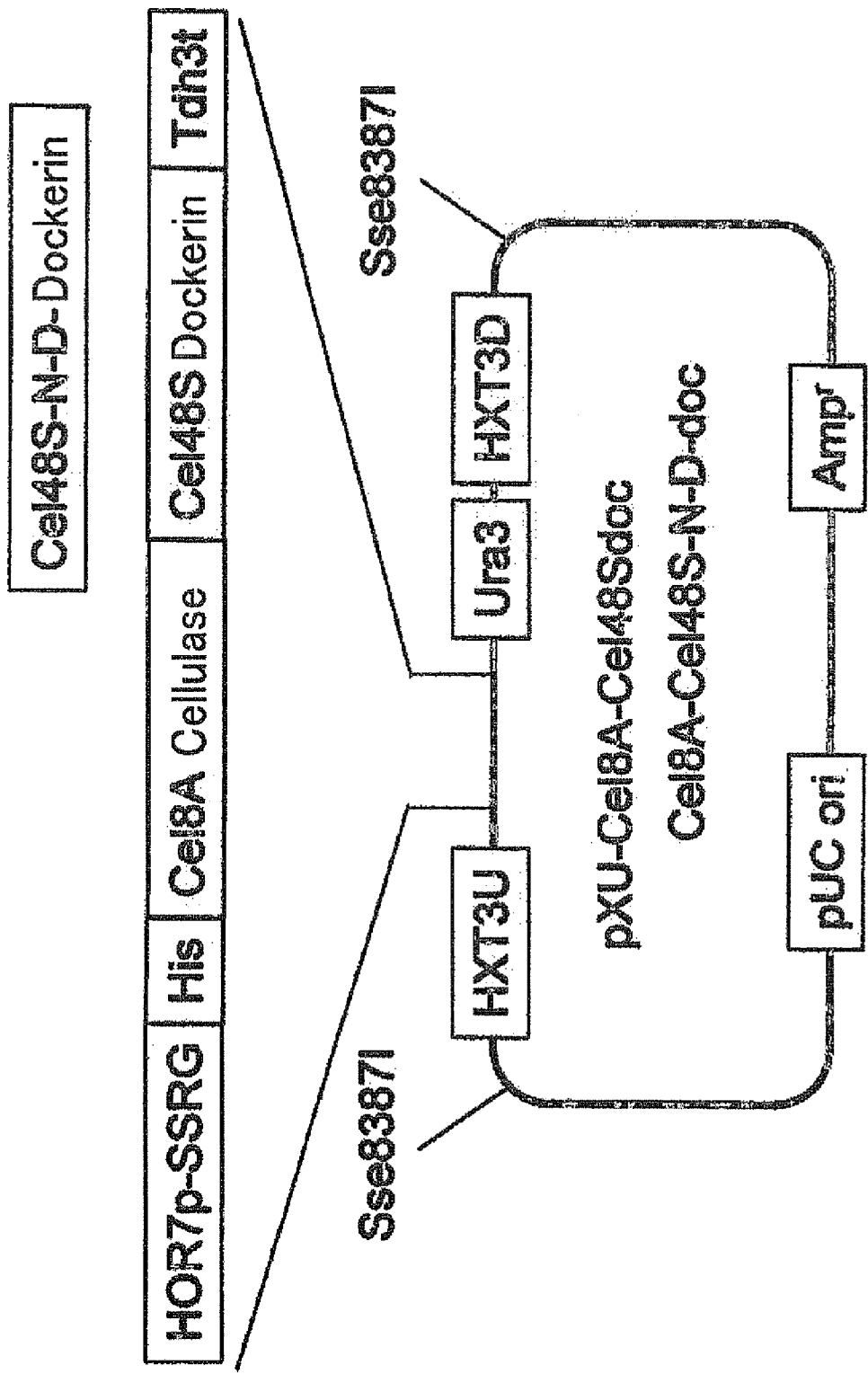
FIG. 9 shows a pXU-Cel8A-Cel48Sdoc and pXU-Cel8A-Cel48S-N-Ddoc vector prepared in Example 7.

The Cel8A cellulase gene was amplified and cloned by ordinary PCR methods from the C. thermocellum genome (SEQ ID NO. 224). The resulting gene was spliced to the Cel48S dockerin gene obtained in Example 3 and to a gene having aspartic acid substituted for the No. 18 and No. 50 asparagines of the Cel48S dockerin, and pXU-Cel8A-Cel48Sdoc and pXU-Cel8A-Cel48S-N-D-doc vectors were prepared each having a HXT3 homologous region, HOR7 promoter and His-tag upstream and a Tdh3 terminator, Ura3 marker and HXT3 homologous region downstream from the respective gene (FIG. 9). The resulting vectors were each introduced into the CtCBDcoh yeast obtained in Example 2 to obtain CtCBDcohCel8A48Sdoc and CtCBDcohCel8A48SdocN-D, each displaying a cohesin from C. thermocellum on the cell surface and simultaneously producing a dockerin-type cellulase or amino acid-substituted dockerin-type cellulase.

Example 8

Figure 10:
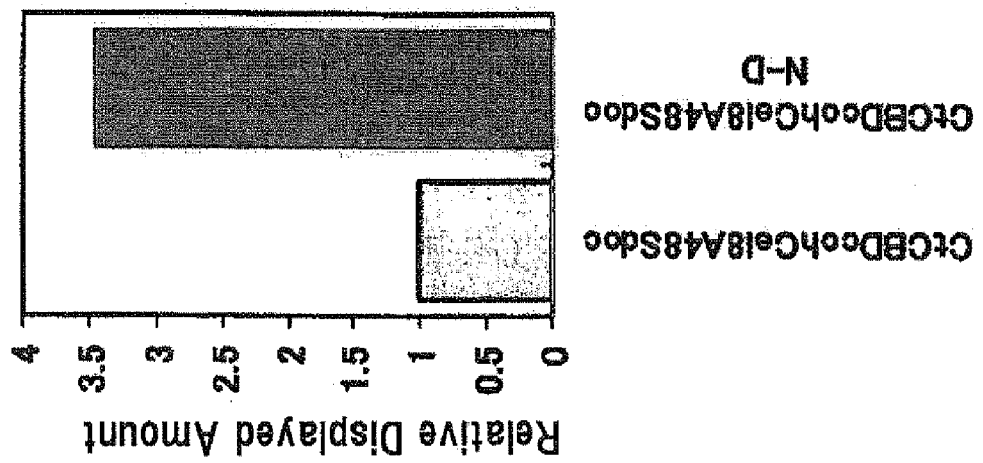
FIG. 10 shows the displayed amount of cellulase in a protein complex surface-displaying yeast containing amino acid-substituted dockerin-type cellulase.
Figure 10:
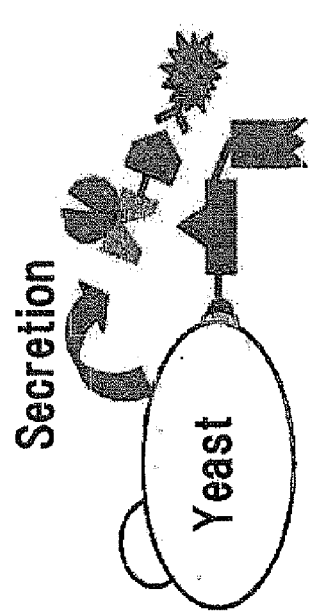

The two yeasts CtCBDcohCel8A48Sdoc and CtCBDcohCel8A48SdocN-D obtained in Example 7 were cultured for 24 hours at 30° C. in YP+2% glucose medium, and the equivalent of OD 600=0.5, 62.5 µl was collected, washed once with PBS solution, mixed with PBS+1 mg/ml BSA+anti-His-FITC solution, reacted for 30 minutes at 4° C., and washed twice with PBS solution, and the displayed amount of CelA on the yeast cell surface was evaluated by flow cytometry. An increase in the displayed amount of CelA was confirmed due to amino acid substitution (FIG. 10).

Example 9

Figure 11:
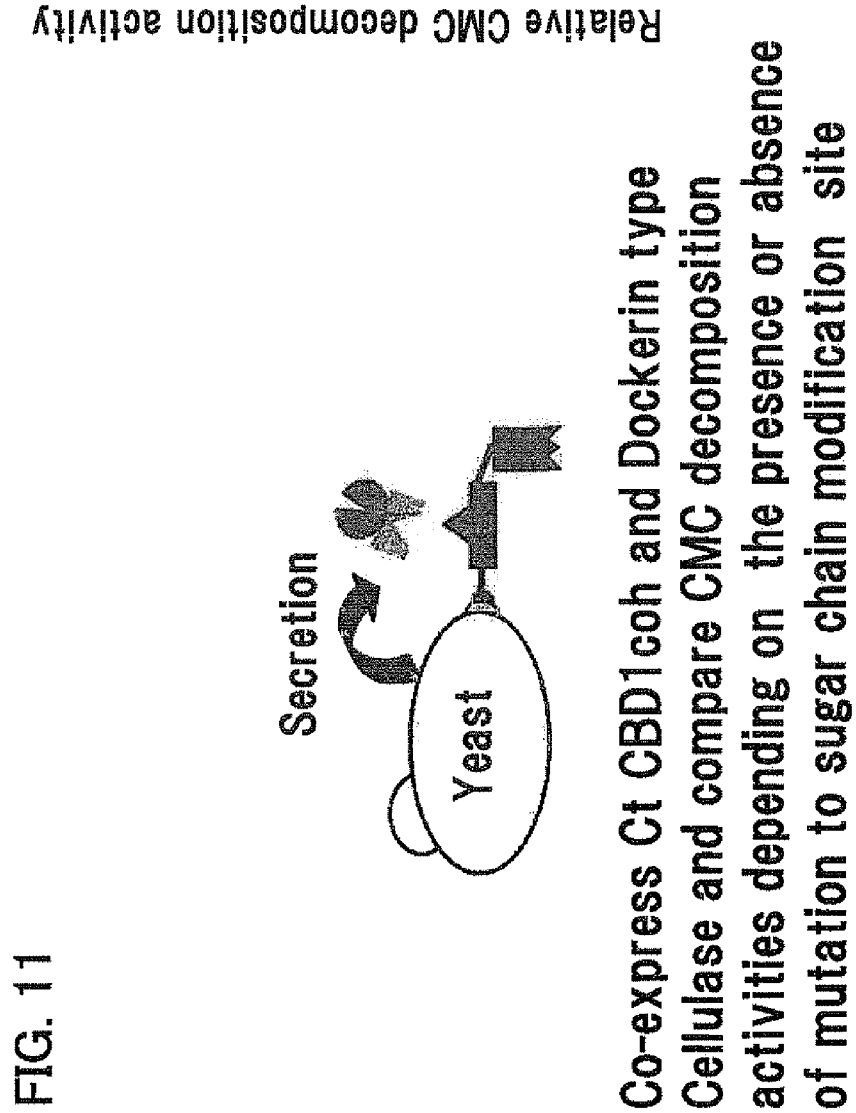
FIG. 11 shows CMC decomposition activity of a protein complex surface-displaying yeast containing amino acid-substituted dockerin-type cellulase.

The two yeasts CtCBDcohCel8A48Sdoc and CtCBDcohCel8A48SdocN-D obtained in Example 7 were cultured for 24 hours at 30° C. in YP+2% glucose medium, and the equivalent of OD 600=1, 1 ml was collected, washed with 50 mM acetic acid buffer pH 6.0 solution, mixed with 1% CMC, 20 mM acetic acid buffer pH 6.0 solution, and reacted for 2 hours at 40° C. to decompose the CMC. CMC decomposition activity was increased by amino acid substitution (FIG. 11), indicating improved saccharification ability of the yeast.

[Sequence Table Free Text]
  SEQ ID NOS. 217, 218, 219, 220, 222, 223: Primers
[Sequence Tables]

What is claimed is:

1. An isolated protein comprising a dockerin domain that includes an amino acid sequence associated with cohesin-dockerin binding wherein the amino acid sequence comprises at least one sequence selected from the group consisting of SEQ ID NOS: 3-5, 8, 12, 13, 15-18, 20, 21, 23, 25, 27, 28, 30-32, 35, 38, 42, 46, 47, 50, 51, 53, 54, 61-63, 74-84, 86, 88-90, 94-97, 99-108, 110-137, 139, 140, 142-149, 152-155, 157, 158, 160-166, 169-171, 173, 175, 177, 179, 183-186, 188-194, 196-199, 201-205, 207-210, 213, and 214 where said sequence is modified by substitution of an aspartic acid for an asparagine in an intrinsic predicted N-type sugar chain modification site, thereby eliminating in vivo sugar chain modification of said sequence when produced in an eukaryotic microorganism.

2. The isolated protein according to claim 1, wherein the amino acid sequence comprises at least one sequence selected from the group consisting of SEQ ID NOS: 74-84, 86, 88-90, 94-97, 99-108, 110-137, 139, 140, 142-149, 152-155, 157, 158, 160-166, 169-171, 173, 175, 177, 179, 183-185, 188-194, 196-199, 201-205, 207-210, 213, and 214 where said sequence is modified by substitution of an aspartic acid for an asparagine in an intrinsic predicted N-type sugar chain modification site, thereby eliminating in vivo sugar chain modification of said sequence when produced in an eukaryotic microorganism.

3. The isolated protein according to claim 1, wherein the amino acid sequence comprises at least one sequence selected from the group consisting of SEQ ID NOS: 75-80, 82, 83, 88, 89, 94-97, 100-107, 111-137, 139, 140, 143-148, 153, 154, 161-166, 169, 170, 183-186, 189-194, 197, 198, 201-204, and 207-210 where said sequence is modified by substitution of an aspartic acid for an asparagine in an intrinsic predicted N-type sugar chain modification site, thereby eliminating in vivo sugar chain modification of said sequence when produced in an eukaryotic microorganism.

4. The isolated protein according to claim 1, wherein the amino acid sequence comprises at least one sequence selected from the group consisting of SEQ ID NOS: 3-5, 8, 12, 13, 15-18, 20, 21, 23, 25, 27, 28, 30-32, 35, 38, 42, 46, 47, 50, 51, 53, 54, and 61-63 where said sequence is modified by substitution of an aspartic acid for an asparagine in an intrinsic predicted N-type sugar chain modification site, thereby eliminating in vivo sugar chain modification of said sequence when produced in an eukaryotic microorganism.

5. The isolated protein according to claim 1, which has cellulolysis-promoting activity.

6. The isolated protein according to claim 5, wherein the cellulolysis-promoting activity is cellulase activity.

7. The isolated protein according to claim 5, wherein the protein further comprises an amino acid sequence from *Clostridium thermocellum*, which confers the cellulolysis-promoting activity.

* * * * *

SEQUENCE LISTING

```
<160> NUMBER OF SEQ ID NOS: 224

<210> SEQ ID NO 1
<211> LENGTH: 58
<212> TYPE: PRT
<213> ORGANISM: Clostridium thermocellum

<400> SEQUENCE: 1

Asp Val Asn Ala Asp Gly Lys Ile Asp Ser Thr Asp Leu Thr Leu Leu
1               5                   10                  15

Lys Arg Tyr Leu Leu Arg Ser Ala Thr Leu Thr Glu Glu Lys Ile Leu
            20                  25                  30
```

```
Asn Ala Asp Thr Asp Gly Asn Gly Thr Val Asn Ser Thr Asp Leu Asn
        35                  40                  45

Tyr Leu Lys Lys Tyr Ile Leu Arg Val Ile
    50                  55

<210> SEQ ID NO 2
<211> LENGTH: 58
<212> TYPE: PRT
<213> ORGANISM: Clostridium thermocellum

<400> SEQUENCE: 2

Asp Leu Asn Asn Asp Gly Asn Ile Asn Ser Thr Asp Tyr Met Ile Leu
1               5                   10                  15

Lys Lys Tyr Ile Leu Lys Val Leu Glu Arg Met Asn Val Pro Glu Lys
            20                  25                  30

Ala Ala Asp Leu Asn Gly Asp Gly Ser Ile Asn Ser Thr Asp Leu Thr
        35                  40                  45

Ile Leu Lys Arg Phe Ile Met Lys Ala Ile
    50                  55

<210> SEQ ID NO 3
<211> LENGTH: 57
<212> TYPE: PRT
<213> ORGANISM: Clostridium thermocellum

<400> SEQUENCE: 3

Asp Leu Asn Gly Asp Gly Asn Ile Asn Ser Thr Asp Phe Thr Met Leu
1               5                   10                  15

Lys Arg Ala Ile Leu Gly Asn Pro Ala Pro Gly Thr Asn Leu Ala Ala
            20                  25                  30

Gly Asp Leu Asn Arg Asp Gly Asn Thr Asn Ser Thr Asp Leu Met Ile
        35                  40                  45

Leu Arg Arg Tyr Leu Leu Lys Leu Ile
    50                  55

<210> SEQ ID NO 4
<211> LENGTH: 58
<212> TYPE: PRT
<213> ORGANISM: Clostridium thermocellum

<400> SEQUENCE: 4

Asp Ile Asn Leu Asp Gly Lys Ile Asn Ser Thr Asp Leu Ser Ala Leu
1               5                   10                  15

Lys Arg His Ile Leu Arg Ile Thr Thr Leu Ser Gly Lys Gln Leu Glu
            20                  25                  30

Asn Ala Asp Val Asn Asn Asp Gly Ser Val Asn Ser Thr Asp Ala Ser
        35                  40                  45

Ile Leu Lys Lys Tyr Ile Ala Lys Ala Ile
    50                  55

<210> SEQ ID NO 5
<211> LENGTH: 24
<212> TYPE: PRT
<213> ORGANISM: Clostridium thermocellum

<400> SEQUENCE: 5

Asp Phe Asn Ser Asp Ser Ser Val Asn Ser Thr Asp Leu Met Ile Leu
1               5                   10                  15

Asn Arg Ala Val Leu Gly Leu Gly
            20
```

<210> SEQ ID NO 6
<211> LENGTH: 57
<212> TYPE: PRT
<213> ORGANISM: Clostridium thermocellum

<400> SEQUENCE: 6

Glu Leu Asn Gly Asp Gly Lys Ile Asn Ser Ser Asp Leu Asn Met Met
1               5                   10                  15

Lys Arg Tyr Leu Leu Arg Leu Ile Asp Gly Leu Asn Asp Thr Ala Cys
            20                  25                  30

Ala Asp Leu Asn Gly Asp Gly Lys Ile Asn Ser Ser Asp Tyr Ser Ile
        35                  40                  45

Leu Lys Arg Tyr Leu Leu Arg Met Ile
    50                  55

<210> SEQ ID NO 7
<211> LENGTH: 59
<212> TYPE: PRT
<213> ORGANISM: Clostridium thermocellum

<400> SEQUENCE: 7

Asp Leu Asn Gly Asp Ala Lys Ile Asn Ser Thr Asp Leu Asn Met Met
1               5                   10                  15

Lys Arg Tyr Leu Leu Gln Met Ile Asp Arg Phe Gly Val Asp Asp Glu
            20                  25                  30

Ser Cys Ala Asp Leu Asn Gly Asp Gly Lys Ile Thr Ser Ser Asp Tyr
        35                  40                  45

Asn Leu Leu Lys Arg Tyr Ile Leu His Leu Ile
    50                  55

<210> SEQ ID NO 8
<211> LENGTH: 59
<212> TYPE: PRT
<213> ORGANISM: Clostridium thermocellum

<400> SEQUENCE: 8

Asp Val Asn Gly Asp Gly His Val Asn Ser Ser Asp Tyr Ser Leu Phe
1               5                   10                  15

Lys Arg Tyr Leu Leu Arg Val Ile Asp Arg Phe Pro Val Gly Asp Gln
            20                  25                  30

Ser Val Ala Asp Val Asn Arg Asp Gly Arg Ile Asp Ser Thr Asp Leu
        35                  40                  45

Thr Met Leu Lys Arg Tyr Leu Ile Arg Ala Ile
    50                  55

<210> SEQ ID NO 9
<211> LENGTH: 59
<212> TYPE: PRT
<213> ORGANISM: Clostridium thermocellum

<400> SEQUENCE: 9

Gly Asp Tyr Asn Gly Asp Gly Ala Val Asn Ser Thr Asp Leu Leu Ala
1               5                   10                  15

Cys Lys Arg Tyr Leu Leu Tyr Ala Leu Lys Pro Glu Gln Ile Asn Val
            20                  25                  30

Ile Ala Gly Asp Leu Asp Gly Asn Gly Lys Ile Asn Ser Thr Asp Tyr
        35                  40                  45

Ala Tyr Leu Lys Arg Tyr Leu Leu Lys Gln Ile

<210> SEQ ID NO 10
<211> LENGTH: 60
<212> TYPE: PRT
<213> ORGANISM: Clostridium thermocellum

<400> SEQUENCE: 10

```
Asp Leu Asn Ala Asp Gly Lys Ile Asn Ser Thr Asp Tyr Asn Leu Gly
1               5                   10                  15
Lys Arg Leu Ile Leu Arg Thr Ile Ser Glu Leu Pro Ile Ser Asn Gly
                20                  25                  30
Ser Val Ala Phe Asp Leu Asn Gly Asp Ser Lys Val Asp Ser Thr Asp
            35                  40                  45
Leu Thr Ala Leu Lys Arg Tyr Leu Leu Gly Val Ile
        50                  55                  60
```

<210> SEQ ID NO 11
<211> LENGTH: 59
<212> TYPE: PRT
<213> ORGANISM: Clostridium thermocellum

<400> SEQUENCE: 11

```
Asp Val Asn Gly Asp Ser Lys Ile Asn Ala Ile Asp Val Leu Leu Met
1               5                   10                  15
Lys Lys Tyr Ile Leu Lys Val Ile Asn Asp Leu Pro Ser Asp Gly Val
                20                  25                  30
Lys Ala Ala Asp Val Asn Ala Asp Gly Gln Ile Asn Ser Ile Asp Phe
            35                  40                  45
Thr Trp Leu Lys Lys Tyr Met Leu Lys Ala Val
        50                  55
```

<210> SEQ ID NO 12
<211> LENGTH: 56
<212> TYPE: PRT
<213> ORGANISM: Clostridium thermocellum

<400> SEQUENCE: 12

```
Asp Val Asn Gly Asp Gly Asn Val Asn Ser Thr Asp Leu Thr Met Leu
1               5                   10                  15
Lys Arg Tyr Leu Leu Lys Ser Val Thr Asn Ile Asn Arg Glu Ala Ala
                20                  25                  30
Asp Val Asn Arg Asp Gly Ala Ile Asn Ser Ser Asp Met Thr Ile Leu
            35                  40                  45
Lys Arg Tyr Leu Ile Lys Ser Ile
        50                  55
```

<210> SEQ ID NO 13
<211> LENGTH: 60
<212> TYPE: PRT
<213> ORGANISM: Clostridium thermocellum

<400> SEQUENCE: 13

```
Asp Leu Asn Gly Asp Gly Lys Val Asn Ser Ser Asp Leu Ala Ile Leu
1               5                   10                  15
Lys Arg Tyr Met Leu Arg Ala Ile Ser Asp Phe Pro Ile Pro Glu Gly
                20                  25                  30
Arg Lys Leu Ala Asp Leu Asn Arg Asp Gly Asn Val Asn Ser Thr Asp
            35                  40                  45
```

```
Tyr Ser Ile Leu Lys Arg Tyr Ile Leu Lys Ala Ile
    50                  55                  60

<210> SEQ ID NO 14
<211> LENGTH: 68
<212> TYPE: PRT
<213> ORGANISM: Clostridium thermocellum

<400> SEQUENCE: 14

Cys Asp Val Gly Asp Leu Asn Val Asp Gly Ser Ile Asn Ser Val Asp
1               5                   10                  15

Ile Thr Tyr Met Lys Arg Tyr Leu Leu Arg Ser Ile Ser Val Leu Pro
            20                  25                  30

Tyr Gln Glu Asn Glu Arg Ile Arg Ile Pro Ala Ala Asp Thr Asn Gly
        35                  40                  45

Asp Gly Ala Ile Asn Ser Ser Asp Met Val Leu Leu Lys Arg Tyr Val
    50                  55                  60

Leu Arg Ser Ile
65

<210> SEQ ID NO 15
<211> LENGTH: 60
<212> TYPE: PRT
<213> ORGANISM: Clostridium thermocellum

<400> SEQUENCE: 15

Asp Val Asn Gly Asp Gly Asn Val Asn Ser Thr Asp Val Val Trp Leu
1               5                   10                  15

Arg Arg Phe Leu Leu Lys Leu Val Glu Asp Phe Pro Val Pro Ser Gly
            20                  25                  30

Lys Gln Ala Ala Asp Met Asn Asp Asp Gly Asn Ile Asn Ser Thr Asp
        35                  40                  45

Met Ile Ala Leu Lys Arg Lys Val Leu Lys Ile Pro
    50                  55                  60

<210> SEQ ID NO 16
<211> LENGTH: 56
<212> TYPE: PRT
<213> ORGANISM: Clostridium thermocellum

<400> SEQUENCE: 16

Asp Cys Asn Gly Asp Gly Lys Val Asn Ser Thr Asp Ala Val Ala Leu
1               5                   10                  15

Lys Arg Tyr Ile Leu Arg Ser Gly Ile Ser Ile Asn Thr Asp Asn Ala
            20                  25                  30

Asp Val Asn Ala Asp Gly Arg Val Asn Ser Thr Asp Leu Ala Ile Leu
        35                  40                  45

Lys Arg Tyr Ile Leu Lys Glu Ile
    50                  55

<210> SEQ ID NO 17
<211> LENGTH: 56
<212> TYPE: PRT
<213> ORGANISM: Clostridium thermocellum

<400> SEQUENCE: 17

Asp Cys Asn Asp Asp Gly Lys Val Asn Ser Thr Asp Val Ala Val Met
1               5                   10                  15

Lys Arg Tyr Leu Lys Lys Glu Asn Val Asn Ile Asn Leu Asp Asn Ala
            20                  25                  30
```

```
Asp Val Asn Ala Asp Gly Lys Val Asn Ser Thr Asp Phe Ser Ile Leu
            35                  40                  45

Lys Arg Tyr Val Met Lys Asn Ile
     50                  55

<210> SEQ ID NO 18
<211> LENGTH: 58
<212> TYPE: PRT
<213> ORGANISM: Clostridium thermocellum

<400> SEQUENCE: 18

Asp Leu Asn Gly Asp Gly Arg Val Asn Ser Ser Asp Leu Ala Leu Met
1               5                   10                  15

Lys Arg Tyr Val Val Lys Gln Ile Glu Lys Leu Asn Val Pro Val Lys
            20                  25                  30

Ala Ala Asp Leu Asn Gly Asp Asp Lys Val Asn Ser Thr Asp Tyr Ser
            35                  40                  45

Val Leu Lys Arg Tyr Leu Leu Arg Ser Ile
     50                  55

<210> SEQ ID NO 19
<211> LENGTH: 60
<212> TYPE: PRT
<213> ORGANISM: Clostridium thermocellum

<400> SEQUENCE: 19

Asp Val Asn Ala Asp Gly Val Val Asn Ile Ser Asp Tyr Val Leu Met
1               5                   10                  15

Lys Arg Tyr Ile Leu Arg Ile Ile Ala Asp Phe Pro Ala Asp Asp Asp
            20                  25                  30

Met Trp Val Gly Asp Val Asn Gly Asp Asn Val Ile Asn Asp Ile Asp
            35                  40                  45

Cys Asn Tyr Leu Lys Arg Tyr Leu Leu His Met Ile
     50                  55                  60

<210> SEQ ID NO 20
<211> LENGTH: 24
<212> TYPE: PRT
<213> ORGANISM: Clostridium thermocellum

<400> SEQUENCE: 20

Asp Leu Asn Gly Asp Asn Asn Ile Asn Ser Ser Asp Tyr Thr Leu Leu
1               5                   10                  15

Lys Arg Tyr Leu Leu His Thr Ile
            20

<210> SEQ ID NO 21
<211> LENGTH: 56
<212> TYPE: PRT
<213> ORGANISM: Clostridium thermocellum

<400> SEQUENCE: 21

Asp Val Asn Gly Asp Gly Arg Val Asn Ser Asp Val Ala Leu Leu
1               5                   10                  15

Lys Arg Tyr Leu Leu Gly Leu Val Glu Asn Ile Asn Lys Glu Ala Ala
            20                  25                  30

Asp Val Asn Val Ser Gly Thr Val Asn Ser Thr Asp Leu Ala Ile Met
            35                  40                  45

Lys Arg Tyr Val Leu Arg Ser Ile
```

```
            50                  55

<210> SEQ ID NO 22
<211> LENGTH: 63
<212> TYPE: PRT
<213> ORGANISM: Clostridium thermocellum

<400> SEQUENCE: 22

Asp Val Asn Phe Asp Gly Arg Ile Asn Ser Thr Asp Tyr Ser Arg Leu
1               5                   10                  15

Lys Arg Tyr Val Ile Lys Ser Leu Glu Phe Thr Asp Pro Glu Glu His
            20                  25                  30

Gln Lys Phe Ile Ala Ala Ala Asp Val Asp Gly Asn Gly Arg Ile Asn
        35                  40                  45

Ser Thr Asp Leu Tyr Val Leu Asn Arg Tyr Ile Leu Lys Leu Ile
    50                  55                  60

<210> SEQ ID NO 23
<211> LENGTH: 63
<212> TYPE: PRT
<213> ORGANISM: Clostridium thermocellum

<400> SEQUENCE: 23

Asp Ile Asn Leu Asp Gly Lys Ile Asn Ser Ser Asp Val Thr Leu Leu
1               5                   10                  15

Lys Arg Tyr Ile Val Lys Ser Ile Asp Val Phe Pro Thr Ala Asp Pro
            20                  25                  30

Glu Arg Ser Leu Ile Ala Ser Asp Val Asn Gly Asp Gly Arg Val Asn
        35                  40                  45

Ser Thr Asp Tyr Ser Tyr Leu Lys Arg Tyr Val Leu Lys Ile Ile
    50                  55                  60

<210> SEQ ID NO 24
<211> LENGTH: 60
<212> TYPE: PRT
<213> ORGANISM: Clostridium thermocellum

<400> SEQUENCE: 24

Asp Leu Asn Gly Asp Asn Asn Val Asn Ser Thr Asp Leu Thr Leu Leu
1               5                   10                  15

Lys Arg Tyr Leu Thr Arg Val Ile Asn Asp Phe Pro His Pro Asp Gly
            20                  25                  30

Ser Val Asn Ala Asp Val Asn Gly Asp Gly Lys Ile Asn Ser Thr Asp
        35                  40                  45

Tyr Ser Ala Met Ile Arg Tyr Ile Leu Arg Ile Ile
    50                  55                  60

<210> SEQ ID NO 25
<211> LENGTH: 60
<212> TYPE: PRT
<213> ORGANISM: Clostridium thermocellum

<400> SEQUENCE: 25

Asp Val Asn Gly Asp Leu Lys Val Asn Ser Thr Asp Phe Ser Met Leu
1               5                   10                  15

Arg Arg Tyr Leu Leu Lys Thr Ile Asp Asn Phe Pro Thr Glu Asn Gly
            20                  25                  30

Lys Gln Ala Ala Asp Leu Asn Gly Asp Gly Arg Ile Asn Ser Ser Asp
        35                  40                  45
```

```
Leu Thr Met Leu Lys Arg Tyr Leu Leu Met Glu Val
    50                  55                  60

<210> SEQ ID NO 26
<211> LENGTH: 56
<212> TYPE: PRT
<213> ORGANISM: Clostridium thermocellum

<400> SEQUENCE: 26

Asp Leu Asn Asn Asp Ser Lys Val Asn Ala Val Asp Ile Met Met Leu
1               5                   10                  15

Lys Arg Tyr Ile Leu Gly Ile Ile Asp Asn Ile Asn Leu Thr Ala Ala
            20                  25                  30

Asp Ile Tyr Phe Asp Gly Val Val Asn Ser Ser Asp Tyr Asn Ile Met
        35                  40                  45

Lys Arg Tyr Leu Leu Lys Ala Ile
    50                  55

<210> SEQ ID NO 27
<211> LENGTH: 59
<212> TYPE: PRT
<213> ORGANISM: Clostridium thermocellum

<400> SEQUENCE: 27

Asp Leu Asn Gly Asp Gly Val Val Asn Ser Thr Asp Ser Val Ile Leu
1               5                   10                  15

Lys Arg His Ile Ile Lys Phe Ser Glu Ile Thr Asp Pro Val Lys Leu
            20                  25                  30

Lys Ala Ala Asp Leu Asn Gly Asp Gly Asn Ile Asn Ser Ser Asp Val
        35                  40                  45

Ser Leu Met Lys Arg Tyr Leu Leu Arg Ile Ile
    50                  55

<210> SEQ ID NO 28
<211> LENGTH: 60
<212> TYPE: PRT
<213> ORGANISM: Clostridium thermocellum

<400> SEQUENCE: 28

Asp Leu Asn Gly Asp Gly Lys Ile Asn Ser Thr Asp Ile Ser Leu Met
1               5                   10                  15

Lys Arg Tyr Leu Leu Lys Gln Ile Val Asp Leu Pro Val Glu Asp Asp
            20                  25                  30

Ile Lys Ala Ala Asp Ile Asn Lys Asp Gly Lys Val Asn Ser Thr Asp
        35                  40                  45

Met Ser Ile Leu Lys Arg Val Ile Leu Arg Asn Tyr
    50                  55                  60

<210> SEQ ID NO 29
<211> LENGTH: 57
<212> TYPE: PRT
<213> ORGANISM: Clostridium thermocellum

<400> SEQUENCE: 29

Asp Ser Asn Ser Asp Cys Lys Val Asn Ser Thr Asp Leu Thr Leu Met
1               5                   10                  15

Lys Arg Tyr Leu Leu Gln Gln Ser Ile Ser Tyr Ile Asn Leu Ile Asn
            20                  25                  30

Ala Asp Leu Asn Gly Asp Gly Lys Ile Asn Ser Ser Asp Tyr Thr Leu
        35                  40                  45
```

```
Leu Lys Arg Tyr Leu Leu Gly Tyr Ile
    50                  55
```

```
<210> SEQ ID NO 30
<211> LENGTH: 57
<212> TYPE: PRT
<213> ORGANISM: Clostridium thermocellum

<400> SEQUENCE: 30

Asp Ile Asn Asn Asp Lys Thr Val Asn Ser Thr Asp Val Thr Tyr Leu
1               5                   10                  15

Lys Arg Phe Leu Leu Lys Gln Ile Asn Ser Leu Pro Asn Gln Lys Ala
            20                  25                  30

Ala Asp Val Asn Leu Asp Gly Asn Ile Asn Ser Thr Asp Leu Val Ile
        35                  40                  45

Leu Lys Arg Tyr Val Leu Arg Gly Ile
    50                  55
```

```
<210> SEQ ID NO 31
<211> LENGTH: 60
<212> TYPE: PRT
<213> ORGANISM: Clostridium thermocellum

<400> SEQUENCE: 31

Asp Val Asn Gly Asp Gly Lys Ile Asn Ser Thr Asp Cys Thr Met Leu
1               5                   10                  15

Lys Arg Tyr Ile Leu Arg Gly Ile Glu Glu Phe Pro Ser Pro Ser Gly
            20                  25                  30

Ile Ile Ala Ala Asp Val Asn Ala Asp Leu Lys Ile Asn Ser Thr Asp
        35                  40                  45

Leu Val Leu Met Lys Lys Tyr Leu Leu Arg Ser Ile
    50                  55                  60
```

```
<210> SEQ ID NO 32
<211> LENGTH: 57
<212> TYPE: PRT
<213> ORGANISM: Clostridium thermocellum

<400> SEQUENCE: 32

Asp Val Asn Leu Asp Gly Gln Val Asn Ser Thr Asp Phe Ser Leu Leu
1               5                   10                  15

Lys Arg Tyr Ile Leu Lys Val Val Asp Ile Asn Ser Ile Asn Val Thr
            20                  25                  30

Asn Ala Asp Met Asn Asn Asp Gly Asn Ile Asn Ser Thr Asp Ile Ser
        35                  40                  45

Ile Leu Lys Arg Ile Leu Leu Arg Asn
    50                  55
```

```
<210> SEQ ID NO 33
<211> LENGTH: 59
<212> TYPE: PRT
<213> ORGANISM: Clostridium thermocellum

<400> SEQUENCE: 33

Asp Ile Asn Arg Asp Gly Lys Ile Asn Ser Thr Asp Leu Gly Met Leu
1               5                   10                  15

Asn Arg His Ile Leu Lys Leu Val Ile Leu Asp Asp Asn Leu Lys Leu
            20                  25                  30

Ala Ala Ala Asp Ile Asp Gly Asn Gly Asn Ile Asn Ser Thr Asp Tyr
```

```
             35                  40                  45

Ser Trp Leu Lys Lys Tyr Ile Leu Lys Val Ile
    50                  55

<210> SEQ ID NO 34
<211> LENGTH: 60
<212> TYPE: PRT
<213> ORGANISM: Clostridium thermocellum

<400> SEQUENCE: 34

Asp Val Asn Asp Gly Lys Val Asn Ser Thr Asp Leu Thr Leu Leu
1               5                   10                  15

Lys Arg Tyr Val Leu Lys Ala Val Ser Thr Leu Pro Ser Ser Lys Ala
            20                  25                  30

Glu Lys Asn Ala Asp Val Asn Arg Asp Gly Arg Val Asn Ser Ser Asp
        35                  40                  45

Val Thr Ile Leu Ser Arg Tyr Leu Ile Arg Val Ile
    50                  55                  60

<210> SEQ ID NO 35
<211> LENGTH: 58
<212> TYPE: PRT
<213> ORGANISM: Clostridium thermocellum

<400> SEQUENCE: 35

Asp Val Asn Gly Asp Gly Thr Ile Asn Ser Thr Asp Leu Thr Met Leu
1               5                   10                  15

Lys Arg Ser Val Leu Arg Ala Ile Thr Leu Thr Asp Asp Ala Lys Ala
            20                  25                  30

Arg Ala Asp Val Asp Lys Asn Gly Ser Ile Asn Ser Thr Asp Val Leu
        35                  40                  45

Leu Leu Ser Arg Tyr Leu Leu Arg Val Ile
    50                  55

<210> SEQ ID NO 36
<211> LENGTH: 57
<212> TYPE: PRT
<213> ORGANISM: Clostridium thermocellum

<400> SEQUENCE: 36

Asp Leu Asn Arg Asn Gly Ile Val Asn Asp Glu Asp Tyr Ile Leu Leu
1               5                   10                  15

Lys Asn Tyr Leu Leu Arg Gly Asn Lys Leu Val Ile Asp Leu Asn Val
            20                  25                  30

Ala Asp Val Asn Lys Asp Gly Lys Val Asn Ser Thr Asp Cys Leu Phe
        35                  40                  45

Leu Lys Lys Tyr Ile Leu Gly Leu Ile
    50                  55

<210> SEQ ID NO 37
<211> LENGTH: 58
<212> TYPE: PRT
<213> ORGANISM: Clostridium thermocellum

<400> SEQUENCE: 37

Asp Thr Asn Ser Asp Gly Lys Ile Asn Ser Thr Asp Val Thr Ala Leu
1               5                   10                  15

Lys Arg His Leu Leu Arg Val Thr Gln Leu Thr Gly Asp Asn Leu Ala
            20                  25                  30
```

Asn Ala Asp Val Asn Gly Asp Gly Asn Val Asn Ser Thr Asp Leu Leu
         35                  40                  45

Leu Leu Lys Arg Tyr Ile Leu Gly Glu Ile
 50                  55

<210> SEQ ID NO 38
<211> LENGTH: 60
<212> TYPE: PRT
<213> ORGANISM: Clostridium thermocellum

<400> SEQUENCE: 38

Asp Leu Asn Gly Asp Asn Arg Ile Asn Ser Thr Asp Leu Thr Leu Met
 1               5                  10                  15

Lys Arg Tyr Ile Leu Lys Ser Ile Glu Asp Leu Pro Val Glu Asp Asp
             20                  25                  30

Leu Trp Ala Ala Asp Ile Asn Gly Asp Gly Lys Ile Asn Ser Thr Asp
         35                  40                  45

Tyr Thr Tyr Leu Lys Lys Tyr Leu Leu Gln Ala Ile
 50                  55                  60

<210> SEQ ID NO 39
<211> LENGTH: 60
<212> TYPE: PRT
<213> ORGANISM: Clostridium thermocellum

<400> SEQUENCE: 39

Asp Leu Asn Gly Asp Gly Arg Val Asn Ser Thr Asp Tyr Thr Leu Leu
 1               5                  10                  15

Lys Arg Tyr Leu Leu Gly Ala Ile Gln Thr Phe Pro Tyr Glu Arg Gly
             20                  25                  30

Ile Lys Ala Ala Asp Leu Asn Leu Asp Gly Arg Ile Asn Ser Thr Asp
         35                  40                  45

Tyr Thr Val Leu Lys Arg Tyr Leu Leu Asn Ala Ile
 50                  55                  60

<210> SEQ ID NO 40
<211> LENGTH: 63
<212> TYPE: PRT
<213> ORGANISM: Clostridium thermocellum

<400> SEQUENCE: 40

Asp Leu Asn Phe Asp Asn Ala Val Asn Ser Thr Asp Leu Leu Met Leu
 1               5                  10                  15

Lys Arg Tyr Ile Leu Lys Ser Leu Glu Leu Gly Thr Ser Glu Gln Glu
             20                  25                  30

Glu Lys Phe Lys Lys Ala Ala Asp Leu Asn Arg Asp Asn Lys Val Asp
         35                  40                  45

Ser Thr Asp Leu Thr Ile Leu Lys Arg Tyr Leu Leu Lys Ala Ile
 50                  55                  60

<210> SEQ ID NO 41
<211> LENGTH: 77
<212> TYPE: PRT
<213> ORGANISM: Clostridium thermocellum

<400> SEQUENCE: 41

Glu Val Ile Asp Thr Lys Val Ile Asp Ser Asp Asp Ile Val Lys
 1               5                  10                  15

Tyr Glu Tyr Gln Phe Asp Lys Lys Ile Leu Cys Ala Asp Lys Glu Thr
             20                  25                  30

Glu Ile Leu Tyr Phe Thr Val Ala Asp Glu Glu Ile Tyr Thr
                35                  40                  45

Ser Asp Asn Thr Arg Thr Leu Val Leu Ser Val Asn Asn Asp Ser Thr
 50                  55                  60

Asp Lys Thr Thr Val Ser Gly Tyr Ile Ser Val Asp Phe
 65                  70                  75

<210> SEQ ID NO 42
<211> LENGTH: 60
<212> TYPE: PRT
<213> ORGANISM: Clostridium thermocellum

<400> SEQUENCE: 42

Asp Val Asn Gly Asp Gly Arg Val Asn Ser Asp Leu Thr Leu Met
 1               5                  10                  15

Lys Arg Tyr Leu Leu Lys Ser Ile Ser Asp Phe Pro Thr Pro Glu Gly
                20                  25                  30

Lys Ile Ala Ala Asp Leu Asn Glu Asp Gly Lys Val Asn Ser Thr Asp
                35                  40                  45

Leu Leu Ala Leu Lys Lys Leu Val Leu Arg Glu Leu
 50                  55                  60

<210> SEQ ID NO 43
<211> LENGTH: 56
<212> TYPE: PRT
<213> ORGANISM: Clostridium thermocellum

<400> SEQUENCE: 43

Asp Leu Asn Ala Asp Gly Ser Ile Asn Ser Thr Asp Leu Met Ile Met
 1               5                  10                  15

Lys Arg Val Leu Leu Lys Gln Arg Thr Leu Asp Asp Ile Thr Pro Ala
                20                  25                  30

Asp Leu Asn Gly Asp Gly Lys Val Thr Ser Thr Asp Tyr Ser Leu Met
                35                  40                  45

Lys Arg Tyr Leu Leu Lys Glu Ile
 50                  55

<210> SEQ ID NO 44
<211> LENGTH: 58
<212> TYPE: PRT
<213> ORGANISM: Clostridium thermocellum

<400> SEQUENCE: 44

Asp Leu Asn Gly Asp Gly Asn Ile Asn Ser Ser Asp Leu Gln Ala Leu
 1               5                  10                  15

Lys Arg His Leu Leu Gly Ile Ser Pro Leu Thr Gly Glu Ala Leu Leu
                20                  25                  30

Arg Ala Asp Val Asn Arg Ser Gly Lys Val Asp Ser Thr Asp Tyr Ser
                35                  40                  45

Val Leu Lys Arg Tyr Ile Leu Arg Ile Ile
 50                  55

<210> SEQ ID NO 45
<211> LENGTH: 58
<212> TYPE: PRT
<213> ORGANISM: Clostridium thermocellum

<400> SEQUENCE: 45

Asp Ile Val Leu Asp Gly Asn Ile Asn Ser Leu Asp Met Met Lys Leu

```
                1               5                  10                 15
Lys Lys Tyr Leu Ile Arg Glu Thr Gln Phe Asn Tyr Asp Glu Leu Leu
                20                 25                 30

Arg Ala Asp Val Asn Ser Asp Gly Glu Val Asn Ser Thr Asp Tyr Ala
       35                 40                 45

Tyr Leu Lys Arg Tyr Ile Leu Arg Ile Ile
   50                 55

<210> SEQ ID NO 46
<211> LENGTH: 56
<212> TYPE: PRT
<213> ORGANISM: Clostridium thermocellum

<400> SEQUENCE: 46

Asp Val Asn Asp Asp Gly Lys Val Asn Ser Thr Asp Ala Val Ala Leu
1               5                  10                 15

Lys Arg Tyr Val Leu Arg Ser Gly Ile Ser Ile Asn Thr Asp Asn Ala
                20                 25                 30

Asp Leu Asn Glu Asp Gly Arg Val Asn Ser Thr Asp Leu Gly Ile Leu
       35                 40                 45

Lys Arg Tyr Ile Leu Lys Glu Ile
   50                 55

<210> SEQ ID NO 47
<211> LENGTH: 60
<212> TYPE: PRT
<213> ORGANISM: Clostridium thermocellum

<400> SEQUENCE: 47

Asp Val Asp Gly Asn Gly Thr Val Asn Ser Thr Asp Val Asn Tyr Met
1               5                  10                 15

Lys Arg Tyr Leu Leu Arg Gln Ile Glu Glu Phe Pro Tyr Glu Lys Ala
                20                 25                 30

Leu Met Ala Gly Asp Val Asp Gly Asn Gly Asn Ile Asn Ser Thr Asp
       35                 40                 45

Leu Ser Tyr Leu Lys Lys Tyr Ile Leu Lys Leu Ile
   50                 55                 60

<210> SEQ ID NO 48
<211> LENGTH: 58
<212> TYPE: PRT
<213> ORGANISM: Clostridium thermocellum

<400> SEQUENCE: 48

Asp Val Asn Ala Asp Gly Val Ile Asn Ser Ser Asp Ile Met Val Leu
1               5                  10                 15

Lys Arg Phe Leu Leu Arg Thr Ile Thr Leu Thr Glu Glu Met Leu Leu
                20                 25                 30

Asn Ala Asp Thr Asn Gly Asp Gly Ala Val Asn Ser Ser Asp Phe Thr
       35                 40                 45

Leu Leu Lys Arg Tyr Ile Leu Arg Ser Ile
   50                 55

<210> SEQ ID NO 49
<211> LENGTH: 60
<212> TYPE: PRT
<213> ORGANISM: Clostridium thermocellum

<400> SEQUENCE: 49
```

-continued

```
Asp Val Asn Gly Asp Phe Ala Val Asn Ser Asn Asp Leu Thr Leu Ile
1               5                   10                  15

Lys Arg Tyr Val Leu Lys Asn Ile Asp Glu Phe Pro Ser Ser His Gly
            20                  25                  30

Leu Lys Ala Ala Asp Val Asp Gly Asp Glu Lys Ile Thr Ser Ser Asp
        35                  40                  45

Ala Ala Leu Val Lys Arg Tyr Val Leu Arg Ala Ile
    50                  55                  60

<210> SEQ ID NO 50
<211> LENGTH: 58
<212> TYPE: PRT
<213> ORGANISM: Clostridium thermocellum

<400> SEQUENCE: 50

Asp Leu Asn Gly Asp Gly Asn Val Asn Ser Thr Asp Ser Ile Leu Met
1               5                   10                  15

Lys Arg Tyr Leu Met Lys Ser Val Asp Leu Asn Glu Glu Gln Leu Lys
            20                  25                  30

Ala Ala Asp Val Asn Leu Asp Gly Arg Val Asn Ser Thr Asp Arg Ser
        35                  40                  45

Ile Leu Asn Arg Tyr Leu Leu Lys Ile Ile
    50                  55

<210> SEQ ID NO 51
<211> LENGTH: 58
<212> TYPE: PRT
<213> ORGANISM: Clostridium thermocellum

<400> SEQUENCE: 51

Asp Ile Asn Asp Asp Gly Asn Ile Asn Ser Thr Asp Leu Gln Met Leu
1               5                   10                  15

Lys Arg His Leu Leu Arg Ser Ile Arg Leu Thr Glu Lys Gln Leu Leu
            20                  25                  30

Asn Ala Asp Thr Asn Arg Asp Gly Arg Val Asp Ser Thr Asp Leu Ala
        35                  40                  45

Leu Leu Lys Arg Tyr Ile Leu Arg Val Ile
    50                  55

<210> SEQ ID NO 52
<211> LENGTH: 58
<212> TYPE: PRT
<213> ORGANISM: Clostridium thermocellum

<400> SEQUENCE: 52

Asp Leu Asn Gly Asp Gly Asn Ile Asn Ser Thr Asp Leu Gln Ile Leu
1               5                   10                  15

Lys Lys His Leu Leu Arg Ile Thr Leu Leu Thr Gly Lys Glu Leu Ser
            20                  25                  30

Asn Ala Asp Val Thr Lys Asp Gly Lys Val Asp Ser Thr Asp Leu Thr
        35                  40                  45

Leu Leu Lys Arg Tyr Ile Leu Arg Phe Val
    50                  55

<210> SEQ ID NO 53
<211> LENGTH: 58
<212> TYPE: PRT
<213> ORGANISM: Clostridium thermocellum

<400> SEQUENCE: 53
```

Asp Leu Asn Asp Gly Lys Val Asn Ser Thr Asp Phe Gln Ile Leu
1               5                   10                  15

Lys Lys His Leu Leu Arg Ile Thr Leu Thr Gly Lys Asn Leu Ser
                20                  25                  30

Asn Ala Asp Leu Asn Lys Asp Gly Lys Val Asp Ser Ser Asp Leu Ser
            35                  40                  45

Leu Met Lys Arg Tyr Leu Leu Gln Ile Ile
    50                  55

<210> SEQ ID NO 54
<211> LENGTH: 58
<212> TYPE: PRT
<213> ORGANISM: Clostridium thermocellum

<400> SEQUENCE: 54

Asp Leu Asn Asn Asp Gly Lys Val Asn Ser Thr Asp Phe Gln Leu Leu
1               5                   10                  15

Lys Met His Val Leu Arg Gln Glu Leu Pro Ala Gly Thr Asp Leu Ser
                20                  25                  30

Asn Ala Asp Val Asn Arg Asp Gly Lys Val Asp Ser Ser Asp Cys Thr
            35                  40                  45

Leu Leu Lys Arg Tyr Ile Leu Arg Val Ile
    50                  55

<210> SEQ ID NO 55
<211> LENGTH: 58
<212> TYPE: PRT
<213> ORGANISM: Clostridium thermocellum

<400> SEQUENCE: 55

Asp Leu Asn Gly Asp Gly Lys Val Asn Ser Thr Asp Leu Gln Leu Met
1               5                   10                  15

Lys Met His Val Leu Arg Gln Arg Gln Leu Thr Gly Thr Ser Leu Leu
                20                  25                  30

Asn Ala Asp Val Asn Arg Asp Gly Lys Val Asp Ser Thr Asp Val Ala
            35                  40                  45

Leu Leu Lys Arg Tyr Ile Leu Arg Gln Ile
    50                  55

<210> SEQ ID NO 56
<211> LENGTH: 130
<212> TYPE: PRT
<213> ORGANISM: Clostridium thermocellum

<400> SEQUENCE: 56

Asp Val Asn Leu Asp Gly Ser Val Asp Ser Ile Asp Leu Ala Leu Leu
1               5                   10                  15

Tyr Asn Thr Thr Tyr Tyr Ala Val Pro Leu Pro Asn Arg Leu Gln Tyr
                20                  25                  30

Ile Ala Ala Asp Val Asn Tyr Asp Ser Ser Cys Thr Met Leu Asp Phe
            35                  40                  45

Tyr Met Leu Glu Asp Tyr Leu Leu Gly Arg Ile Ser Ser Phe Pro Ala
    50                  55                  60

Gly Gln Thr Tyr Thr Val Tyr Tyr Gly Asp Leu Asn Gly Asp Gln Leu
65                  70                  75                  80

Val Thr Thr Asp Gln Ser Leu Leu Ser Asp Tyr Leu Leu Gly Arg Ile
                85                  90                  95

```
Asn Leu Thr Phe Arg Gln Tyr Val Ser Ala Asp Val Asn Gly Asp Gly
            100                 105                 110

Thr Val Asp Gly Ile Asp Leu Ala Ile Ile Thr Ala Tyr Ile Asn Gly
        115                 120                 125

Gln Ile
    130

<210> SEQ ID NO 57
<211> LENGTH: 58
<212> TYPE: PRT
<213> ORGANISM: Clostridium thermocellum

<400> SEQUENCE: 57

Asp Leu Asn Gly Asp Gly Arg Val Asn Ser Thr Asp Leu Leu Leu Met
1               5                   10                  15

Lys Lys Arg Ile Ile Arg Glu Ile Asp Lys Phe Asn Val Pro Asp Glu
            20                  25                  30

Asn Ala Asp Leu Asn Leu Asp Gly Lys Ile Asn Ser Ser Asp Tyr Thr
        35                  40                  45

Ile Leu Lys Arg Tyr Val Leu Lys Ser Ile
    50                  55

<210> SEQ ID NO 58
<211> LENGTH: 60
<212> TYPE: PRT
<213> ORGANISM: Clostridium thermocellum

<400> SEQUENCE: 58

Asp Val Asn Lys Asp Gly Arg Ile Asn Ser Thr Asp Ile Met Tyr Leu
1               5                   10                  15

Lys Gly Tyr Leu Leu Arg Asn Ser Ala Phe Asn Leu Asp Glu Tyr Gly
            20                  25                  30

Leu Met Ala Ala Asp Val Asp Gly Asn Gly Ser Val Ser Ser Leu Asp
        35                  40                  45

Leu Thr Tyr Leu Lys Arg Tyr Ile Leu Arg Arg Ile
    50                  55                  60

<210> SEQ ID NO 59
<211> LENGTH: 58
<212> TYPE: PRT
<213> ORGANISM: Clostridium thermocellum

<400> SEQUENCE: 59

Asp Leu Asn Gln Asp Gly Gln Val Ser Ser Thr Asp Leu Val Ala Met
1               5                   10                  15

Lys Arg Tyr Leu Leu Lys Asn Phe Glu Leu Ser Gly Val Gly Leu Glu
            20                  25                  30

Ala Ala Asp Leu Asn Ser Asp Gly Lys Val Asn Ser Thr Asp Leu Val
        35                  40                  45

Ala Leu Lys Arg Phe Leu Leu Lys Glu Ile
    50                  55

<210> SEQ ID NO 60
<211> LENGTH: 60
<212> TYPE: PRT
<213> ORGANISM: Clostridium thermocellum

<400> SEQUENCE: 60

Asp Leu Asn Tyr Asp Gly Lys Val Asn Ser Thr Asp Tyr Leu Val Leu
1               5                   10                  15
```

```
Lys Arg Tyr Leu Leu Gly Thr Ile Asp Lys Glu Ser Asp Pro Asn Phe
         20                  25                  30

Leu Lys Ala Ala Asp Leu Asn Arg Asp Gly Arg Val Asn Ser Thr Asp
         35                  40                  45

Met Ser Leu Met Lys Arg Tyr Leu Leu Gly Ile Ile
         50                  55                  60

<210> SEQ ID NO 61
<211> LENGTH: 60
<212> TYPE: PRT
<213> ORGANISM: Clostridium thermocellum

<400> SEQUENCE: 61

Asp Val Asn Gly Asp Gly Lys Val Asn Ser Thr Asp Cys Ser Ile Val
1               5                   10                  15

Lys Arg Tyr Leu Leu Lys Asn Ile Glu Asp Phe Pro Tyr Glu Tyr Gly
         20                  25                  30

Lys Glu Ala Gly Asp Val Asn Gly Asp Gly Lys Val Asn Ser Thr Asp
         35                  40                  45

Tyr Ser Leu Leu Lys Arg Phe Val Leu Arg Asn Ile
         50                  55                  60

<210> SEQ ID NO 62
<211> LENGTH: 58
<212> TYPE: PRT
<213> ORGANISM: Clostridium thermocellum

<400> SEQUENCE: 62

Asp Leu Asn Gly Asp Gly Lys Val Asn Ser Thr Asp Leu Thr Ile Met
1               5                   10                  15

Lys Arg Tyr Ile Leu Lys Asn Phe Asp Lys Leu Ala Val Pro Glu Glu
         20                  25                  30

Ala Ala Asp Leu Asn Gly Asp Gly Arg Ile Asn Ser Thr Asp Leu Ser
         35                  40                  45

Ile Leu His Arg Tyr Leu Leu Arg Ile Ile
         50                  55

<210> SEQ ID NO 63
<211> LENGTH: 52
<212> TYPE: PRT
<213> ORGANISM: Clostridium thermocellum

<400> SEQUENCE: 63

Asp Leu Asn Gly Asp Gln Lys Val Thr Ser Thr Asp Tyr Thr Met Leu
1               5                   10                  15

Lys Arg Tyr Leu Met Lys Ser Ile Asp Arg Phe Asn Thr Ser Glu Gln
         20                  25                  30

Ala Ala Asp Leu Asn Arg Asp Gly Lys Ile Asn Ser Thr Asp Leu Thr
         35                  40                  45

Ile Leu Lys Arg
         50

<210> SEQ ID NO 64
<211> LENGTH: 57
<212> TYPE: PRT
<213> ORGANISM: Clostridium thermocellum

<400> SEQUENCE: 64

Asp Ile Asn Ser Asp Gly Asn Val Asn Ser Thr Asp Leu Gly Ile Leu
```

```
              1               5                  10                 15
Lys Arg Ile Ile Val Lys Asn Pro Pro Ala Ser Ala Asn Met Asp Ala
                20                  25                 30

Ala Asp Val Asn Ala Asp Gly Lys Val Asn Ser Thr Asp Tyr Thr Val
                35                  40                 45

Leu Lys Arg Tyr Leu Leu Arg Ser Ile
                50                  55

<210> SEQ ID NO 65
<211> LENGTH: 58
<212> TYPE: PRT
<213> ORGANISM: Clostridium thermocellum

<400> SEQUENCE: 65

Asp Ile Asn Ser Asp Gly Ser Ile Asn Ser Thr Asp Val Thr Leu Leu
1               5                  10                 15

Lys Arg His Leu Leu Arg Glu Asn Ile Leu Thr Gly Thr Ala Tyr Ser
                20                  25                 30

Asn Ala Asp Thr Asp Gly Asp Gly Lys Ile Thr Ser Ile Asp Leu Ser
                35                  40                 45

Tyr Leu Lys Arg Tyr Val Leu Arg Leu Ile
                50                  55

<210> SEQ ID NO 66
<211> LENGTH: 58
<212> TYPE: PRT
<213> ORGANISM: Clostridium thermocellum

<400> SEQUENCE: 66

Asp Leu Asn Gly Asp Gly Leu Val Asn Ser Ser Asp Tyr Ser Leu Leu
1               5                  10                 15

Lys Arg Tyr Ile Leu Lys Gln Ile Asp Leu Thr Glu Glu Lys Leu Lys
                20                  25                 30

Ala Ala Asp Leu Asn Arg Asn Gly Ser Val Asp Ser Val Asp Tyr Ser
                35                  40                 45

Ile Leu Lys Arg Phe Leu Leu Lys Thr Ile
                50                  55

<210> SEQ ID NO 67
<211> LENGTH: 58
<212> TYPE: PRT
<213> ORGANISM: Clostridium thermocellum

<400> SEQUENCE: 67

Asp Leu Asn Asn Asp Gly Arg Thr Asn Ser Thr Asp Tyr Ser Leu Met
1               5                  10                 15

Lys Arg Tyr Leu Leu Gly Ser Ile Ser Phe Thr Asn Glu Gln Leu Lys
                20                  25                 30

Ala Ala Asp Val Asn Leu Asp Gly Lys Val Asn Ser Ser Asp Tyr Thr
                35                  40                 45

Val Leu Arg Arg Phe Leu Leu Gly Ser Ile
                50                  55

<210> SEQ ID NO 68
<211> LENGTH: 61
<212> TYPE: PRT
<213> ORGANISM: Clostridium thermocellum

<400> SEQUENCE: 68
```

```
Val Leu Gly Asp Leu Asn Gly Asp Lys Gln Val Asn Ser Thr Asp Tyr
1               5                   10                  15

Thr Ala Leu Lys Arg His Leu Leu Asn Ile Thr Arg Leu Ser Gly Thr
            20                  25                  30

Ala Leu Ala Asn Ala Asp Leu Asn Gly Asp Gly Lys Val Asp Ser Thr
        35                  40                  45

Asp Leu Met Ile Leu His Arg Tyr Leu Leu Gly Ile Ile
    50                  55                  60

<210> SEQ ID NO 69
<211> LENGTH: 58
<212> TYPE: PRT
<213> ORGANISM: Clostridium thermocellum

<400> SEQUENCE: 69

Asp Leu Asn Gly Asp Gly Asn Val Asn Ser Thr Asp Ser Thr Leu Met
1               5                   10                  15

Ser Arg Tyr Leu Leu Gly Ile Ile Thr Thr Leu Pro Ala Gly Glu Lys
            20                  25                  30

Ala Ala Asp Leu Asn Gly Asp Gly Lys Val Asn Ser Thr Asp Tyr Asn
        35                  40                  45

Ile Leu Lys Arg Tyr Leu Leu Lys Tyr Ile
    50                  55

<210> SEQ ID NO 70
<211> LENGTH: 56
<212> TYPE: PRT
<213> ORGANISM: Clostridium thermocellum

<400> SEQUENCE: 70

Asp Leu Asn Gly Asp Gly Arg Val Asn Ser Thr Asp Leu Ala Val Met
1               5                   10                  15

Lys Arg Tyr Leu Leu Lys Gln Val Gln Ile Ser Asp Ile Arg Pro Ala
            20                  25                  30

Asp Leu Asn Gly Asp Gly Lys Ala Asn Ser Thr Asp Tyr Gln Leu Leu
        35                  40                  45

Lys Arg Tyr Ile Leu Lys Thr Ile
    50                  55

<210> SEQ ID NO 71
<211> LENGTH: 62
<212> TYPE: PRT
<213> ORGANISM: Clostridium thermocellum

<400> SEQUENCE: 71

Asp Ile Asp Gly Asn Gly Glu Ile Ser Ser Ile Asp Tyr Ala Ile Leu
1               5                   10                  15

Lys Ser His Leu Ile Asn Ser Asn Leu Thr Phe Lys Gln Leu Ala Ala
            20                  25                  30

Ala Asp Val Asp Gly Asn Gly Tyr Val Asn Ser Ile Asp Leu Ala Ile
        35                  40                  45

Leu Gln Met Tyr Leu Leu Gly Lys Gly Gly Thr Ser Asp Ile
    50                  55                  60

<210> SEQ ID NO 72
<211> LENGTH: 60
<212> TYPE: PRT
<213> ORGANISM: Clostridium thermocellum

<400> SEQUENCE: 72
```

-continued

```
Asp Val Asn Gly Asn Gly Ser Ile Glu Ser Thr Asp Cys Val Trp Val
1               5                   10                  15

Lys Arg Tyr Leu Lys Gln Ile Asp Ser Phe Pro Asn Glu Asn Gly
            20                  25                  30

Ala Arg Ala Ala Asp Val Asn Gly Asn Gly Thr Ile Asp Ser Thr Asp
            35                  40                  45

Tyr Gln Leu Leu Lys Arg Phe Ile Leu Lys Val Ile
    50                  55                  60

<210> SEQ ID NO 73
<211> LENGTH: 24
<212> TYPE: PRT
<213> ORGANISM: Clostridium thermocellum

<400> SEQUENCE: 73

Asp Val Asn Ala Asp Gly Lys Ile Asp Ser Thr Asp Leu Thr Leu Leu
1               5                   10                  15

Lys Arg Tyr Leu Leu Arg Ser Ala
            20

<210> SEQ ID NO 74
<211> LENGTH: 24
<212> TYPE: PRT
<213> ORGANISM: Clostridium thermocellum

<400> SEQUENCE: 74

Asp Thr Asp Gly Asn Gly Thr Val Asn Ser Thr Asp Leu Asn Tyr Leu
1               5                   10                  15

Lys Lys Tyr Ile Leu Arg Val Ile
            20

<210> SEQ ID NO 75
<211> LENGTH: 24
<212> TYPE: PRT
<213> ORGANISM: Clostridium thermocellum

<400> SEQUENCE: 75

Asp Leu Asn Asn Asp Gly Asn Ile Asn Ser Thr Asp Tyr Met Ile Leu
1               5                   10                  15

Lys Lys Tyr Ile Leu Lys Val Leu
            20

<210> SEQ ID NO 76
<211> LENGTH: 24
<212> TYPE: PRT
<213> ORGANISM: Clostridium thermocellum

<400> SEQUENCE: 76

Asp Leu Asn Gly Asp Gly Ser Ile Asn Ser Thr Asp Leu Thr Ile Leu
1               5                   10                  15

Lys Arg Phe Ile Met Lys Ala Ile
            20

<210> SEQ ID NO 77
<211> LENGTH: 24
<212> TYPE: PRT
<213> ORGANISM: Clostridium thermocellum

<400> SEQUENCE: 77

Asp Leu Asn Gly Asp Gly Asn Ile Asn Ser Thr Asp Phe Thr Met Leu
1               5                   10                  15
```

Lys Arg Ala Ile Leu Gly Asn Pro
            20

<210> SEQ ID NO 78
<211> LENGTH: 24
<212> TYPE: PRT
<213> ORGANISM: Clostridium thermocellum

<400> SEQUENCE: 78

Asp Leu Asn Arg Asp Gly Asn Thr Asn Ser Thr Asp Leu Met Ile Leu
1               5                   10                  15

Arg Arg Tyr Leu Leu Lys Leu Ile
            20

<210> SEQ ID NO 79
<211> LENGTH: 24
<212> TYPE: PRT
<213> ORGANISM: Clostridium thermocellum

<400> SEQUENCE: 79

Asp Ile Asn Leu Asp Gly Lys Ile Asn Ser Thr Asp Leu Ser Ala Leu
1               5                   10                  15

Lys Arg His Ile Leu Arg Ile Thr
            20

<210> SEQ ID NO 80
<211> LENGTH: 24
<212> TYPE: PRT
<213> ORGANISM: Clostridium thermocellum

<400> SEQUENCE: 80

Asp Val Asn Asn Asp Gly Ser Val Asn Ser Thr Asp Ala Ser Ile Leu
1               5                   10                  15

Lys Lys Tyr Ile Ala Lys Ala Ile
            20

<210> SEQ ID NO 81
<211> LENGTH: 24
<212> TYPE: PRT
<213> ORGANISM: Clostridium thermocellum

<400> SEQUENCE: 81

Asp Phe Asn Ser Asp Ser Ser Val Asn Ser Thr Asp Leu Met Ile Leu
1               5                   10                  15

Asn Arg Ala Val Leu Gly Leu Gly
            20

<210> SEQ ID NO 82
<211> LENGTH: 24
<212> TYPE: PRT
<213> ORGANISM: Clostridium thermocellum

<400> SEQUENCE: 82

Glu Leu Asn Gly Asp Gly Lys Ile Asn Ser Ser Asp Leu Asn Met Met
1               5                   10                  15

Lys Arg Tyr Leu Leu Arg Leu Ile
            20

<210> SEQ ID NO 83
<211> LENGTH: 24
<212> TYPE: PRT
<213> ORGANISM: Clostridium thermocellum

```
<400> SEQUENCE: 83

Asp Leu Asn Gly Asp Gly Lys Ile Asn Ser Asp Tyr Ser Ile Leu
1               5                   10                  15

Lys Arg Tyr Leu Leu Arg Met Ile
            20

<210> SEQ ID NO 84
<211> LENGTH: 24
<212> TYPE: PRT
<213> ORGANISM: Clostridium thermocellum

<400> SEQUENCE: 84

Asp Leu Asn Gly Asp Ala Lys Ile Asn Ser Thr Asp Leu Asn Met Met
1               5                   10                  15

Lys Arg Tyr Leu Leu Gln Met Ile
            20

<210> SEQ ID NO 85
<211> LENGTH: 24
<212> TYPE: PRT
<213> ORGANISM: Clostridium thermocellum

<400> SEQUENCE: 85

Asp Leu Asn Gly Asp Gly Lys Ile Thr Ser Ser Asp Tyr Asn Leu Leu
1               5                   10                  15

Lys Arg Tyr Ile Leu His Leu Ile
            20

<210> SEQ ID NO 86
<211> LENGTH: 24
<212> TYPE: PRT
<213> ORGANISM: Clostridium thermocellum

<400> SEQUENCE: 86

Asp Val Asn Gly Asp Gly His Val Asn Ser Ser Asp Tyr Ser Leu Phe
1               5                   10                  15

Lys Arg Tyr Leu Leu Arg Val Ile
            20

<210> SEQ ID NO 87
<211> LENGTH: 24
<212> TYPE: PRT
<213> ORGANISM: Clostridium thermocellum

<400> SEQUENCE: 87

Asp Val Asn Arg Asp Gly Arg Ile Asp Ser Thr Asp Leu Thr Met Leu
1               5                   10                  15

Lys Arg Tyr Leu Ile Arg Ala Ile
            20

<210> SEQ ID NO 88
<211> LENGTH: 24
<212> TYPE: PRT
<213> ORGANISM: Clostridium thermocellum

<400> SEQUENCE: 88

Asp Tyr Asn Gly Asp Gly Ala Val Asn Ser Thr Asp Leu Leu Ala Cys
1               5                   10                  15

Lys Arg Tyr Leu Leu Tyr Ala Leu
            20
```

```
<210> SEQ ID NO 89
<211> LENGTH: 24
<212> TYPE: PRT
<213> ORGANISM: Clostridium thermocellum

<400> SEQUENCE: 89

Asp Leu Asp Gly Asn Gly Lys Ile Asn Ser Thr Asp Tyr Ala Tyr Leu
1               5                   10                  15

Lys Arg Tyr Leu Leu Lys Gln Ile
            20

<210> SEQ ID NO 90
<211> LENGTH: 24
<212> TYPE: PRT
<213> ORGANISM: Clostridium thermocellum

<400> SEQUENCE: 90

Asp Leu Asn Ala Asp Gly Lys Ile Asn Ser Thr Asp Tyr Asn Leu Gly
1               5                   10                  15

Lys Arg Leu Ile Leu Arg Thr Ile
            20

<210> SEQ ID NO 91
<211> LENGTH: 24
<212> TYPE: PRT
<213> ORGANISM: Clostridium thermocellum

<400> SEQUENCE: 91

Asp Leu Asn Gly Asp Ser Lys Val Asp Ser Thr Asp Leu Thr Ala Leu
1               5                   10                  15

Lys Arg Tyr Leu Leu Gly Val Ile
            20

<210> SEQ ID NO 92
<211> LENGTH: 24
<212> TYPE: PRT
<213> ORGANISM: Clostridium thermocellum

<400> SEQUENCE: 92

Asp Val Asn Gly Asp Ser Lys Ile Asn Ala Ile Asp Val Leu Leu Met
1               5                   10                  15

Lys Lys Tyr Ile Leu Lys Val Ile
            20

<210> SEQ ID NO 93
<211> LENGTH: 24
<212> TYPE: PRT
<213> ORGANISM: Clostridium thermocellum

<400> SEQUENCE: 93

Asp Val Asn Ala Asp Gly Gln Ile Asn Ser Ile Asp Phe Thr Trp Leu
1               5                   10                  15

Lys Lys Tyr Met Leu Lys Ala Val
            20

<210> SEQ ID NO 94
<211> LENGTH: 24
<212> TYPE: PRT
<213> ORGANISM: Clostridium thermocellum

<400> SEQUENCE: 94

Asp Val Asn Gly Asp Gly Asn Val Asn Ser Thr Asp Leu Thr Met Leu
```

```
1               5                   10                  15

Lys Arg Tyr Leu Leu Lys Ser Val
            20

<210> SEQ ID NO 95
<211> LENGTH: 24
<212> TYPE: PRT
<213> ORGANISM: Clostridium thermocellum

<400> SEQUENCE: 95

Asp Val Asn Arg Asp Gly Ala Ile Asn Ser Ser Asp Met Thr Ile Leu
1               5                   10                  15

Lys Arg Tyr Leu Ile Lys Ser Ile
            20

<210> SEQ ID NO 96
<211> LENGTH: 24
<212> TYPE: PRT
<213> ORGANISM: Clostridium thermocellum

<400> SEQUENCE: 96

Asp Leu Asn Gly Asp Gly Lys Val Asn Ser Ser Asp Leu Ala Ile Leu
1               5                   10                  15

Lys Arg Tyr Met Leu Arg Ala Ile
            20

<210> SEQ ID NO 97
<211> LENGTH: 24
<212> TYPE: PRT
<213> ORGANISM: Clostridium thermocellum

<400> SEQUENCE: 97

Asp Leu Asn Arg Asp Gly Asn Val Asn Ser Thr Asp Tyr Ser Ile Leu
1               5                   10                  15

Lys Arg Tyr Ile Leu Lys Ala Ile
            20

<210> SEQ ID NO 98
<211> LENGTH: 24
<212> TYPE: PRT
<213> ORGANISM: Clostridium thermocellum

<400> SEQUENCE: 98

Asp Leu Asn Val Asp Gly Ser Ile Asn Ser Val Asp Ile Thr Tyr Met
1               5                   10                  15

Lys Arg Tyr Leu Leu Arg Ser Ile
            20

<210> SEQ ID NO 99
<211> LENGTH: 24
<212> TYPE: PRT
<213> ORGANISM: Clostridium thermocellum

<400> SEQUENCE: 99

Asp Thr Asn Gly Asp Gly Ala Ile Asn Ser Ser Asp Met Val Leu Leu
1               5                   10                  15

Lys Arg Tyr Val Leu Arg Ser Ile
            20

<210> SEQ ID NO 100
<211> LENGTH: 24
<212> TYPE: PRT
```

<213> ORGANISM: Clostridium thermocellum

<400> SEQUENCE: 100

Asp Val Asn Gly Asp Gly Asn Val Asn Ser Thr Asp Val Val Trp Leu
1               5                   10                  15

Arg Arg Phe Leu Leu Lys Leu Val
            20

<210> SEQ ID NO 101
<211> LENGTH: 24
<212> TYPE: PRT
<213> ORGANISM: Clostridium thermocellum

<400> SEQUENCE: 101

Asp Met Asn Asp Asp Gly Asn Ile Asn Ser Thr Asp Met Ile Ala Leu
1               5                   10                  15

Lys Arg Lys Val Leu Lys Ile Pro
            20

<210> SEQ ID NO 102
<211> LENGTH: 24
<212> TYPE: PRT
<213> ORGANISM: Clostridium thermocellum

<400> SEQUENCE: 102

Asp Cys Asn Gly Asp Gly Lys Val Asn Ser Thr Asp Ala Val Ala Leu
1               5                   10                  15

Lys Arg Tyr Ile Leu Arg Ser Gly
            20

<210> SEQ ID NO 103
<211> LENGTH: 24
<212> TYPE: PRT
<213> ORGANISM: Clostridium thermocellum

<400> SEQUENCE: 103

Asp Val Asn Ala Asp Gly Arg Val Asn Ser Thr Asp Leu Ala Ile Leu
1               5                   10                  15

Lys Arg Tyr Ile Leu Lys Glu Ile
            20

<210> SEQ ID NO 104
<211> LENGTH: 24
<212> TYPE: PRT
<213> ORGANISM: Clostridium thermocellum

<400> SEQUENCE: 104

Asp Cys Asn Asp Asp Gly Lys Val Asn Ser Thr Asp Val Ala Val Met
1               5                   10                  15

Lys Arg Tyr Leu Lys Lys Glu Asn
            20

<210> SEQ ID NO 105
<211> LENGTH: 24
<212> TYPE: PRT
<213> ORGANISM: Clostridium thermocellum

<400> SEQUENCE: 105

Asp Val Asn Ala Asp Gly Lys Val Asn Ser Thr Asp Phe Ser Ile Leu
1               5                   10                  15

Lys Arg Tyr Val Met Lys Asn Ile
            20

```
<210> SEQ ID NO 106
<211> LENGTH: 24
<212> TYPE: PRT
<213> ORGANISM: Clostridium thermocellum

<400> SEQUENCE: 106

Asp Leu Asn Gly Asp Gly Arg Val Asn Ser Ser Asp Leu Ala Leu Met
1               5                   10                  15

Lys Arg Tyr Val Val Lys Gln Ile
            20

<210> SEQ ID NO 107
<211> LENGTH: 24
<212> TYPE: PRT
<213> ORGANISM: Clostridium thermocellum

<400> SEQUENCE: 107

Asp Leu Asn Gly Asp Asp Lys Val Asn Ser Thr Asp Tyr Ser Val Leu
1               5                   10                  15

Lys Arg Tyr Leu Leu Arg Ser Ile
            20

<210> SEQ ID NO 108
<211> LENGTH: 24
<212> TYPE: PRT
<213> ORGANISM: Clostridium thermocellum

<400> SEQUENCE: 108

Asp Val Asn Ala Asp Gly Val Val Asn Ile Ser Asp Tyr Val Leu Met
1               5                   10                  15

Lys Arg Tyr Ile Leu Arg Ile Ile
            20

<210> SEQ ID NO 109
<211> LENGTH: 24
<212> TYPE: PRT
<213> ORGANISM: Clostridium thermocellum

<400> SEQUENCE: 109

Asp Val Asn Gly Asp Asn Val Ile Asn Asp Ile Asp Cys Asn Tyr Leu
1               5                   10                  15

Lys Arg Tyr Leu Leu His Met Ile
            20

<210> SEQ ID NO 110
<211> LENGTH: 24
<212> TYPE: PRT
<213> ORGANISM: Clostridium thermocellum

<400> SEQUENCE: 110

Asp Leu Asn Gly Asp Asn Asn Ile Asn Ser Ser Asp Tyr Thr Leu Leu
1               5                   10                  15

Lys Arg Tyr Leu Leu His Thr Ile
            20

<210> SEQ ID NO 111
<211> LENGTH: 24
<212> TYPE: PRT
<213> ORGANISM: Clostridium thermocellum

<400> SEQUENCE: 111
```

```
Asp Val Asn Gly Asp Gly Arg Val Asn Ser Ser Asp Val Ala Leu Leu
1               5                   10                  15

Lys Arg Tyr Leu Leu Gly Leu Val
            20

<210> SEQ ID NO 112
<211> LENGTH: 24
<212> TYPE: PRT
<213> ORGANISM: Clostridium thermocellum

<400> SEQUENCE: 112

Asp Val Asn Val Ser Gly Thr Val Asn Ser Thr Asp Leu Ala Ile Met
1               5                   10                  15

Lys Arg Tyr Val Leu Arg Ser Ile
            20

<210> SEQ ID NO 113
<211> LENGTH: 24
<212> TYPE: PRT
<213> ORGANISM: Clostridium thermocellum

<400> SEQUENCE: 113

Asp Val Asn Phe Asp Gly Arg Ile Asn Ser Thr Asp Tyr Ser Arg Leu
1               5                   10                  15

Lys Arg Tyr Val Ile Lys Ser Leu
            20

<210> SEQ ID NO 114
<211> LENGTH: 24
<212> TYPE: PRT
<213> ORGANISM: Clostridium thermocellum

<400> SEQUENCE: 114

Asp Val Asp Gly Asn Gly Arg Ile Asn Ser Thr Asp Leu Tyr Val Leu
1               5                   10                  15

Asn Arg Tyr Ile Leu Lys Leu Ile
            20

<210> SEQ ID NO 115
<211> LENGTH: 24
<212> TYPE: PRT
<213> ORGANISM: Clostridium thermocellum

<400> SEQUENCE: 115

Asp Ile Asn Leu Asp Gly Lys Ile Asn Ser Ser Asp Val Thr Leu Leu
1               5                   10                  15

Lys Arg Tyr Ile Val Lys Ser Ile
            20

<210> SEQ ID NO 116
<211> LENGTH: 24
<212> TYPE: PRT
<213> ORGANISM: Clostridium thermocellum

<400> SEQUENCE: 116

Asp Val Asn Gly Asp Gly Arg Val Asn Ser Thr Asp Tyr Ser Tyr Leu
1               5                   10                  15

Lys Arg Tyr Val Leu Lys Ile Ile
            20

<210> SEQ ID NO 117
<211> LENGTH: 24
```

```
<212> TYPE: PRT
<213> ORGANISM: Clostridium thermocellum

<400> SEQUENCE: 117

Asp Leu Asn Gly Asp Asn Val Asn Ser Thr Asp Leu Thr Leu Leu
1               5                   10                  15

Lys Arg Tyr Leu Thr Arg Val Ile
            20

<210> SEQ ID NO 118
<211> LENGTH: 24
<212> TYPE: PRT
<213> ORGANISM: Clostridium thermocellum

<400> SEQUENCE: 118

Asp Val Asn Gly Asp Gly Lys Ile Asn Ser Thr Asp Tyr Ser Ala Met
1               5                   10                  15

Ile Arg Tyr Ile Leu Arg Ile Ile
            20

<210> SEQ ID NO 119
<211> LENGTH: 24
<212> TYPE: PRT
<213> ORGANISM: Clostridium thermocellum

<400> SEQUENCE: 119

Asp Val Asn Gly Asp Leu Lys Val Asn Ser Thr Asp Phe Ser Met Leu
1               5                   10                  15

Arg Arg Tyr Leu Leu Lys Thr Ile
            20

<210> SEQ ID NO 120
<211> LENGTH: 24
<212> TYPE: PRT
<213> ORGANISM: Clostridium thermocellum

<400> SEQUENCE: 120

Asp Leu Asn Gly Asp Gly Arg Ile Asn Ser Ser Asp Leu Thr Met Leu
1               5                   10                  15

Lys Arg Tyr Leu Leu Met Glu Val
            20

<210> SEQ ID NO 121
<211> LENGTH: 24
<212> TYPE: PRT
<213> ORGANISM: Clostridium thermocellum

<400> SEQUENCE: 121

Asp Leu Asn Asn Asp Ser Lys Val Asn Ala Val Asp Ile Met Met Leu
1               5                   10                  15

Lys Arg Tyr Ile Leu Gly Ile Ile
            20

<210> SEQ ID NO 122
<211> LENGTH: 24
<212> TYPE: PRT
<213> ORGANISM: Clostridium thermocellum

<400> SEQUENCE: 122

Asp Ile Tyr Phe Asp Gly Val Val Asn Ser Ser Asp Tyr Asn Ile Met
1               5                   10                  15

Lys Arg Tyr Leu Leu Lys Ala Ile
```

<210> SEQ ID NO 123
<211> LENGTH: 24
<212> TYPE: PRT
<213> ORGANISM: Clostridium thermocellum

<400> SEQUENCE: 123

Asp Leu Asn Gly Asp Gly Val Val Asn Ser Thr Asp Ser Val Ile Leu
1               5                   10                  15

Lys Arg His Ile Ile Lys Phe Ser
            20

<210> SEQ ID NO 124
<211> LENGTH: 24
<212> TYPE: PRT
<213> ORGANISM: Clostridium thermocellum

<400> SEQUENCE: 124

Asp Leu Asn Gly Asp Gly Asn Ile Asn Ser Ser Asp Val Ser Leu Met
1               5                   10                  15

Lys Arg Tyr Leu Leu Arg Ile Ile
            20

<210> SEQ ID NO 125
<211> LENGTH: 24
<212> TYPE: PRT
<213> ORGANISM: Clostridium thermocellum

<400> SEQUENCE: 125

Asp Leu Asn Gly Asp Gly Lys Ile Asn Ser Thr Asp Ile Ser Leu Met
1               5                   10                  15

Lys Arg Tyr Leu Leu Lys Gln Ile
            20

<210> SEQ ID NO 126
<211> LENGTH: 24
<212> TYPE: PRT
<213> ORGANISM: Clostridium thermocellum

<400> SEQUENCE: 126

Asp Ile Asn Lys Asp Gly Lys Val Asn Ser Thr Asp Met Ser Ile Leu
1               5                   10                  15

Lys Arg Val Ile Leu Arg Asn Tyr
            20

<210> SEQ ID NO 127
<211> LENGTH: 24
<212> TYPE: PRT
<213> ORGANISM: Clostridium thermocellum

<400> SEQUENCE: 127

Asp Ser Asn Ser Asp Cys Lys Val Asn Ser Thr Asp Leu Thr Leu Met
1               5                   10                  15

Lys Arg Tyr Leu Leu Gln Gln Ser
            20

<210> SEQ ID NO 128
<211> LENGTH: 24
<212> TYPE: PRT
<213> ORGANISM: Clostridium thermocellum

<400> SEQUENCE: 128

```
Asp Leu Asn Gly Asp Gly Lys Ile Asn Ser Ser Asp Tyr Thr Leu Leu
1               5                   10                  15

Lys Arg Tyr Leu Leu Gly Tyr Ile
            20
```

<210> SEQ ID NO 129
<211> LENGTH: 24
<212> TYPE: PRT
<213> ORGANISM: Clostridium thermocellum

<400> SEQUENCE: 129

```
Asp Ile Asn Asn Asp Lys Thr Val Asn Ser Thr Asp Val Thr Tyr Leu
1               5                   10                  15

Lys Arg Phe Leu Leu Lys Gln Ile
            20
```

<210> SEQ ID NO 130
<211> LENGTH: 24
<212> TYPE: PRT
<213> ORGANISM: Clostridium thermocellum

<400> SEQUENCE: 130

```
Asp Val Asn Leu Asp Gly Asn Ile Asn Ser Thr Asp Leu Val Ile Leu
1               5                   10                  15

Lys Arg Tyr Val Leu Arg Gly Ile
            20
```

<210> SEQ ID NO 131
<211> LENGTH: 24
<212> TYPE: PRT
<213> ORGANISM: Clostridium thermocellum

<400> SEQUENCE: 131

```
Asp Val Asn Gly Asp Gly Lys Ile Asn Ser Thr Asp Cys Thr Met Leu
1               5                   10                  15

Lys Arg Tyr Ile Leu Arg Gly Ile
            20
```

<210> SEQ ID NO 132
<211> LENGTH: 24
<212> TYPE: PRT
<213> ORGANISM: Clostridium thermocellum

<400> SEQUENCE: 132

```
Asp Val Asn Ala Asp Leu Lys Ile Asn Ser Thr Asp Leu Val Leu Met
1               5                   10                  15

Lys Lys Tyr Leu Leu Arg Ser Ile
            20
```

<210> SEQ ID NO 133
<211> LENGTH: 24
<212> TYPE: PRT
<213> ORGANISM: Clostridium thermocellum

<400> SEQUENCE: 133

```
Asp Val Asn Leu Asp Gly Gln Val Asn Ser Thr Asp Phe Ser Leu Leu
1               5                   10                  15

Lys Arg Tyr Ile Leu Lys Val Val
            20
```

<210> SEQ ID NO 134

```
<211> LENGTH: 23
<212> TYPE: PRT
<213> ORGANISM: Clostridium thermocellum

<400> SEQUENCE: 134

Asp Met Asn Asn Asp Gly Asn Ile Asn Ser Thr Asp Ile Ser Ile Leu
1               5                   10                  15

Lys Arg Ile Leu Leu Arg Asn
            20

<210> SEQ ID NO 135
<211> LENGTH: 24
<212> TYPE: PRT
<213> ORGANISM: Clostridium thermocellum

<400> SEQUENCE: 135

Asp Ile Asn Arg Asp Gly Lys Ile Asn Ser Thr Asp Leu Gly Met Leu
1               5                   10                  15

Asn Arg His Ile Leu Lys Leu Val
            20

<210> SEQ ID NO 136
<211> LENGTH: 24
<212> TYPE: PRT
<213> ORGANISM: Clostridium thermocellum

<400> SEQUENCE: 136

Asp Ile Asp Gly Asn Gly Asn Ile Asn Ser Thr Asp Tyr Ser Trp Leu
1               5                   10                  15

Lys Lys Tyr Ile Leu Lys Val Ile
            20

<210> SEQ ID NO 137
<211> LENGTH: 24
<212> TYPE: PRT
<213> ORGANISM: Clostridium thermocellum

<400> SEQUENCE: 137

Asp Val Asn Asp Asp Gly Lys Val Asn Ser Thr Asp Leu Thr Leu Leu
1               5                   10                  15

Lys Arg Tyr Val Leu Lys Ala Val
            20

<210> SEQ ID NO 138
<211> LENGTH: 24
<212> TYPE: PRT
<213> ORGANISM: Clostridium thermocellum

<400> SEQUENCE: 138

Asp Val Asn Arg Asp Gly Arg Val Asn Ser Ser Asp Val Thr Ile Leu
1               5                   10                  15

Ser Arg Tyr Leu Ile Arg Val Ile
            20

<210> SEQ ID NO 139
<211> LENGTH: 24
<212> TYPE: PRT
<213> ORGANISM: Clostridium thermocellum

<400> SEQUENCE: 139

Asp Val Asn Gly Asp Gly Thr Ile Asn Ser Thr Asp Leu Thr Met Leu
1               5                   10                  15
```

Lys Arg Ser Val Leu Arg Ala Ile
            20

<210> SEQ ID NO 140
<211> LENGTH: 24
<212> TYPE: PRT
<213> ORGANISM: Clostridium thermocellum

<400> SEQUENCE: 140

Asp Val Asp Lys Asn Gly Ser Ile Asn Ser Thr Asp Val Leu Leu Leu
1               5                   10                  15

Ser Arg Tyr Leu Leu Arg Val Ile
            20

<210> SEQ ID NO 141
<211> LENGTH: 24
<212> TYPE: PRT
<213> ORGANISM: Clostridium thermocellum

<400> SEQUENCE: 141

Asp Leu Asn Arg Asn Gly Ile Val Asn Asp Glu Asp Tyr Ile Leu Leu
1               5                   10                  15

Lys Asn Tyr Leu Leu Arg Gly Asn
            20

<210> SEQ ID NO 142
<211> LENGTH: 24
<212> TYPE: PRT
<213> ORGANISM: Clostridium thermocellum

<400> SEQUENCE: 142

Asp Val Asn Lys Asp Gly Lys Val Asn Ser Thr Asp Cys Leu Phe Leu
1               5                   10                  15

Lys Lys Tyr Ile Leu Gly Leu Ile
            20

<210> SEQ ID NO 143
<211> LENGTH: 24
<212> TYPE: PRT
<213> ORGANISM: Clostridium thermocellum

<400> SEQUENCE: 143

Asp Thr Asn Ser Asp Gly Lys Ile Asn Ser Thr Asp Val Thr Ala Leu
1               5                   10                  15

Lys Arg His Leu Leu Arg Val Thr
            20

<210> SEQ ID NO 144
<211> LENGTH: 24
<212> TYPE: PRT
<213> ORGANISM: Clostridium thermocellum

<400> SEQUENCE: 144

Asp Val Asn Gly Asp Gly Asn Val Asn Ser Thr Asp Leu Leu Leu Leu
1               5                   10                  15

Lys Arg Tyr Ile Leu Gly Glu Ile
            20

<210> SEQ ID NO 145
<211> LENGTH: 24
<212> TYPE: PRT
<213> ORGANISM: Clostridium thermocellum -continued

```
<400> SEQUENCE: 145

Asp Leu Asn Gly Asp Asn Arg Ile Asn Ser Thr Asp Leu Thr Leu Met
1               5                   10                  15

Lys Arg Tyr Ile Leu Lys Ser Ile
            20

<210> SEQ ID NO 146
<211> LENGTH: 24
<212> TYPE: PRT
<213> ORGANISM: Clostridium thermocellum

<400> SEQUENCE: 146

Asp Ile Asn Gly Asp Gly Lys Ile Asn Ser Thr Asp Tyr Thr Tyr Leu
1               5                   10                  15

Lys Lys Tyr Leu Leu Gln Ala Ile
            20

<210> SEQ ID NO 147
<211> LENGTH: 24
<212> TYPE: PRT
<213> ORGANISM: Clostridium thermocellum

<400> SEQUENCE: 147

Asp Leu Asn Gly Asp Gly Arg Val Asn Ser Thr Asp Tyr Thr Leu Leu
1               5                   10                  15

Lys Arg Tyr Leu Leu Gly Ala Ile
            20

<210> SEQ ID NO 148
<211> LENGTH: 24
<212> TYPE: PRT
<213> ORGANISM: Clostridium thermocellum

<400> SEQUENCE: 148

Asp Leu Asn Leu Asp Gly Arg Ile Asn Ser Thr Asp Tyr Thr Val Leu
1               5                   10                  15

Lys Arg Tyr Leu Leu Asn Ala Ile
            20

<210> SEQ ID NO 149
<211> LENGTH: 24
<212> TYPE: PRT
<213> ORGANISM: Clostridium thermocellum

<400> SEQUENCE: 149

Asp Leu Asn Phe Asp Asn Ala Val Asn Ser Thr Asp Leu Leu Met Leu
1               5                   10                  15

Lys Arg Tyr Ile Leu Lys Ser Leu
            20

<210> SEQ ID NO 150
<211> LENGTH: 24
<212> TYPE: PRT
<213> ORGANISM: Clostridium thermocellum

<400> SEQUENCE: 150

Asp Leu Asn Arg Asp Asn Lys Val Asp Ser Thr Asp Leu Thr Ile Leu
1               5                   10                  15

Lys Arg Tyr Leu Leu Lys Ala Ile
            20
```

```
<210> SEQ ID NO 151
<211> LENGTH: 24
<212> TYPE: PRT
<213> ORGANISM: Clostridium thermocellum

<400> SEQUENCE: 151

Glu Val Ile Asp Thr Lys Val Ile Asp Ser Thr Asp Ile Val Lys
1               5                   10                  15

Tyr Glu Tyr Gln Phe Asp Lys Lys
            20

<210> SEQ ID NO 152
<211> LENGTH: 24
<212> TYPE: PRT
<213> ORGANISM: Clostridium thermocellum

<400> SEQUENCE: 152

Thr Leu Val Leu Ser Val Asn Asn Asp Ser Thr Asp Lys Thr Thr Val
1               5                   10                  15

Ser Gly Tyr Ile Ser Val Asp Phe
            20

<210> SEQ ID NO 153
<211> LENGTH: 24
<212> TYPE: PRT
<213> ORGANISM: Clostridium thermocellum

<400> SEQUENCE: 153

Asp Val Asn Gly Asp Gly Arg Val Asn Ser Ser Asp Leu Thr Leu Met
1               5                   10                  15

Lys Arg Tyr Leu Leu Lys Ser Ile
            20

<210> SEQ ID NO 154
<211> LENGTH: 24
<212> TYPE: PRT
<213> ORGANISM: Clostridium thermocellum

<400> SEQUENCE: 154

Asp Leu Asn Glu Asp Gly Lys Val Asn Ser Thr Asp Leu Leu Ala Leu
1               5                   10                  15

Lys Lys Leu Val Leu Arg Glu Leu
            20

<210> SEQ ID NO 155
<211> LENGTH: 24
<212> TYPE: PRT
<213> ORGANISM: Clostridium thermocellum

<400> SEQUENCE: 155

Asp Leu Asn Ala Asp Gly Ser Ile Asn Ser Thr Asp Leu Met Ile Met
1               5                   10                  15

Lys Arg Val Leu Leu Lys Gln Arg
            20

<210> SEQ ID NO 156
<211> LENGTH: 24
<212> TYPE: PRT
<213> ORGANISM: Clostridium thermocellum

<400> SEQUENCE: 156

Asp Leu Asn Gly Asp Gly Lys Val Thr Ser Thr Asp Tyr Ser Leu Met
1               5                   10                  15
```

-continued

```
Lys Arg Tyr Leu Leu Lys Glu Ile
            20

<210> SEQ ID NO 157
<211> LENGTH: 24
<212> TYPE: PRT
<213> ORGANISM: Clostridium thermocellum

<400> SEQUENCE: 157

Asp Leu Asn Gly Asp Gly Asn Ile Asn Ser Ser Asp Leu Gln Ala Leu
1               5                   10                  15

Lys Arg His Leu Leu Gly Ile Ser
            20

<210> SEQ ID NO 158
<211> LENGTH: 24
<212> TYPE: PRT
<213> ORGANISM: Clostridium thermocellum

<400> SEQUENCE: 158

Asp Val Asn Arg Ser Gly Lys Val Asp Ser Thr Asp Tyr Ser Val Leu
1               5                   10                  15

Lys Arg Tyr Ile Leu Arg Ile Ile
            20

<210> SEQ ID NO 159
<211> LENGTH: 24
<212> TYPE: PRT
<213> ORGANISM: Clostridium thermocellum

<400> SEQUENCE: 159

Asp Ile Val Leu Asp Gly Asn Ile Asn Ser Leu Asp Met Met Lys Leu
1               5                   10                  15

Lys Lys Tyr Leu Ile Arg Glu Thr
            20

<210> SEQ ID NO 160
<211> LENGTH: 24
<212> TYPE: PRT
<213> ORGANISM: Clostridium thermocellum

<400> SEQUENCE: 160

Asp Val Asn Ser Asp Gly Glu Val Asn Ser Thr Asp Tyr Ala Tyr Leu
1               5                   10                  15

Lys Arg Tyr Ile Leu Arg Ile Ile
            20

<210> SEQ ID NO 161
<211> LENGTH: 24
<212> TYPE: PRT
<213> ORGANISM: Clostridium thermocellum

<400> SEQUENCE: 161

Asp Val Asn Asp Asp Gly Lys Val Asn Ser Thr Asp Ala Val Ala Leu
1               5                   10                  15

Lys Arg Tyr Val Leu Arg Ser Gly
            20

<210> SEQ ID NO 162
<211> LENGTH: 24
<212> TYPE: PRT
<213> ORGANISM: Clostridium thermocellum
```

<400> SEQUENCE: 162

Asp Leu Asn Glu Asp Gly Arg Val Asn Ser Thr Asp Leu Gly Ile Leu
1               5                   10                  15

Lys Arg Tyr Ile Leu Lys Glu Ile
            20

<210> SEQ ID NO 163
<211> LENGTH: 24
<212> TYPE: PRT
<213> ORGANISM: Clostridium thermocellum

<400> SEQUENCE: 163

Asp Val Asp Gly Asn Gly Thr Val Asn Ser Thr Asp Val Asn Tyr Met
1               5                   10                  15

Lys Arg Tyr Leu Leu Arg Gln Ile
            20

<210> SEQ ID NO 164
<211> LENGTH: 24
<212> TYPE: PRT
<213> ORGANISM: Clostridium thermocellum

<400> SEQUENCE: 164

Asp Val Asp Gly Asn Gly Asn Ile Asn Ser Thr Asp Leu Ser Tyr Leu
1               5                   10                  15

Lys Lys Tyr Ile Leu Lys Leu Ile
            20

<210> SEQ ID NO 165
<211> LENGTH: 24
<212> TYPE: PRT
<213> ORGANISM: Clostridium thermocellum

<400> SEQUENCE: 165

Asp Val Asn Ala Asp Gly Val Ile Asn Ser Ser Asp Ile Met Val Leu
1               5                   10                  15

Lys Arg Phe Leu Leu Arg Thr Ile
            20

<210> SEQ ID NO 166
<211> LENGTH: 24
<212> TYPE: PRT
<213> ORGANISM: Clostridium thermocellum

<400> SEQUENCE: 166

Asp Thr Asn Gly Asp Gly Ala Val Asn Ser Asp Phe Thr Leu Leu
1               5                   10                  15

Lys Arg Tyr Ile Leu Arg Ser Ile
            20

<210> SEQ ID NO 167
<211> LENGTH: 24
<212> TYPE: PRT
<213> ORGANISM: Clostridium thermocellum

<400> SEQUENCE: 167

Asp Val Asn Gly Asp Phe Ala Val Asn Ser Asn Asp Leu Thr Leu Ile
1               5                   10                  15

Lys Arg Tyr Val Leu Lys Asn Ile
            20

<210> SEQ ID NO 168
<211> LENGTH: 24
<212> TYPE: PRT
<213> ORGANISM: Clostridium thermocellum

<400> SEQUENCE: 168

Asp Val Asp Gly Asp Glu Lys Ile Thr Ser Ser Asp Ala Ala Leu Val
1               5                   10                  15

Lys Arg Tyr Val Leu Arg Ala Ile
            20

<210> SEQ ID NO 169
<211> LENGTH: 24
<212> TYPE: PRT
<213> ORGANISM: Clostridium thermocellum

<400> SEQUENCE: 169

Asp Leu Asn Gly Asp Gly Asn Val Asn Ser Thr Asp Ser Ile Leu Met
1               5                   10                  15

Lys Arg Tyr Leu Met Lys Ser Val
            20

<210> SEQ ID NO 170
<211> LENGTH: 24
<212> TYPE: PRT
<213> ORGANISM: Clostridium thermocellum

<400> SEQUENCE: 170

Asp Val Asn Leu Asp Gly Arg Val Asn Ser Thr Asp Arg Ser Ile Leu
1               5                   10                  15

Asn Arg Tyr Leu Leu Lys Ile Ile
            20

<210> SEQ ID NO 171
<211> LENGTH: 24
<212> TYPE: PRT
<213> ORGANISM: Clostridium thermocellum

<400> SEQUENCE: 171

Asp Ile Asn Asp Asp Gly Asn Ile Asn Ser Thr Asp Leu Gln Met Leu
1               5                   10                  15

Lys Arg His Leu Leu Arg Ser Ile
            20

<210> SEQ ID NO 172
<211> LENGTH: 24
<212> TYPE: PRT
<213> ORGANISM: Clostridium thermocellum

<400> SEQUENCE: 172

Asp Thr Asn Arg Asp Gly Arg Val Asp Ser Thr Asp Leu Ala Leu Leu
1               5                   10                  15

Lys Arg Tyr Ile Leu Arg Val Ile
            20

<210> SEQ ID NO 173
<211> LENGTH: 24
<212> TYPE: PRT
<213> ORGANISM: Clostridium thermocellum

<400> SEQUENCE: 173

Asp Leu Asn Gly Asp Gly Asn Ile Asn Ser Thr Asp Leu Gln Ile Leu

```
1               5                   10                  15

Lys Lys His Leu Leu Arg Ile Thr
            20

<210> SEQ ID NO 174
<211> LENGTH: 24
<212> TYPE: PRT
<213> ORGANISM: Clostridium thermocellum

<400> SEQUENCE: 174

Asp Val Thr Lys Asp Gly Lys Val Asp Ser Thr Asp Leu Thr Leu Leu
1               5                   10                  15

Lys Arg Tyr Ile Leu Arg Phe Val
            20

<210> SEQ ID NO 175
<211> LENGTH: 24
<212> TYPE: PRT
<213> ORGANISM: Clostridium thermocellum

<400> SEQUENCE: 175

Asp Leu Asn Asp Asp Gly Lys Val Asn Ser Thr Asp Phe Gln Ile Leu
1               5                   10                  15

Lys Lys His Leu Leu Arg Ile Thr
            20

<210> SEQ ID NO 176
<211> LENGTH: 24
<212> TYPE: PRT
<213> ORGANISM: Clostridium thermocellum

<400> SEQUENCE: 176

Asp Leu Asn Lys Asp Gly Lys Val Asp Ser Ser Asp Leu Ser Leu Met
1               5                   10                  15

Lys Arg Tyr Leu Leu Gln Ile Ile
            20

<210> SEQ ID NO 177
<211> LENGTH: 24
<212> TYPE: PRT
<213> ORGANISM: Clostridium thermocellum

<400> SEQUENCE: 177

Asp Leu Asn Asn Asp Gly Lys Val Asn Ser Thr Asp Phe Gln Leu Leu
1               5                   10                  15

Lys Met His Val Leu Arg Gln Glu
            20

<210> SEQ ID NO 178
<211> LENGTH: 24
<212> TYPE: PRT
<213> ORGANISM: Clostridium thermocellum

<400> SEQUENCE: 178

Asp Val Asn Arg Asp Gly Lys Val Asp Ser Ser Asp Cys Thr Leu Leu
1               5                   10                  15

Lys Arg Tyr Ile Leu Arg Val Ile
            20

<210> SEQ ID NO 179
<211> LENGTH: 24
<212> TYPE: PRT
```

<213> ORGANISM: Clostridium thermocellum

<400> SEQUENCE: 179

Asp Leu Asn Gly Asp Gly Lys Val Asn Ser Thr Asp Leu Gln Leu Met
1               5                   10                  15
Lys Met His Val Leu Arg Gln Arg
            20

<210> SEQ ID NO 180
<211> LENGTH: 24
<212> TYPE: PRT
<213> ORGANISM: Clostridium thermocellum

<400> SEQUENCE: 180

Asp Val Asn Arg Asp Gly Lys Val Asp Ser Thr Asp Val Ala Leu Leu
1               5                   10                  15
Lys Arg Tyr Ile Leu Arg Gln Ile
            20

<210> SEQ ID NO 181
<211> LENGTH: 24
<212> TYPE: PRT
<213> ORGANISM: Clostridium thermocellum

<400> SEQUENCE: 181

Asp Val Asn Leu Asp Gly Ser Val Asp Ser Ile Asp Leu Ala Leu Leu
1               5                   10                  15
Tyr Asn Thr Thr Tyr Tyr Ala Val
            20

<210> SEQ ID NO 182
<211> LENGTH: 24
<212> TYPE: PRT
<213> ORGANISM: Clostridium thermocellum

<400> SEQUENCE: 182

Asp Val Asn Gly Asp Gly Thr Val Asp Gly Ile Asp Leu Ala Ile Ile
1               5                   10                  15
Thr Ala Tyr Ile Asn Gly Gln Ile
            20

<210> SEQ ID NO 183
<211> LENGTH: 24
<212> TYPE: PRT
<213> ORGANISM: Clostridium thermocellum

<400> SEQUENCE: 183

Asp Leu Asn Gly Asp Gly Arg Val Asn Ser Thr Asp Leu Leu Leu Met
1               5                   10                  15
Lys Lys Arg Ile Ile Arg Glu Ile
            20

<210> SEQ ID NO 184
<211> LENGTH: 24
<212> TYPE: PRT
<213> ORGANISM: Clostridium thermocellum

<400> SEQUENCE: 184

Asp Leu Asn Leu Asp Gly Lys Ile Asn Ser Ser Asp Tyr Thr Ile Leu
1               5                   10                  15
Lys Arg Tyr Val Leu Lys Ser Ile
            20

<210> SEQ ID NO 185
<211> LENGTH: 24
<212> TYPE: PRT
<213> ORGANISM: Clostridium thermocellum

<400> SEQUENCE: 185

Asp Val Asn Lys Asp Gly Arg Ile Asn Ser Thr Asp Ile Met Tyr Leu
1               5                   10                  15

Lys Gly Tyr Leu Leu Arg Asn Ser
            20

<210> SEQ ID NO 186
<211> LENGTH: 24
<212> TYPE: PRT
<213> ORGANISM: Clostridium thermocellum

<400> SEQUENCE: 186

Asp Val Asp Gly Asn Gly Ser Val Ser Ser Leu Asp Leu Thr Tyr Leu
1               5                   10                  15

Lys Arg Tyr Ile Leu Arg Arg Ile
            20

<210> SEQ ID NO 187
<211> LENGTH: 24
<212> TYPE: PRT
<213> ORGANISM: Clostridium thermocellum

<400> SEQUENCE: 187

Asp Leu Asn Gln Asp Gly Gln Val Ser Ser Thr Asp Leu Val Ala Met
1               5                   10                  15

Lys Arg Tyr Leu Leu Lys Asn Phe
            20

<210> SEQ ID NO 188
<211> LENGTH: 24
<212> TYPE: PRT
<213> ORGANISM: Clostridium thermocellum

<400> SEQUENCE: 188

Asp Leu Asn Ser Asp Gly Lys Val Asn Ser Thr Asp Leu Val Ala Leu
1               5                   10                  15

Lys Arg Phe Leu Leu Lys Glu Ile
            20

<210> SEQ ID NO 189
<211> LENGTH: 24
<212> TYPE: PRT
<213> ORGANISM: Clostridium thermocellum

<400> SEQUENCE: 189

Asp Leu Asn Tyr Asp Gly Lys Val Asn Ser Thr Asp Tyr Leu Val Leu
1               5                   10                  15

Lys Arg Tyr Leu Leu Gly Thr Ile
            20

<210> SEQ ID NO 190
<211> LENGTH: 24
<212> TYPE: PRT
<213> ORGANISM: Clostridium thermocellum

<400> SEQUENCE: 190

Asp Leu Asn Arg Asp Gly Arg Val Asn Ser Thr Asp Met Ser Leu Met
1               5                   10                  15

Lys Arg Tyr Leu Leu Gly Ile Ile
            20

<210> SEQ ID NO 191
<211> LENGTH: 24
<212> TYPE: PRT
<213> ORGANISM: Clostridium thermocellum

<400> SEQUENCE: 191

Asp Val Asn Gly Asp Gly Lys Val Asn Ser Thr Asp Cys Ser Ile Val
1               5                   10                  15

Lys Arg Tyr Leu Leu Lys Asn Ile
            20

<210> SEQ ID NO 192
<211> LENGTH: 24
<212> TYPE: PRT
<213> ORGANISM: Clostridium thermocellum

<400> SEQUENCE: 192

Asp Val Asn Gly Asp Gly Lys Val Asn Ser Thr Asp Tyr Ser Leu Leu
1               5                   10                  15

Lys Arg Phe Val Leu Arg Asn Ile
            20

<210> SEQ ID NO 193
<211> LENGTH: 24
<212> TYPE: PRT
<213> ORGANISM: Clostridium thermocellum

<400> SEQUENCE: 193

Asp Leu Asn Gly Asp Gly Lys Val Asn Ser Thr Asp Leu Thr Ile Met
1               5                   10                  15

Lys Arg Tyr Ile Leu Lys Asn Phe
            20

<210> SEQ ID NO 194
<211> LENGTH: 24
<212> TYPE: PRT
<213> ORGANISM: Clostridium thermocellum

<400> SEQUENCE: 194

Asp Leu Asn Gly Asp Gly Arg Ile Asn Ser Thr Asp Leu Ser Ile Leu
1               5                   10                  15

His Arg Tyr Leu Leu Arg Ile Ile
            20

<210> SEQ ID NO 195
<211> LENGTH: 24
<212> TYPE: PRT
<213> ORGANISM: Clostridium thermocellum

<400> SEQUENCE: 195

Asp Leu Asn Gly Asp Gln Lys Val Thr Ser Thr Asp Tyr Thr Met Leu
1               5                   10                  15

Lys Arg Tyr Leu Met Lys Ser Ile
            20

<210> SEQ ID NO 196
<211> LENGTH: 24

<212> TYPE: PRT
<213> ORGANISM: Clostridium thermocellum

<400> SEQUENCE: 196

Asp Leu Asn Arg Asp Gly Lys Ile Asn Ser Thr Asp Leu Thr Ile Leu
1               5                   10                  15

Lys Arg Tyr Leu Leu Tyr Ser Ile
            20

<210> SEQ ID NO 197
<211> LENGTH: 24
<212> TYPE: PRT
<213> ORGANISM: Clostridium thermocellum

<400> SEQUENCE: 197

Asp Ile Asn Ser Asp Gly Asn Val Asn Ser Thr Asp Leu Gly Ile Leu
1               5                   10                  15

Lys Arg Ile Ile Val Lys Asn Pro
            20

<210> SEQ ID NO 198
<211> LENGTH: 24
<212> TYPE: PRT
<213> ORGANISM: Clostridium thermocellum

<400> SEQUENCE: 198

Asp Val Asn Ala Asp Gly Lys Val Asn Ser Thr Asp Tyr Thr Val Leu
1               5                   10                  15

Lys Arg Tyr Leu Leu Arg Ser Ile
            20

<210> SEQ ID NO 199
<211> LENGTH: 24
<212> TYPE: PRT
<213> ORGANISM: Clostridium thermocellum

<400> SEQUENCE: 199

Asp Ile Asn Ser Asp Gly Ser Ile Asn Ser Thr Asp Val Thr Leu Leu
1               5                   10                  15

Lys Arg His Leu Leu Arg Glu Asn
            20

<210> SEQ ID NO 200
<211> LENGTH: 24
<212> TYPE: PRT
<213> ORGANISM: Clostridium thermocellum

<400> SEQUENCE: 200

Asp Thr Asp Gly Asp Gly Lys Ile Thr Ser Ile Asp Leu Ser Tyr Leu
1               5                   10                  15

Lys Arg Tyr Val Leu Arg Leu Ile
            20

<210> SEQ ID NO 201
<211> LENGTH: 24
<212> TYPE: PRT
<213> ORGANISM: Clostridium thermocellum

<400> SEQUENCE: 201

Asp Leu Asn Gly Asp Gly Leu Val Asn Ser Ser Asp Tyr Ser Leu Leu
1               5                   10                  15

Lys Arg Tyr Ile Leu Lys Gln Ile

<210> SEQ ID NO 202
<211> LENGTH: 24
<212> TYPE: PRT
<213> ORGANISM: Clostridium thermocellum

<400> SEQUENCE: 202

Asp Leu Asn Arg Asn Gly Ser Val Asp Ser Val Asp Tyr Ser Ile Leu
1               5                   10                  15

Lys Arg Phe Leu Leu Lys Thr Ile
            20

<210> SEQ ID NO 203
<211> LENGTH: 24
<212> TYPE: PRT
<213> ORGANISM: Clostridium thermocellum

<400> SEQUENCE: 203

Asp Leu Asn Asn Asp Gly Arg Thr Asn Ser Thr Asp Tyr Ser Leu Met
1               5                   10                  15

Lys Arg Tyr Leu Leu Gly Ser Ile
            20

<210> SEQ ID NO 204
<211> LENGTH: 24
<212> TYPE: PRT
<213> ORGANISM: Clostridium thermocellum

<400> SEQUENCE: 204

Asp Val Asn Leu Asp Gly Lys Val Asn Ser Ser Asp Tyr Thr Val Leu
1               5                   10                  15

Arg Arg Phe Leu Leu Gly Ser Ile
            20

<210> SEQ ID NO 205
<211> LENGTH: 24
<212> TYPE: PRT
<213> ORGANISM: Clostridium thermocellum

<400> SEQUENCE: 205

Asp Leu Asn Gly Asp Lys Gln Val Asn Ser Thr Asp Tyr Thr Ala Leu
1               5                   10                  15

Lys Arg His Leu Leu Asn Ile Thr
            20

<210> SEQ ID NO 206
<211> LENGTH: 24
<212> TYPE: PRT
<213> ORGANISM: Clostridium thermocellum

<400> SEQUENCE: 206

Asp Leu Asn Gly Asp Gly Lys Val Asp Ser Thr Asp Leu Met Ile Leu
1               5                   10                  15

His Arg Tyr Leu Leu Gly Ile Ile
            20

<210> SEQ ID NO 207
<211> LENGTH: 24
<212> TYPE: PRT
<213> ORGANISM: Clostridium thermocellum

<400> SEQUENCE: 207

```
Asp Leu Asn Gly Asp Gly Asn Val Asn Ser Thr Asp Ser Thr Leu Met
1               5                   10                  15

Ser Arg Tyr Leu Leu Gly Ile Ile
            20

<210> SEQ ID NO 208
<211> LENGTH: 24
<212> TYPE: PRT
<213> ORGANISM: Clostridium thermocellum

<400> SEQUENCE: 208

Asp Leu Asn Gly Asp Gly Lys Val Asn Ser Thr Asp Tyr Asn Ile Leu
1               5                   10                  15

Lys Arg Tyr Leu Leu Lys Tyr Ile
            20

<210> SEQ ID NO 209
<211> LENGTH: 24
<212> TYPE: PRT
<213> ORGANISM: Clostridium thermocellum

<400> SEQUENCE: 209

Asp Leu Asn Gly Asp Gly Arg Val Asn Ser Thr Asp Leu Ala Val Met
1               5                   10                  15

Lys Arg Tyr Leu Leu Lys Gln Val
            20

<210> SEQ ID NO 210
<211> LENGTH: 24
<212> TYPE: PRT
<213> ORGANISM: Clostridium thermocellum

<400> SEQUENCE: 210

Asp Leu Asn Gly Asp Gly Lys Ala Asn Ser Thr Asp Tyr Gln Leu Leu
1               5                   10                  15

Lys Arg Tyr Ile Leu Lys Thr Ile
            20

<210> SEQ ID NO 211
<211> LENGTH: 24
<212> TYPE: PRT
<213> ORGANISM: Clostridium thermocellum

<400> SEQUENCE: 211

Asp Ile Asp Gly Asn Gly Glu Ile Ser Ser Ile Asp Tyr Ala Ile Leu
1               5                   10                  15

Lys Ser His Leu Ile Asn Ser Asn
            20

<210> SEQ ID NO 212
<211> LENGTH: 24
<212> TYPE: PRT
<213> ORGANISM: Clostridium thermocellum

<400> SEQUENCE: 212

Asp Val Asp Gly Asn Gly Tyr Val Asn Ser Ile Asp Leu Ala Ile Leu
1               5                   10                  15

Gln Met Tyr Leu Leu Gly Lys Gly
            20

<210> SEQ ID NO 213
```

```
<211> LENGTH: 24
<212> TYPE: PRT
<213> ORGANISM: Clostridium thermocellum

<400> SEQUENCE: 213

Asp Val Asn Gly Asn Gly Ser Ile Glu Ser Thr Asp Cys Val Trp Val
1               5                   10                  15

Lys Arg Tyr Leu Leu Lys Gln Ile
            20

<210> SEQ ID NO 214
<211> LENGTH: 24
<212> TYPE: PRT
<213> ORGANISM: Clostridium thermocellum

<400> SEQUENCE: 214

Asp Val Asn Gly Asn Gly Thr Ile Asp Ser Thr Asp Tyr Gln Leu Leu
1               5                   10                  15

Lys Arg Phe Ile Leu Lys Val Ile
            20

<210> SEQ ID NO 215
<211> LENGTH: 1008
<212> TYPE: DNA
<213> ORGANISM: Clostridium thermocellum

<400> SEQUENCE: 215
gcaaatacac cggtatcagg caatttgaag gttgaattct acaacagcaa tccttcagat      60
actactaact caatcaatcc tcagttcaag gttactaata ccggaagcag tgcaattgat     120
ttgtccaaac tcacattgag atattattat acagtagacg acagaaaga tcagaccttc     180
tggtgtgacc atgctgcaat aatcggcagt aacggcagct acaacggaat tacttcaaat     240
gtaaaaggaa catttgtaaa aatgagttcc tcaacaaata acgcagacac ctaccttgaa     300
ataagcttta caggcggaac tcttgaaccg ggtgcacatg ttcagataca aggtagattt     360
gcaaagaatg actggagtaa ctatacacag tcaaatgact actcattcaa gtctgcttca     420
cagtttgttg aatgggatca ggtaacagca tacttgaacg tgttcttgt atggggtaaa     480
gaacccggtg gcagtgtagt accatcaaca cagcctgtaa caacaccacc tgcaacaaca     540
aaaccacctg caacaacaaa accacctgca acaacaatac cgccgtcaga tgatccgaat     600
gcaataaaga ttaaggtgga cacagtaaat gcaaaaccgg gagacacagt aaatatacct     660
gtaagattca gtggtatacc atccaaggga atagcaaact gtgactttgt atacagctat     720
gacccgaatg tacttgagat aatagagata aaaccgggag aattgatagt tgacccgaat     780
cctgacaaga gctttgatac tgcagtatat cctgacagaa agataatagt attcctgttt     840
gcagaagaca gcggaacagg agcgtatgca ataactaaag acggagtatt tgctacgata     900
gtagcgaaag taaatccgg agcacctaac ggactcagtg taatcaaatt tgtagaagta     960
ggcggatttg cgaacaatga ccttgtagaa cagaggacac agttctttt              1008

<210> SEQ ID NO 216
<211> LENGTH: 232
<212> TYPE: DNA
<213> ORGANISM: Clostridium thermocellum

<400> SEQUENCE: 216
ctcgagcggt actccttcta ctaaattata cggcgacgtc aatgatgacg gaaaagttaa      60
ctcaactgac gctgtagcat tgaagagata tgttttgaga tcaggtataa gcatcaacac     120
```

-continued

```
tgacaatgcc gatttgaatg aagacggcag agttaattca actgacttag gaattttgaa      180
gagatatatt ctcaaagaaa tagatacatt gccgtacaag aactaaggat cc              232
```

<210> SEQ ID NO 217
<211> LENGTH: 71
<212> TYPE: DNA
<213> ORGANISM: Artificial
<220> FEATURE:
<223> OTHER INFORMATION: Synthetic Construct - primer

<400> SEQUENCE: 217

```
ctcgagcggt actccttcta ctaaattata cggcgacgtc aatgatgacg gaaaagttgc      60
ttcaactgac g                                                           71
```

<210> SEQ ID NO 218
<211> LENGTH: 88
<212> TYPE: DNA
<213> ORGANISM: Artificial
<220> FEATURE:
<223> OTHER INFORMATION: Synthetic Construct - primer

<400> SEQUENCE: 218

```
ggatccttag ttcttgtacg gcaatgtatc tatttctttg agaatatatc tcttcaaaat      60
tcctaagtca gttgaagcaa ctctgccg                                         88
```

<210> SEQ ID NO 219
<211> LENGTH: 71
<212> TYPE: DNA
<213> ORGANISM: Artificial
<220> FEATURE:
<223> OTHER INFORMATION: Synthetic Construct - primer

<400> SEQUENCE: 219

```
ctcgagcggt actccttcta ctaaattata cggcgacgtc aatgatgacg gaaaagttga      60
ttcaactgac g                                                           71
```

<210> SEQ ID NO 220
<211> LENGTH: 88
<212> TYPE: DNA
<213> ORGANISM: Artificial
<220> FEATURE:
<223> OTHER INFORMATION: Synthetic Construct - primer

<400> SEQUENCE: 220

```
ggatccttag ttcttgtacg gcaatgtatc tatttctttg agaatatatc tcttcaaaat      60
tcctaagtca gttgaatcaa ctctgccg                                         88
```

<210> SEQ ID NO 221
<211> LENGTH: 223
<212> TYPE: DNA
<213> ORGANISM: Clostridium thermocellum

<400> SEQUENCE: 221

```
ctcgagcgaa ccgccggttc aggttatacc cggtgatgta aacggtgacg gtcgtgtaaa      60
ttcatccgac ttgactctta tgaaaagata ccttttaaaa tccataagcg acttcccgac     120
accggaagga aaaattgcgg cggatttaaa cgaagacggc aaggtaaact cgacagattt     180
gttagcgctg aaaaaactcg ttctgagaga actttgagga tcc                       223
```

<210> SEQ ID NO 222

```
<211> LENGTH: 71
<212> TYPE: DNA
<213> ORGANISM: Artificial
<220> FEATURE:
<223> OTHER INFORMATION: Synthetic Construct - primer

<400> SEQUENCE: 222
ctcgagcgaa ccgccggttc aggttatacc cggtgatgta aacggtgacg gtcgtgtaga       60
ttcatccgac t                                                           71

<210> SEQ ID NO 223
<211> LENGTH: 67
<212> TYPE: DNA
<213> ORGANISM: Artificial
<220> FEATURE:
<223> OTHER INFORMATION: Synthetic Construct - primer

<400> SEQUENCE: 223
ggatcctcaa agttctctca gaacgagttt tttcagcgct aacaaatctg tcgaatctac       60
cttgccg                                                                67

<210> SEQ ID NO 224
<211> LENGTH: 1166
<212> TYPE: DNA
<213> ORGANISM: Clostridium thermocellum

<400> SEQUENCE: 224
agatctgcag gtgtgccttt aacacaaaa taccctatg gtcctacttc tattgccgat        60
aatcagtcgg aagtaactgc aatgctcaaa gcagaatggg aagactggaa gagcaagaga      120
attacctcga acggtgcagg aggatacaag agagtacagc gtgatgcttc caccaattat      180
gatacggtat ccgaaggtat gggatacgga cttcttttgg cggtttgctt taacgaacag      240
gctttgtttg acgatttata ccgttacgta aaatctcatt tcaatggaaa cggacttatg      300
cactggcaca ttgatgccaa caacaatgtt acaagtcatg acggcggcga cggtgcggca      360
accgatgctg atgaggatat tgcacttgcg ctcatatttg cggacaagtt atggggttct      420
tccggtgcaa taaactacgg gcaggaagca aggacattga taaacaatct ttacaaccat      480
tgtgtagagc atggatccta tgtattaaag cccggtgaca gatggggagg ttcatcagta      540
acaaacccgt catattttgc gcctgcatgg tacaaagtgt atgctcaata tacaggagac      600
acaagatgga atcaagtggc ggacaagtgt taccaaattg ttgaagaagt taagaaatac      660
aacaacggaa ccggccttgt tcctgactgg tgtactgcaa gcggaactcc ggcaagcggt      720
cagagttacg actacaaata tgatgctaca cgttacggct ggagaactgc cgtggactat      780
tcatggtttg gtgaccagag agcaaaggca aactgcgata tgctgaccaa attctttgcc      840
agagacgggg caaaaggaat cgttgacgga tacacaattc aaggttcaaa aattagcaac      900
aatcacaacg catcatttat aggacctgtt gcggcagcaa gtatgacagg ttacgatttg      960
aactttgcaa aggaacttta tagggagact gttgctgtaa aggacagtga atattacgga     1020
tattacggaa acagcttgag actgctcact ttgttgtaca taacaggaaa cttcccgaat     1080
cctttgagtg acctttccgg ccaaccgaca ccaccgtcga atccgacacc ttcattgcct     1140
cctcaggttg tttacggtcc ctcgag                                          1166
```